(12) United States Patent
Keller et al.

(10) Patent No.: US 12,376,838 B2
(45) Date of Patent: Aug. 5, 2025

(54) BIOPSY DEVICE WITH REMOTE MULTI-CHAMBER TISSUE SAMPLE HOLDER

(71) Applicant: Devicor Medical Products Inc., Cincinnati, OH (US)

(72) Inventors: Bryan R. Keller, Loveland, OH (US); John Kevin Bruce, Burlington, KY (US); Peter Shadix, Cincinnati, OH (US); Rachel Yoon Choung, Cincinnati, OH (US); David Shuart, Mason, OH (US); Jordan Rebellino, Cincinnati, OH (US); Andrew Paul Nock, Dayton, OH (US); Bryan Superville, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 512 days.

(21) Appl. No.: 17/965,984

(22) Filed: Oct. 14, 2022

(65) Prior Publication Data
US 2023/0034865 A1 Feb. 2, 2023

Related U.S. Application Data

(63) Continuation of application No. 15/977,471, filed on May 11, 2018, now Pat. No. 11,504,101.

(60) Provisional application No. 62/505,417, filed on May 12, 2017.

(51) Int. Cl.
A61B 10/02 (2006.01)
A61B 10/00 (2006.01)

(52) U.S. Cl.
CPC ...... *A61B 10/0275* (2013.01); *A61B 10/0283* (2013.01); *A61B 10/0096* (2013.01); *A61B 2010/0208* (2013.01); *A61B 2010/0225* (2013.01)

(58) Field of Classification Search
CPC ............ A61B 10/0275; A61B 10/0283; A61B 10/0096; A61B 2010/0225
See application file for complete search history.

(56) References Cited

U.S. PATENT DOCUMENTS

| | | | |
|---|---|---|---|
| 6,875,182 B2 * | 4/2005 | Wardle | A61B 10/0233 600/564 |
| 2004/0034280 A1 * | 2/2004 | Privitera | A61B 10/0266 600/170 |

(Continued)

*Primary Examiner* — Daniel L Cerioni
(74) *Attorney, Agent, or Firm* — Frost Brown Todd LLP

(57) ABSTRACT

A biopsy system includes a biopsy device, a control module, and a tissue transport tube. The biopsy device includes a probe, a needle, a cutter, and a transport valve. The needle extends distally from the probe. The cutter is movable relative to the needle and defines a cutter lumen. The holster is configured to couple to the probe. The transport valve is in communication with the cutter lumen. The control module is in communication with the biopsy device and includes a sample management assembly configured to receive one or more tissue samples severed by the cutter. The transport tube extends between the sample management assembly and the biopsy device. The transport tube is in communication with the transport valve such that the transport tube is configured to receive the one or more tissue samples severed by the cutter.

20 Claims, 35 Drawing Sheets

(56) References Cited

U.S. PATENT DOCUMENTS

| | | | |
|---|---|---|---|
| 2005/0240118 A1* | 10/2005 | Huitema | A61B 10/0275 600/568 |
| 2009/0171243 A1* | 7/2009 | Hibner | A61B 10/0275 600/568 |
| 2009/0198149 A1* | 8/2009 | Privitera | A61B 10/0266 600/566 |
| 2012/0283563 A1* | 11/2012 | Moore | A61B 8/463 600/437 |

* cited by examiner

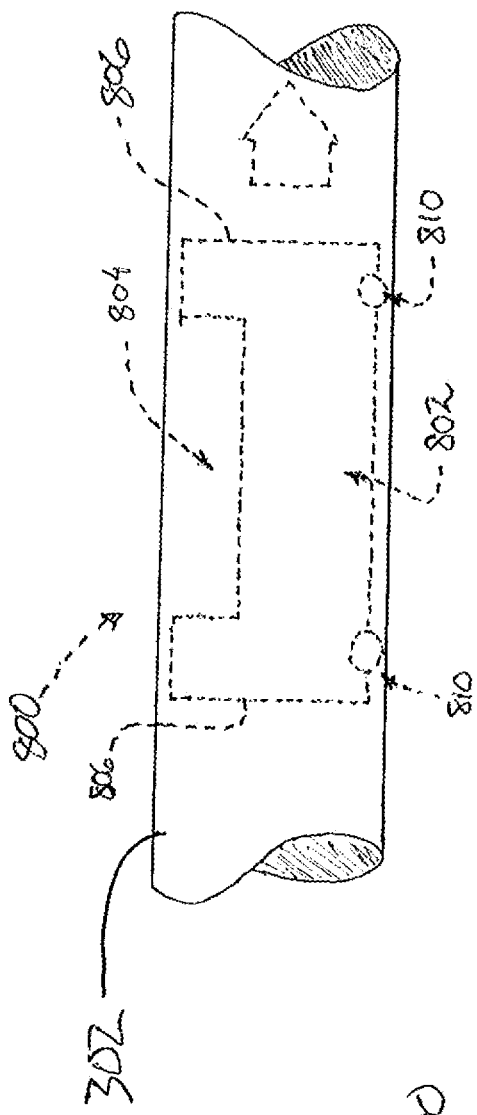
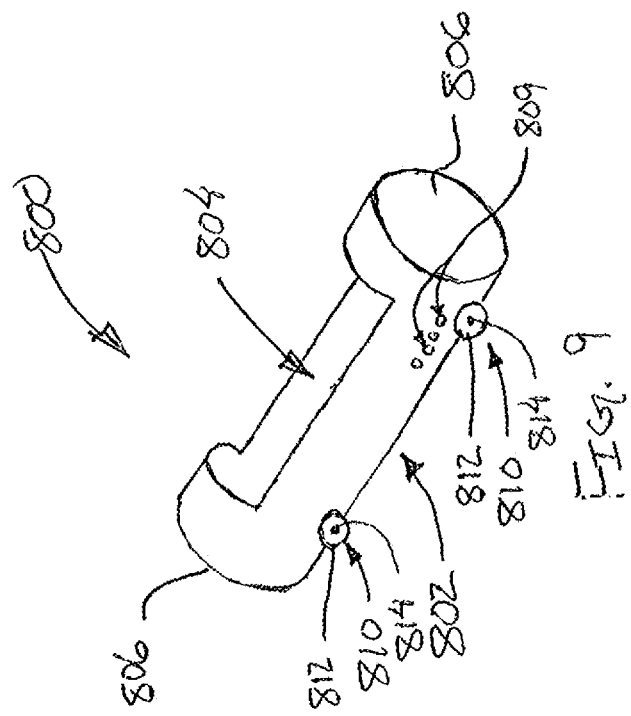

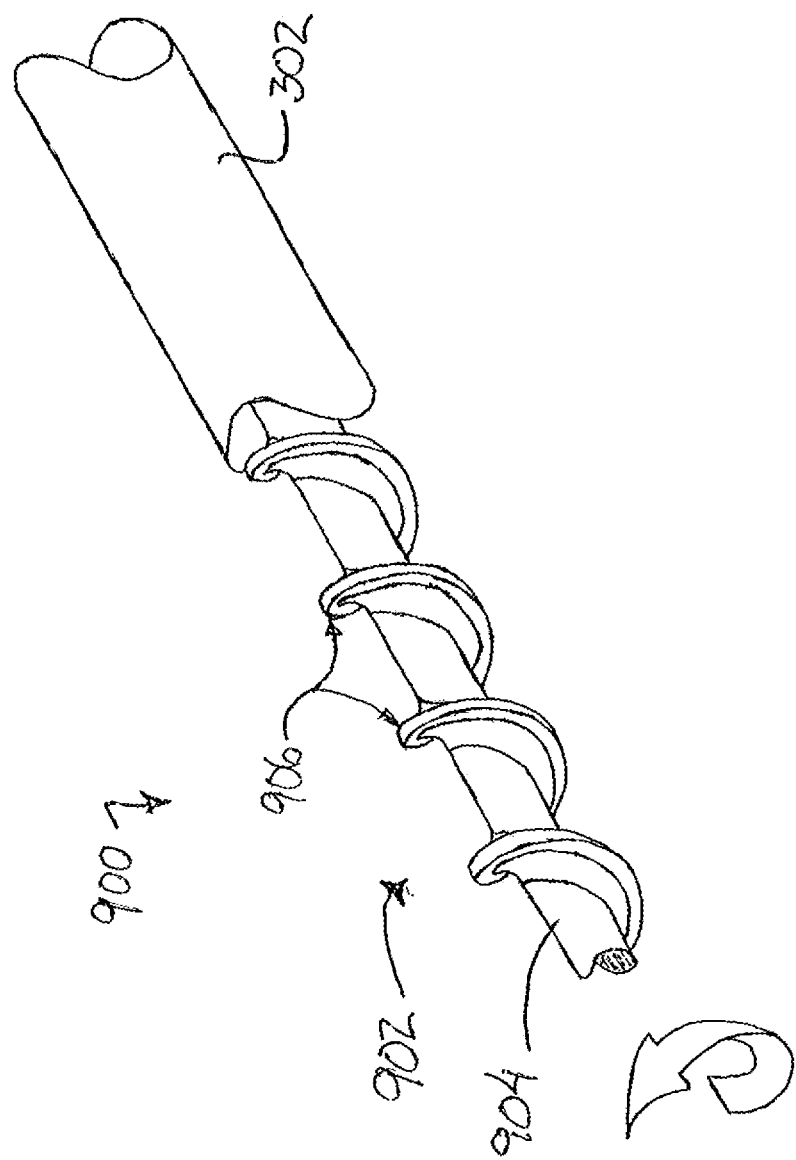

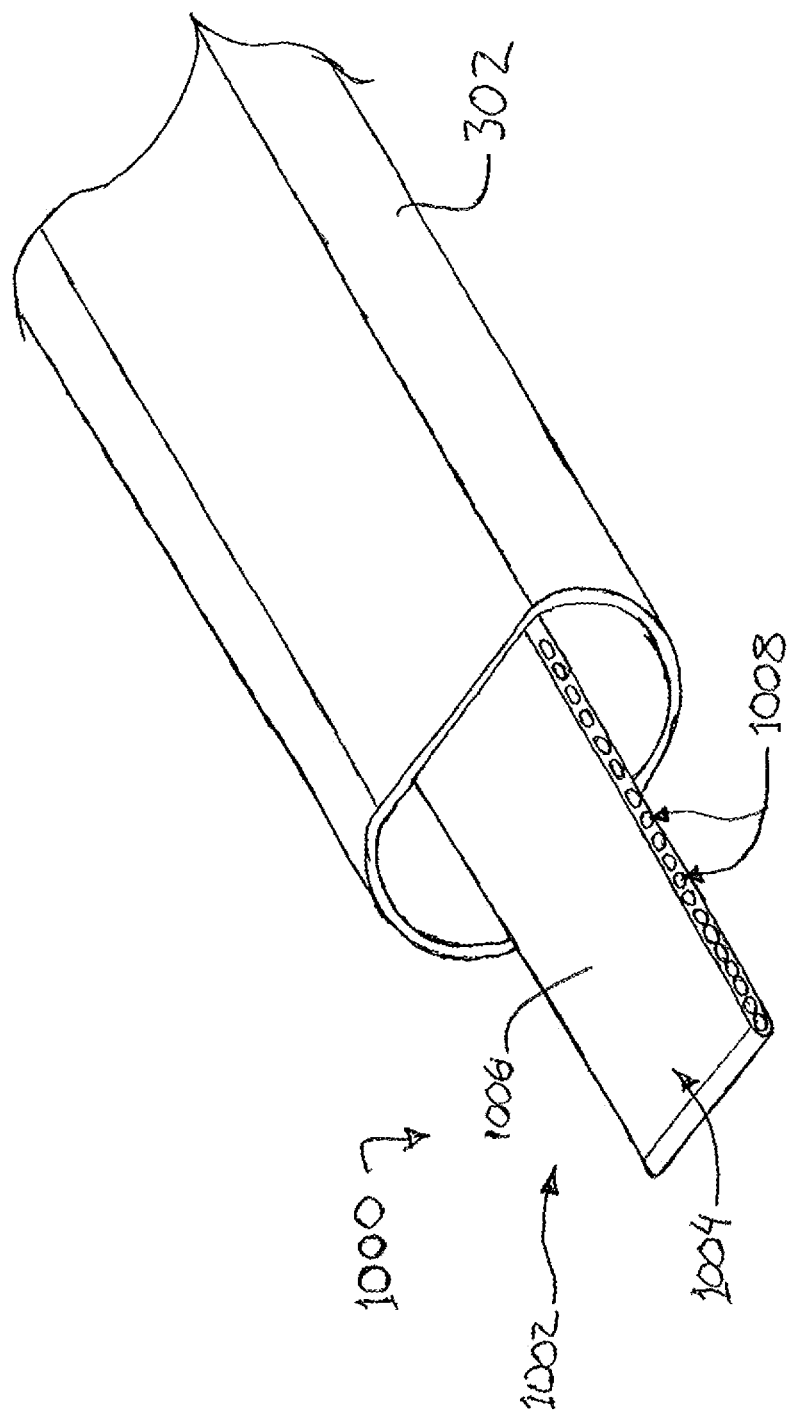

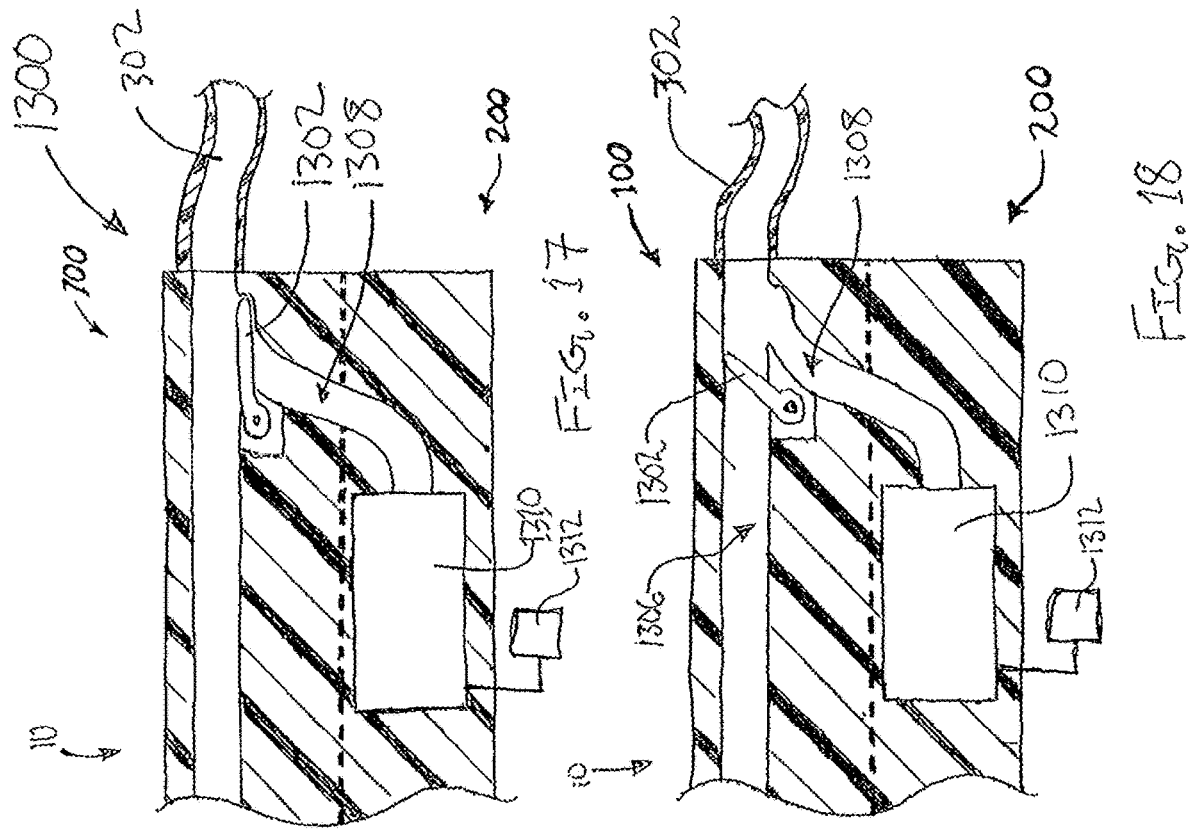

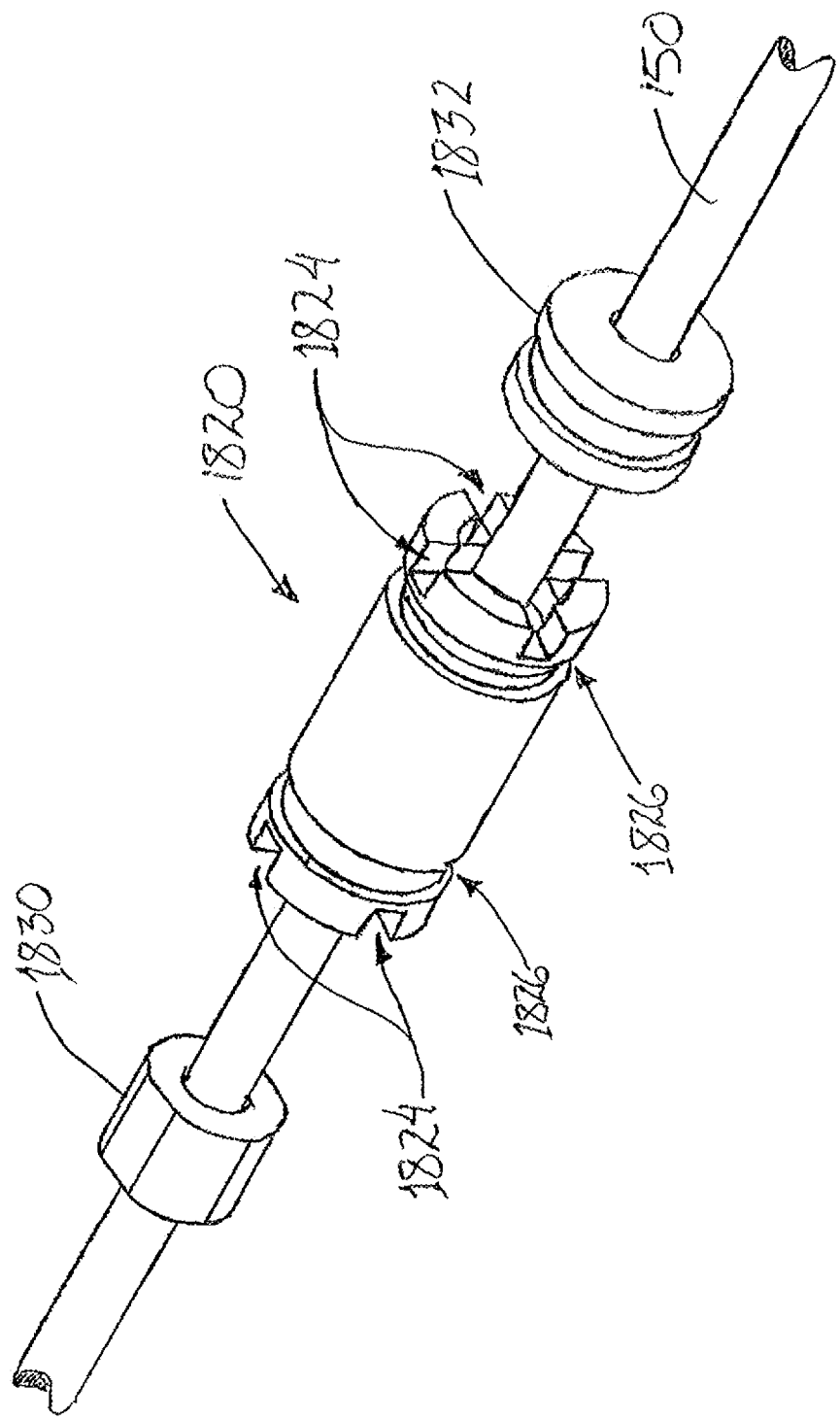

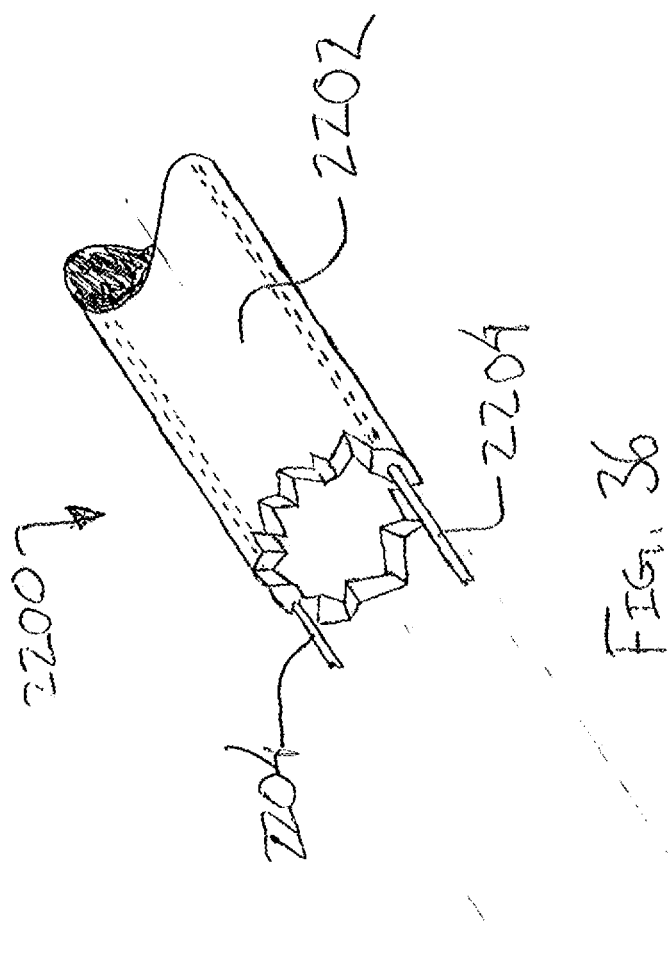

BIOPSY DEVICE WITH REMOTE MULTI-CHAMBER TISSUE SAMPLE HOLDER

PRIORITY

This application is a continuation of U.S. Ser. No. 15/977,471, entitled "Biopsy Device with Remote Multi-Chamber Tissue Sample Holder," filed on May 11, 2018, which claims priority to U.S. Provisional Patent App. No. 62/505,417, entitled "Biopsy Device with Remote Multi-Chamber Tissue Sample Holder," filed May 12, 2017, the disclosures of which are incorporated by reference herein.

BACKGROUND

Biopsy samples have been obtained in a variety of ways in various medical procedures using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Biopsy devices may be used under stereotactic guidance, ultrasound guidance, MRI guidance, PEM guidance, BSGI guidance, or otherwise.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,432,065, entitled "Method for Using a Surgical Biopsy System with Remote Control for Selecting an Operational Mode," issued Aug. 13, 2002; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 21, 2012; U.S. Pat. No. 8,206,316, entitled "Tetherless Biopsy Device with Reusable Portion," issued Jun. 26, 2012; U.S. Pat. No. 8,702,623, entitled "Biopsy Device with Discrete Tissue Chambers," issued Apr. 22, 2014; U.S. Pat. No. 8,764,680, entitled "Handheld Biopsy Device with Needle Firing," issued Jul. 1, 2014; U.S. Pat. No. 9,095,326, entitled "Biopsy System with Vacuum Control Module," issued Aug. 4, 2015; U.S. Pat. No. 9,326,755, entitled "Biopsy Device Tissue Sample Holder with Bulk Chamber and Pathology Chamber," issued May 3, 2016; and U.S. Pat. No. 9,345,457, entitled "Presentation of Biopsy Sample by Biopsy Device," issued May 24, 2016. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006, now abandoned; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010, now abandoned; U.S. Pat. Pub. No. 2012/0283563, entitled "Biopsy Device with Manifold Alignment Feature and Tissue Sensor," published Nov. 8, 2012, now abandoned; U.S. Pat. App. No. 2013/0150751, entitled "Biopsy Device With Slide-In Probe," published Jun. 13, 2013; and U.S. Pat. App. No. 2013/0324882, entitled "Control for Biopsy Device," published Dec. 5, 2013. The disclosure of each of the above-cited U.S. patent application Publications, U.S. Non-Provisional patent applications, and U.S. Provisional patent applications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a perspective view of a container that may be readily used with the tissue transport tube of the biopsy system of FIG. 1;

FIG. 10 depicts a front elevational view of the container of FIG. 9 being used with the tissue transport tube of the biopsy system of FIG. 1;

FIG. 11 depicts a perspective view of a transport mechanism that may be readily incorporated into the tissue transport tube of the biopsy system of FIG. 1;

FIG. 12 depicts a perspective view of an alternative transport mechanism that may be readily incorporated into the tissue transport tube of the biopsy system of FIG. 1;

FIG. 17 depicts a side cross-sectional view of a transport valve that may be readily incorporated into a biopsy device of the biopsy system of FIG. 1;

FIG. 18 depicts a side cross-sectional view of the transport valve of FIG. 17, the transport valve in a tissue transport state;

FIG. 27 depicts a perspective view of the vent assembly of FIG. 26, with a valve body removed;

FIG. 36 depicts a perspective view of an alternative tissue transport tube that may be readily incorporated into the biopsy system of FIG. 1;

Figure 1:
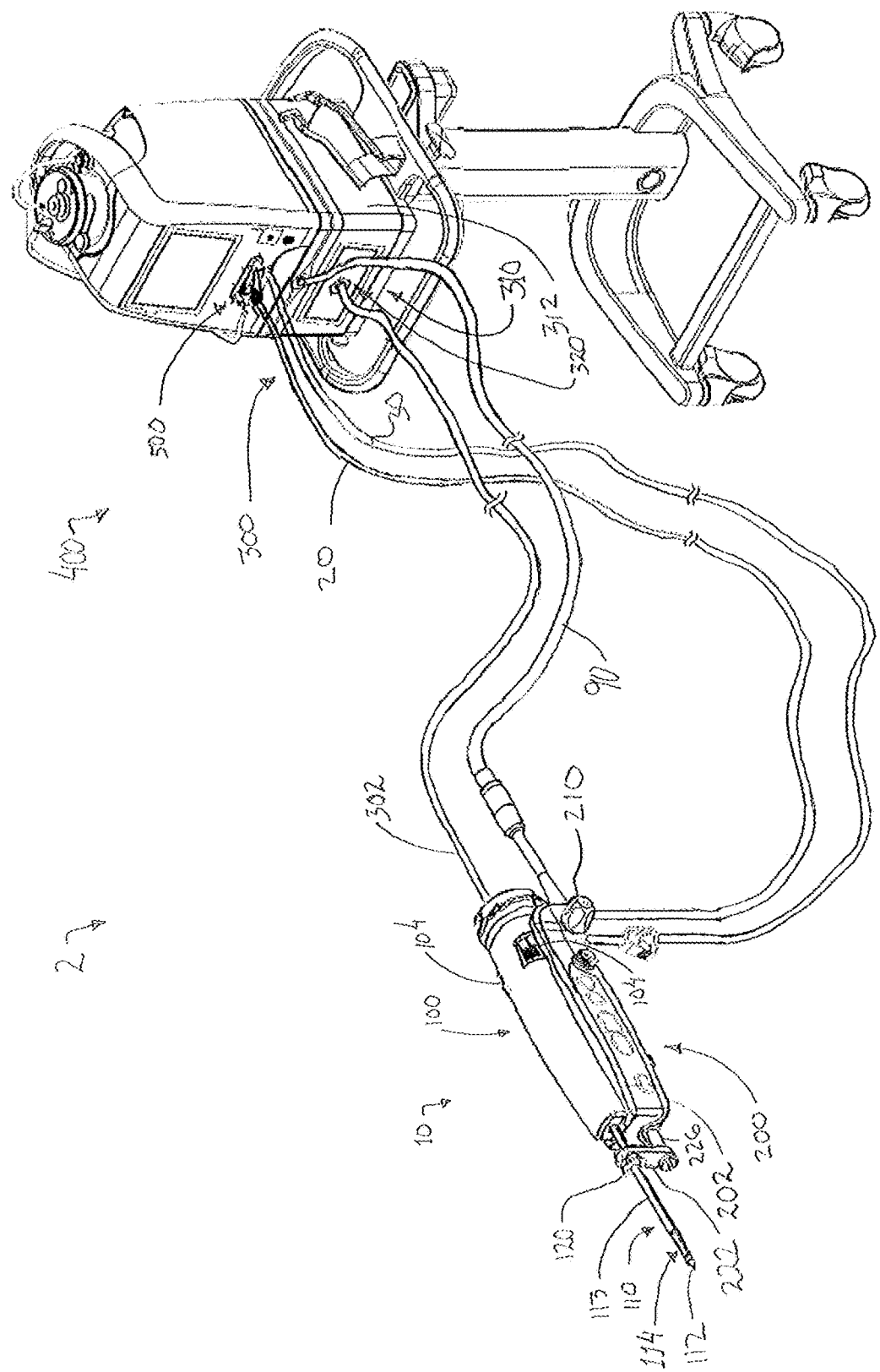
FIG. 1 depicts a perspective view of an exemplary biopsy system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

FIG. 1 depicts an exemplary biopsy system (2) comprising a biopsy device (10) and a vacuum control module (400). Biopsy device (10) of this example comprises a probe (100) and a holster (200). A needle (110) extends distally from probe (100), and is inserted into a patient's tissue to obtain tissue samples. These tissue samples are communicated through needle and into a tissue handling assembly (300) with a tissue transport tube (302) connected at the proximal end of probe (100), as will also be described in greater detail below. It should also be understood that the use of the term "holster" herein should not be read as requiring any portion of probe (100) to be inserted into any portion of holster (200). For instance, in the present example, holster (200) includes a set of prongs (not shown) that are received by at least a portion of probe (100) to releasably secure probe (100) to holster (200). Probe (100) also includes a set of resilient tabs (104) that may be pressed inwardly to disengage the prongs, such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition, or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited within at least a portion of tissue handling assembly (300), and later retrieved from tissue handling assembly (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

Holster (200) of the present example includes an outer housing (202) that encloses various components that are used to drive various components of probe (100) for the collection of tissue samples. Although not shown, it should be understood that holster (200) of the present example includes one or more gears (not shown) that mesh with corresponding gears of probe (100). In particular, these gears are exposed through an upper portion of outer housing (202) to mesh with corresponding gears of probe (100) when probe (100) and holster (200) are coupled together. This configuration permits holster (200) to communicate rotary motion to probe (100), thereby driving various components of probe (100) for the collection of tissue samples. For instance, the gears may drive an actuation assembly associated with a hollow tubular cutter (150) (see FIG. 26) within needle (110) to sever tissue samples received within a lateral aperture (114) defined by needle (110). Likewise, other gears may be employed to rotate needle (110).

As noted above, in some examples a gear associated with holster (200) can provide rotation of needle (110) relative to probe (100). In the present example, this rotation is manually initiated by rotating knob (210). In particular, knob (210) is coupled with the gear associated with rotation of needle (110) by a series of gears (not shown) and shafts (not shown), such that rotation of knob (210) rotates needle (110). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which is incorporated by reference herein. In some other versions, needle (110) is rotated by a motor. In still other versions, needle (110) is simply rotated by rotating thumbwheel (116). Various other suitable ways in which rotation of needle (110) may be provided will be apparent to those of ordinary skill in the art in view of the teachings herein. It should also be understood that some versions may provide no rotation of needle (110).

Holster (200) also includes a firing rod (226) and fork (222), which couple with needle (110) and fire needle (110) distally. By way of example only, such firing may be useful in instances where biopsy device (10) is mounted to a stereotactic table fixture or other fixture, with tip (112) adjacent to a patient's breast, such that the needle firing mechanism may be activated to drive needle (110) into the patient's breast. The needle firing mechanism may be configured to drive needle (110) along any suitable range of motion, to drive tip (112) to any suitable distance relative to fixed components of probe (100).

In the present example, the needle firing mechanism is coupled with needle (110) via a firing rod (226) and a firing fork (222). Firing rod (226) and firing fork (222) are unitarily secured together. Firing fork (222) includes a pair of prongs that receive hub member (120) of needle (110) therebetween. The prongs of firing fork (222) are positioned between an annular flange and a thumbwheel of hub member (120), such that needle (110) will translate unitarily with firing rod (226) and fork (222). The prongs nevertheless removably receive hub member (120), such that fork (222) may be readily secured to hub member (120) when probe (100) is coupled with holster (200); and such that hub member (120) may be readily removed from fork (222) when probe (100) is decoupled from holster (200). The prongs are also configured to permit hub member (120) to rotate between the prongs. Other suitable components, configurations, and relationships will be apparent to those of ordinary skill in the art in view of the teachings herein. The internal components of the needle firing mechanism of the present example are configured and arranged as described in Non-Provisional U.S. Pat. No. 8,858,465, entitled "Biopsy Device with Motorized Needle Firing," issued on Oct. 14, 2014, the disclosure of which is incorporated by reference herein.

Holster (200) of the present example is powered by one or more motors (not shown) contained within outer housing (202). These motors are generally configured to drive one or more gears to thereby rotate and translate a tubular cutter (150) disposed within needle (110). Holster (200) also includes a motor (not shown) that is operable to drive firing rod (226), to thereby arm and fire needle (110). All motors referred to herein are contained within holster (200) in the present example and receive power from vacuum control module (400) via cable (90). In addition, data may be communicated between vacuum control module (400) and holster (200) via cable (90). In some other versions, one or more motors are powered by one or more batteries located within holster (200) and/or probe (100). It should therefore be understood that, as with other components described herein, cable (90) is merely optional. As yet another merely illustrative variation, motors may be powered pneumatically, such that cable (90) may be substituted with a conduit communicating a pressurized fluid medium to holster (200). As still other merely illustrative variation, cable (90) may include one or more rotary drive cables that are driven by motors that are located external to holster (200). It should also be understood that two or three of the motors may be combined as a single motor. Other suitable ways in which various the motors may be driven will be apparent to those of ordinary skill in the art in view of the teachings herein.

Probe (100) of the present example includes a needle (110) extending distally from probe (100) that is inserted into a patient's tissue to obtain tissue samples. These tissue samples are transported proximally through needle (110) and into transport tube (302), where the tissue samples may be deposited within at least a portion of tissue handling assembly (300), as will be described in greater detail below. Vacuum control module (400) is coupled with probe (100) via a valve assembly (500) and tubes (20, 30), which is operable to selectively provide vacuum, saline, atmospheric air, and venting to probe (100). Although the present example is shown with a pair of tubes (20, 30), it should be understood that in some examples one tube may be omitted in lieu of a tissue transport tube (302) discussed below. The internal components of the valve assembly of the present example are configured and arranged as described in U.S. Pub. No. 2013/0218047, entitled "Biopsy Device Valve Assembly," published Aug. 22, 2013, the disclosure of which is incorporated by reference herein.

As described above, probe (100) may include one or more gears to mesh with corresponding gears of holster (200). These gears are operable to drive a cutter actuation mechanism in probe (100). Probe (100) may also include another gear that is configured to mesh with a corresponding gear of holster (200) to thereby rotate needle (110).

Needle (110) of the present example comprises a cannula (113) having a tissue piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," issued on Aug. 12, 2014, the disclosure of which is incorporated by reference herein. As another merely illustrative example, tip (112) may be configured in accordance with at least some of the teachings in U.S. Pat. No. 9,486,186, entitled "Biopsy Device with Slide-In Probe," issued on Nov. 8, 2016, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). Although not shown, it should be understood that a hollow tubular cutter (150) having a sharp distal edge is located within needle (110). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

In some examples, needle (110) also includes a longitudinal wall (not shown) extending proximally from the proximal portion of tip (112). In such examples, the wall may only extend along a length less than the full length of cannula (113). However, in other examples such a wall may extend the full length of cannula (113) if desired. Where needle (110) includes the wall, the wall may define a two-lumen configuration within needle (110). In examples where the wall only extends for a portion of needle (110), it should be understood that at least a portion of cutter (150) may also define the two-lumen configuration of needle (110). Furthermore, to facilitate fluid flow between lumens, the wall may include a plurality of openings (not shown). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. In the present example, hub member (120) defines a thumbwheel feature to provide manual rotation of needle. Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein.

As noted above, needle (110) contains a hollow tubular cutter that is operable to simultaneously translate and rotate relative to needle (110) to sever a tissue sample from tissue protruding through lateral aperture (114). Although not shown, it should be understood that in some examples such a cutter (150) may be operatively coupled to a cutter drive mechanism disposed within probe. Such a cutter drive mechanism may be in communication with one or more gears, which may mesh with one or more corresponding gears of holster (200). The cutter drive mechanism may thus be driven by gears of holster (200) to simultaneously rotate and translate cutter (150) disposed within needle (110). In some examples, cutter (150) drive mechanism may include various threaded and keyed features to facilitate simultaneous rotation and translation of cutter (150). In such examples, a single rotatory input may be converted by the cutter drive mechanism into both rotation and translation of cutter (150). Alternatively, in other examples, rotation and translation of cutter (150) may be supplied by separate rotary inputs. In yet other examples, both rotation and translation of cutter (150) may be provided by two rotary inputs acting together such as by two gears moving at different rotational speeds. In some versions, the foregoing cutter actuation components are further configured in accordance with at least some of the teachings of U.S. Pat. No. 9,345,457, entitled "Presentation of Biopsy Sample by Biopsy Device," issued on May 24, 2016, the disclosure of which is incorporated by reference herein. As yet another merely illustrative example, cutter (150) disposed within needle (110) may be rotated and/or translated using pneumatic motors, etc. Still other suitable ways in which cutter (150) disposed within needle (110) may be actuated will be apparent to those of ordinary skill in the art in view of the teachings herein.

Figure 2:
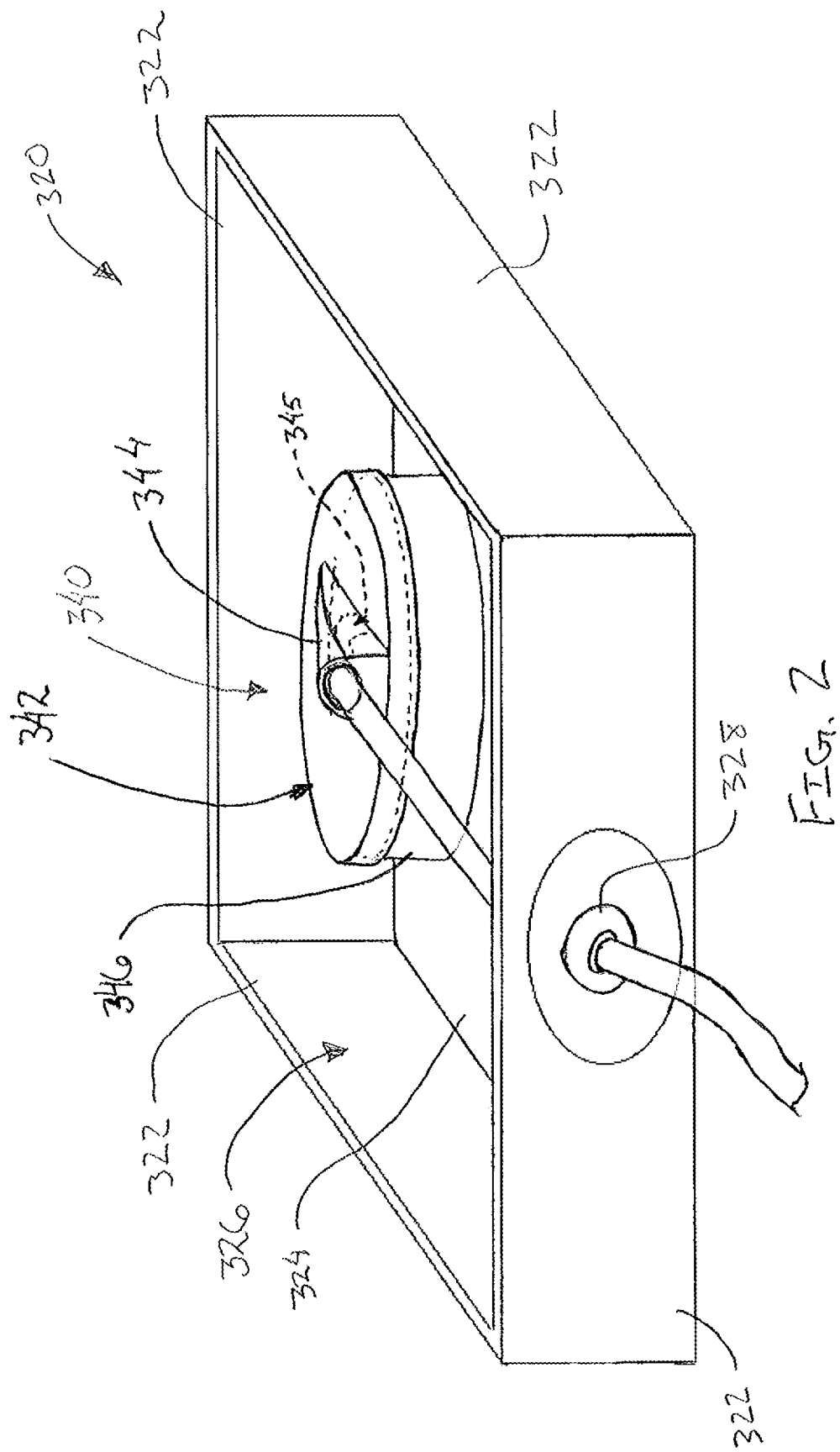
FIG. 2 depicts a perspective view of an exemplary tissue handler that may be readily incorporated into the system of FIG. 1.
Figure 3:
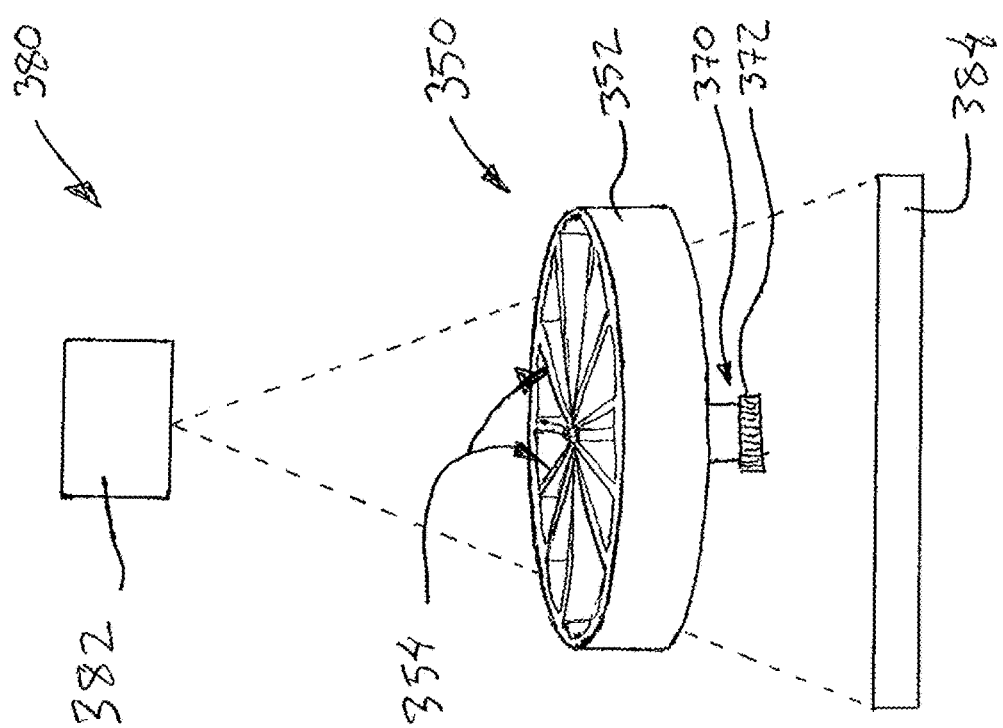
FIG. 3 depicts a partial perspective view of a tissue sample holder of the tissue handler of FIG. 2.

Tissue handling assembly (300) is best seen in FIGS. 1-3. As seen in FIG. 1, at least a portion of tissue handling assembly (300) is incorporated into vacuum control module (400). However, it should be understood that in other examples, tissue handling assembly (300) may be entirely independent and separate from vacuum control module (400). Tissue handling assembly (300) of the present example includes a tissue transport tube (302), and a tissue handler (310). Tube (302) extends from tissue handler (310) to biopsy device (10). As will be described in greater detail below, tube (302) is generally configured to receive tissue samples from cutter (150) disposed within needle (110) and to communicate such tissue samples from biopsy device (10) to tissue handler (310).

Tissue handler (310) generally includes an outer housing (312) and a collection drawer (320). As will be described in greater detail below, tissue handler (310) is generally configured to receive a plurality of tissue samples from sample transport tube (302). The tissue samples are then generally arranged in a predetermined configuration. As will also be described in greater detail below, tissue hander (310) may include various sample analysis features to provide procedure room analysis of tissue samples collected within tissue handler (310). Suitable analysis features may include, among other things, x-ray transmitters and receivers, CCD cameras for visual inspection, bioimpedance sensors, and/or etc.

Collection drawer (320) is received within tissue handler (310). Collection drawer (320) is generally translatable into and out of tissue handler (310) to provide access to the interior of tissue handler (310) and thereby provide removal of tissue samples and/or various components from tissue handler (310), as will be described in greater detail below. In some examples, collection drawer (320) is manually operable to translate relative to tissue handler (310). In other examples, translation of collection drawer (310) is powered by motor driven or pneumatically driven assemblies to provide automatic or semi-automatic translation of collection drawer (310).

As best seen in FIG. 2, the interior of collection drawer (320) includes a plurality of sidewalls (322) and a floor (324) defining an interior space (326). Tissue transport tube (302) communicates with the interior space (326) of collection drawer (320) through a tube port (328) disposed in at least one sidewall (322) of collection drawer (320). Although not shown, it should be understood that in some examples, sidewalls (322) and/or floor (324) may include one or more ports to provide draining of fluid from collection drawer (320). For instance, in some instances biopsy device (10) is used with saline or other fluid mediums. Through the tissue sample collection process, an unsatisfactory amount of refuse fluids from the biopsy procedure may flow into interior space (326) of collection drawer (320). Thus, it may be desirable in such examples to include drainage ports through sidewalls (322) and/or floor (324).

In the present example, collection drawer (320) contains a tissue sample holder (340) within interior space (326) defined by sidewalls (322) and floor (324). Tissue sample holder (340) of the present example is generally in communication with tissue transport tube (302) to receive a plurality of tissue samples in a predetermined configuration. Tissue sample holder (340) of the present example comprises a tissue directing top (342), and outer container (346) and a rotatable sample tray (350) disposed within top (342) and outer container (346). Top (342) is generally configured to be secured to outer container (346) to thereby direct tissue samples from tissue transport tube (302) and into sample tray (350), as will be described in greater detail below. Although not shown, it should be understood that in some examples top (342) and outer container (346) may include complementary coupling features to secure top (342) to outer container (346). By way of example only, suitable coupling features may include threading, bayonet fittings, interference fittings, snap fit connectors, and/or etc. In addition, in some examples top (342) and or outer container (346) may include sealing features to seal an interior of outer container (346) relative to the exterior of outer container (346). As will be described in greater detail below, such sealing features may permit vacuum pressure to build within outer container (346) to thereby transport tissue samples through tissue transport tube (302).

Although not shown, it should be understood that in the present example outer container (346) is in communication with a vacuum tube or other vacuum source. In the present example, vacuum is supplied from vacuum control module (400) to induce negative pressure within outer container (346). This negative pressure is supplied selectively to induce corresponding negative pressure in tissue transport tube (302), which results in transport of tissue samples through tissue transport tube (302) and into tissue sample holder (340), as will be described in greater detail below. In the present example, vacuum pressure is applied generally to outer container (346) such that the entirety of the interior of outer container (346) is placed under negative pressure. However, it should be understood that in some examples vacuum pressure may be applied locally such that certain specific segments of outer container (346) may be under negative pressure while other segment remains under atmospheric or other pressure conditions. Examples with localized vacuum pressure will be described in greater detail below.

Top (342) includes a redirection elbow (344) to direct tissue samples from tissue transport tube (302) and into sample tray (350). In particular, redirection elbow (344) defines an elbow-shaped lumen (345) (shown in phantom) extending through redirection elbow (344). Lumen (345) is configured to generally receives tissue samples in a lateral direction relative to top (342) and then redirect such tissue samples towards an axial direction to thereby deposit such tissue samples within sample tray (350). To the extent that the term "elbow" or "elbow-shaped" used herein implies a 90-degree bend within lumen (345), it should be understood that no such implication is implied. In particular, it should be understood that lumen (345) may be shaped to provide any suitable bend within redirection elbow (344). For instance, in some examples, lumen (345) may be configured to provide a 45-degree bend or a 60-degree bend. Various other suitable bend angles for lumen (345) will be apparent to those of ordinary skill in the art in view of the teachings herein.

FIG. 3 shows sample tray (350) with top (342) and outer container (346) removed. As can be seen, sample tray (350) generally includes an outer cylindrical body (352) and a rotation shaft (370). Cylindrical body (352) includes a plurality of sidewalls (354). Sidewalls (354) define a plurality of pie-shaped tissue sample chambers (356). Each sample chamber (356) is configured to receive one or more tissue samples. Each sample chamber (356) is open to the top of sample tray (350) such that tissue samples are received within the top of sample tray (350). As will be understood, the top of sample tray (350) generally abuts tissue directing top (342) such that tissue directing top (342) directs tissue samples into each sample chamber (356) through the top of sample tray (350).

Although not shown, it should be understood that sample tray (350) also includes a floor in the bottom of cylindrical body (352). Thus, tissue samples received within each sample chamber (356) may be deposited on this floor. To promote the flow of vacuum through sample tray (350), the floor may include a plurality of openings or perforations. In addition, the plurality of openings or perforations may also promote the drainage of excess fluids while maintaining tissue samples within sample chambers (356).

Rotation shaft (370) is coupled to the underside of cylindrical body (352). Rotation shaft (370) is generally configured to rotate cylindrical body (352) to sequentially align a selected sample chamber (356) with redirection elbow (344) of tissue directing top (342). Thus, it should be understood that cylindrical body (352) is generally configured to be rotated after each tissue sample is collected to deposit a subsequent tissue sample in a subsequent sample chamber (356).

Rotation shaft (370) includes a threaded portion (372). Threaded portion (372) is generally configured to extend through floor (324) of collection drawer (320) to engage corresponding threaded features such as gears within tissue handler (310). In some examples, such gears are coupled to one or more motors to provide motorized rotation of cylindrical body (352). In the present example, gears and/or motor are incorporated directly into collection drawer (320) beneath floor (324). However, in other examples, gears and or motor may be located elsewhere within tissue handler (310) and may communicate with threaded portion (372) of rotation shaft (370) via intermediate gears, shafts, belts, harmonic drives, and/or etc.

As can also be seen in FIG. 3, the interior of tissue handler (310) includes an analysis assembly (380). In the present example, analysis assembly (380) is generally configured to provide some analysis of tissue samples in real time as they are collected within sample tray (350). Such analysis is generally preliminary in nature that occurs in the biopsy procedure room prior to analysis by a pathology laboratory. In some examples, at least some preliminary analysis may be desirable to initially assess the quality of any tissue samples collected. This preliminary assessment may provide an operator with immediate feedback related to the biopsy procedure. Analysis assembly (380) of the present example includes an x-ray source (382) and an x-ray detector (384). X-ray source (382) and x-ray detector (384) are a part of an integral real-time x-ray system. Thus, an operator may view x-ray imaging of one or more tissue samples as such tissue samples are collected within sample tray (350).

Although not shown, it should be understood that in other examples analysis assembly (380) may include other sample analysis features in addition to, or in lieu of, x-ray source (382) and x-ray detector (384). For instance, in some examples, x-ray source (382) is also equipped with a CCD camera to permit visual inspection of tissue samples with or without x-ray source (382) being energized. In addition, in some alternative uses it should be understood that both x-ray source (382) and x-ray detector (384) may be deactivated. In such uses, biopsy device (10) may be used under alternative guidance such as by ultrasonically based breast biopsy procedures.

As described above, tissue samples are generally transported from biopsy device (10) to tissue handler (310) via tissue transport tube (302). Generally, this transport is accomplished by applying a pressure differential between a proximal and distal end of a tissue sample being transported. Excess saline may also be used to aid with transport by providing a fluid seal and lubrication around the tissue sample. However, due to the physical properties of tissue samples, in some circumstances a pressure differential may be insufficient to completely transport a given tissue sample. Thus, it may be desirable to provide additional methods and devices configured to provide additional mechanisms to transport tissue samples through tissue transport tube (302). Various illustrative examples of additional methods and mechanisms to provide supplemental transport of tissue samples through tissue transport tube (302) are described below. Although particular methods and mechanisms are described below, it should be understood that various alternative methods and mechanisms will be apparent to those of ordinary skill in the art in view of the teachings herein.

Figure 4:
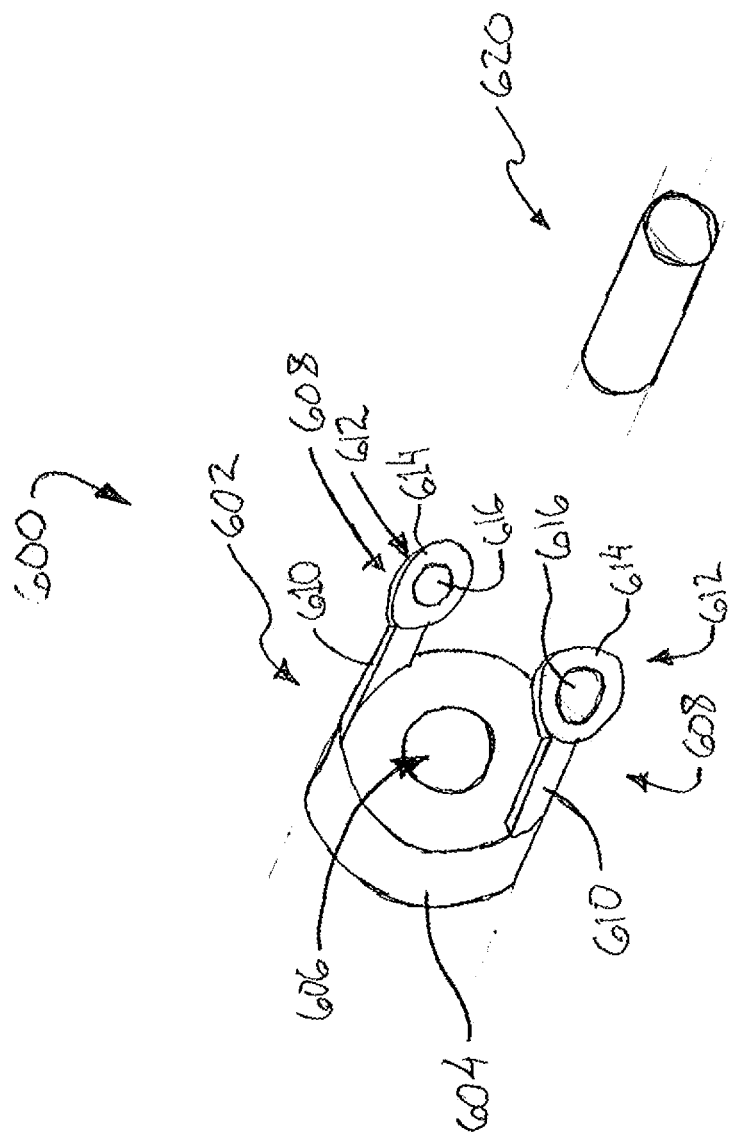
FIG. 4 depicts a perspective view of a mechanical tissue manipulation assembly that may be readily used with the biopsy system of FIG. 1.
Figure 5:
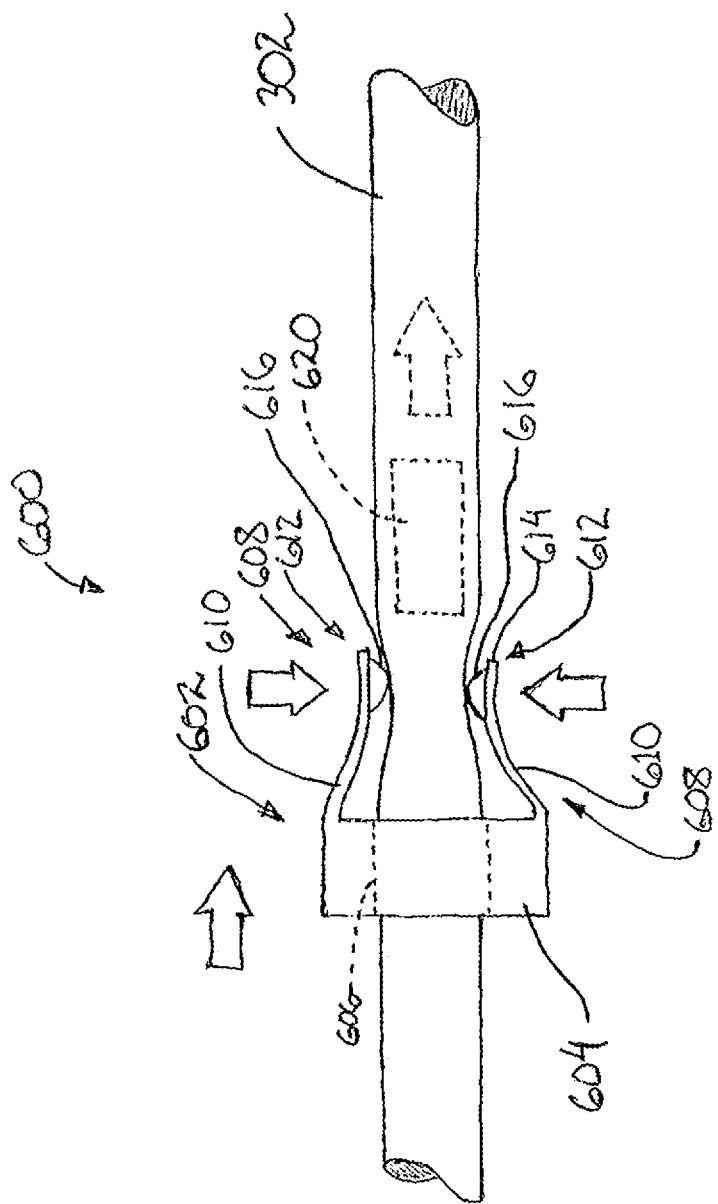
FIG. 5 depicts a front elevational view of the mechanical tissue manipulation assembly of FIG. 4 being used with a tissue transport tube of the biopsy system of FIG. 1.

FIGS. 4 and 5 show a mechanical tissue manipulation assembly (600) for use with tissue transport tube (302) described above. As will be described in greater detail below, mechanical tissue manipulation assembly (600) is generally configured to manually manipulate tissue samples through tissue transport tube (302) through compression of the exterior of tissue transport tube (302). Mechanical tissue manipulation assembly (600) includes a tube compressor (602) and a manipulation pin (620). Tube compressor (602) includes a cylindrical tube receiver (604) and a pair of compression arms (608). Tube receiver (604) defines a cylindrical bore (606) extending axially through tube compressor (602). Cylindrical bore (606) is sized to be at least greater than the outer diameter of tissue transport tube (302). Thus, it should be understood that bore (606) is configured to receive tissue transport tube (302) to permit tissue receiver (604) to freely translate axially along the exterior of tissue transport tube (302).

Compression arms (608) extend axially away from tube receiver (604). Each compression arm (608) includes a resilient portion (610) and a compression portion (612). Resilient portion (610) of each compression arm (608) is generally configured with sufficient stiffness to be resiliently biased towards a relaxed position shown in FIG. 4. Yet, resilient portion (610) of each compression arm (608) is also configured to be sufficiently flexible to bend towards a compression position as shown in FIG. 5. As will be described in greater detail below, this configuration of resilient portion (610) generally permits an operator to manipulate compression portion (612) of each compression arm (608) toward tissue transport tube (302).

Compression portion (612) of each compression arm (608) is generally configured to bend or flex tissue transport tube (302) into a compressed position, as will be described in greater detail below. Compression portion (612) of each compression arm (608) includes a generally cylindrical-shaped body portion (614) with a generally hemispherical indentation (616) disposed within the center of body portion (614). As will be understood, indentation (616) is generally configured to engage tissue transport tube (302) to compress tissue transport tube (302) while gliding along the exterior of tissue transport tube (302). In addition, the hemispherical shape of indentation (616) provides exterior surface on body portion (614) that is more readily griped by an operator. Although each compression portion (612) of the present example is shown as including indentation (616) with a hemispherical geometry, it should be understood that in other examples numerous alternative geometries may be used. For instance, in some examples, each compression portion (612) may include a triangular, semi-oval, or tear drop shape. Alternatively, in some examples, the generally solid shape of compression portion (612) may be omitted in favor of other suitable components such as roller assemblies, wheel assemblies, or ball bearing assemblies. Of course, other suitable configurations for each compression portion (612) will be apparent to those of ordinary skill in the art in view of the teachings herein.

Manipulation pin (620) is generally configured to fit within the inner diameter of tissue transport tube (302) such that manipulation pin (620) can freely slide within tissue transport tube (302). Thus, manipulation pin (620) comprises a generally cylindrical shape with a diameter that is smaller than the inner diameter of tissue transport tube (302). As will be described in greater detail below, this configuration permits manipulation pin (620) to be driven through tissue transport tube (302) by tube compressor (602) to manually actuate tissue samples through tissue transport tube (302). Manipulation pin (620) can be constructed of a plurality of suitable materials such as metal, plastic, rubber, and/or etc. However, regardless of the particular material, it should be understood that manipulation pin (620) is generally biocompatible so as to avoid any unnecessary interaction with tissue. Although not shown, it should be understood that in some examples manipulation pin (620) is coated with one or more coatings to enhance the slidability of manipulation pin (620) within tissue transport tube (302).

Although mechanical tissue manipulation assembly (600) of the present example is shown as including manipulation pin (620), it should be understood that in some examples manipulation pin (620) is omitted. In such examples, tube compressor (602) is used to merely seal off a portion of tissue transport tube (302). As will be described in greater detail below, when manipulation pin (620) is omitted, the sealing action of tube compressor (602) is used to generate positive pressure within tissue transport tube (302) by sliding motion of tube compressor (602) along the axial length of transport tube (302).

An exemplary use of mechanical tissue manipulation assembly (600) is shown in FIG. 5. As can be seen, mechanical tissue manipulation assembly (600) is prepared for manual transport of tissue samples by inserting manipulation pin (620) into tissue transport tube (302) and inserting tissue transport tube (302) through bore (606) of tube compressor (602). Although not shown, it should be understood that to gain access to tissue transport tube (302), an operator may disconnect or otherwise decouple tissue transport tube (302) from the proximal end of biopsy device (10).

Once mechanical tissue manipulation assembly (600) is prepared for use, transport of tissue samples though tissue transport tube (302) may be accomplished by generally driving manipulation pin (620) proximally away from biopsy device (10) and towards tissue handler (310). To drive manipulation pin (620) an operator may grasp compression arms (608) of tube compressor (602) to drive indentations (616) into engagement with tissue transport tube (302). During this operation, it should be understood that an operator generally applies sufficient force to compress the effective inner diameter of tissue transport tube (302) in one direction.

With the effective inner diameter of tissue transport tube (302) reduced in one direction, an operator can drive manipulation pin (620) proximally through tissue transport tube (302) by advancing tube compressor (602). During this stage, an operator also continues to apply pressure to maintain the compressed effective inner diameter of tissue transport tube (302). This causes the interior of tissue transport tube (302) to compress around the distal end of manipulation pin (620) and thereby apply a proximally oriented force to manipulation pin (620). This then causes manipulation pin (620) to slide proximally within tissue transport tube (302) and thereby advance any tissue samples that may be adjacent to manipulation pin (620). Sliding of manipulation pin (620) may proceed in this way until the tissue samples engaged by manipulation pin (620) reach tissue handler (310). Alternatively, in some uses mechanical tissue manipulation assembly (600) may only be used until any tissue samples engaged by manipulation pin (620) begin moving under vacuum induced within tissue transport tube (302).

In another exemplary use, tube compressor (602) is used without manipulation pin (620). In this alternative use, tube compressor (602) is used to generate a pocket of positive pressure behind a tissue sample disposed within tissue transport tube (302). To generate this pocket of positive pressure, tube compressor (602) is used to close the inner diameter of tissue transport tube (302) as similarly described above. However, in this use, tube compressor (602) is used to entirely close the inner diameter of tissue transport tube (302), thereby sealing a portion of tissue transport tube (302).

Once the inner diameter of tissue transport tube (302) is completely closed, tube compressor (602) is then driven axially along the length of tissue transport tube (302) towards the tissue sample disposed within tissue transport tube (302). As tube compressor (602) is driven axially along the length of tissue transport tube (302), tube compressor (602) is held by an operator in the closed position. Thus, by driving tube compressor (602), the seal within tissue transport tube (302) is likewise driven towards the tissue sample. This driving action causes the volume between tube compressor (602) and the tissue sample to progressively shrink. As the volume shrinks, pressure between tube compressor (602) and the tissue sample correspondingly increases. This increase in pressure continues until sufficient force is applied via the pressure to transport the tissue sample through tissue transport tube (302). An operator may then continue to drive tube compressor (602) until the tissue sample is transported to tissue handler (310).

Figure 6:
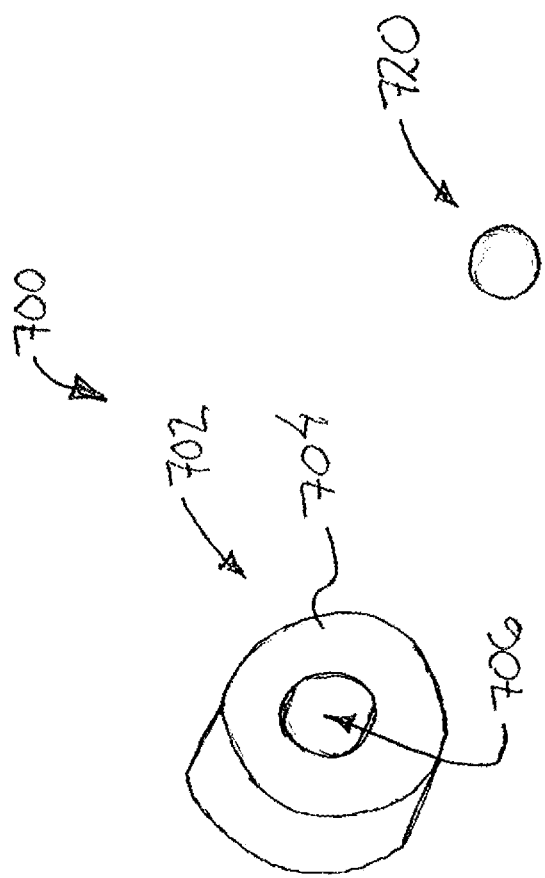
FIG. 6 depicts a perspective view of an alternative mechanical tissue manipulation assembly that may be readily used with the biopsy system of FIG. 1.
Figure 7:
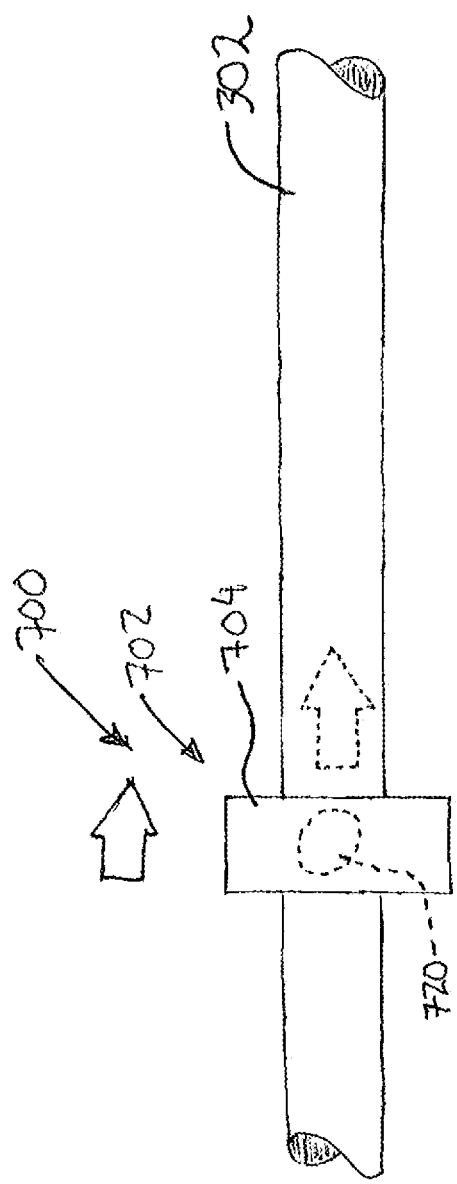
FIG. 7 depicts front elevational view of the mechanical tissue manipulation assembly of FIG. 6 being used with the tissue transport tube of the biopsy system of FIG. 1.

FIGS. 6 and 7 show a magnetic tissue manipulation assembly (700) for use with tissue transport tube (302) described above. Magnetic tissue manipulation assembly (700) is generally similar to mechanical tissue manipulation assembly (600) described above. For instance, and as will be described in greater detail below, as with mechanical tissue manipulation assembly (600), magnetic tissue manipulation assembly (700) is generally configured to manually manipulate tissue samples through tissue transport tube (302). However, instead of manipulating tissue samples through compression of the exterior of tissue transport tube (302), magnetic tissue manipulation assembly (700) uses a magnetic field. Magnetic tissue manipulation assembly (700) includes a manipulator (702) and a spherical traveler (720). Manipulator (702) includes a cylindrical tube receiver (704). Tube receiver (704) defines a cylindrical bore (706) extending axially through manipulator (702). Cylindrical bore (706) is sized to be at least greater than the outer diameter of tissue transport tube (302). Thus, it should be understood that bore (706) is configured to receive tissue transport tube (302) to permit tissue receiver (704) to freely translate axially along the exterior of tissue transport tube (302).

Unlike tube compressor (602) described above, manipulator (702) of the present example omits structures comparable to compression arms (608). Instead, manipulator (702) includes one or more magnets disposed within the interior of manipulator (702) adjacent to bore (706). As will be understood, the magnets disposed within manipulator (702) are configured to produce a magnetic field to permit manipulation of traveler (720) through tissue transport tube (302). Although any suitable number of magnets and any suitable magnet type can be incorporated into manipulator (702), it should be understood that any suitable magnet may provide a sufficient magnetic field to drive traveler (720) through tissue transport tube (302) even in the presence of tissue samples that may resist motion of traveler (720). In some examples this may include neodymium or other strong magnets, although numerous alternative magnets and magnet configurations will be apparent to those of ordinary skill in the art in view of the teachings herein.

Traveler (720) is generally configured to fit within the inner diameter of tissue transport tube (302) such that traveler (720) can freely slide within tissue transport tube (302). Thus, traveler (720) comprises a generally spherical shape with a diameter that is smaller than the inner diameter of tissue transport tube (302). As will be described in greater detail below, this configuration permits traveler (720) to be driven through tissue transport tube (302) by manipulator (702) to manually actuate tissue samples through tissue transport tube (302). In the present example, traveler (720) generally comprises a ferromagnetic material such as ferritic stainless steels, martensitic stainless steels, or other ferromagnetic alloys. However, regardless of the particular material, it should be understood that traveler (720) is generally biocompatible so as to avoid any unnecessary interaction with tissue. Although not shown, it should be understood that in some examples traveler (720) is coated with one or more coatings to enhance the slidability of traveler (720) within tissue transport tube (302).

An exemplary use of magnetic tissue manipulation assembly (700) is shown in FIG. 7. As can be seen, magnetic tissue manipulation assembly (700) is prepared for manual transport of tissue samples by inserting traveler (720) into tissue transport tube (302) and inserting tissue transport tube (302) through bore (706) of manipulator (702). Although not shown, it should be understood that to gain access to tissue transport tube (302), an operator may disconnect or otherwise decouple tissue transport tube (302) from the proximal end of biopsy device (10).

Once magnetic tissue manipulation assembly (700) is prepared for use, transport of tissue samples though tissue transport tube (302) may be accomplished by generally driving traveler (720) proximally away from biopsy device (10) and towards tissue handler (310). To drive traveler (720) an operator may grasp manipulator (702) to move the magnetic field generated by the one or more magnets disposed within manipulator (702) into the space occupied by traveler (720). During this operation, it should be understood that the magnetic field will generally act on traveler (720) to apply a cylindrical force that magnetically secures traveler (720) within bore (706) of manipulator (702).

With traveler (720) secured within bore (706) of manipulator (702), an operator can drive traveler (720) proximally through tissue transport tube (302) by advancing manipulator (702). In particular, movement of manipulator (702) causes the magnetic field within bore (706) to slide traveler (720) proximally within tissue transport tube (302) and thereby advance any tissue samples that may be adjacent to traveler (720). Sliding of traveler (720) may proceed in this way until the tissue samples engaged by traveler (720) reach tissue handler (310). Alternatively, in some uses magnetic tissue manipulation assembly (700) may only be used until any tissue samples engaged by traveler (720) begin moving under vacuum induced within tissue transport tube (302).

Figure 8:
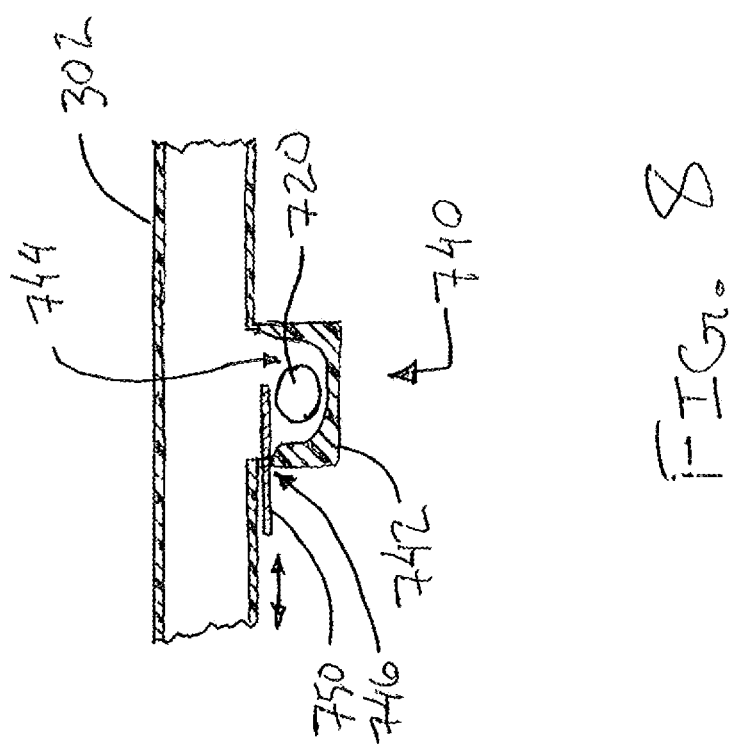
FIG. 8 depicts a side cross-sectional view of a trap that may be readily incorporated into the mechanical tissue manipulation assembly of FIG. 6.

As shown in FIG. 8, in some examples magnetic tissue manipulation assembly (700) may also include a trap (740) that may be incorporated within tissue transport tube (302). Trap (740) is generally configured to contain traveler (720) while magnetic tissue manipulation assembly (700) is not in use. Trap (740) includes a transverse body (742) extending outwardly from tissue transport tube (302) and a retractable cover (750). Body (742) defines a recess (744) in communication with the interior of tissue transport tube (302). Recess (744) is defined by body (742) with a sufficient size to fully contain traveler (720) therein. Thus, it should be understood that when traveler (720) is disposed within recess (744), the interior of tissue transport tube (302) is entirely unobstructed by traveler (720).

Body (742) further defines a cover opening (746). Cover opening (746) is configured to receive retractable cover (750) such that retractable cover (750) can be manipulated by an operator to block and unblock communication between recess (744) and the interior of tissue transport tube (302). Although not shown, it should be understood that in some examples, cover opening (746) may include sealing features to prevent fluid communication into and out of tissue transport tube (302) via trap (740).

Retractable cover (750) generally comprises a rigid solid material that is sized to cover recess (744). Thus, retractable cover (750) is slidable relative to body (742) to open and close recess (744) relative to tissue transport tube (302). Although not shown, it should be understood that in some examples, retractable cover (750) may be curved to match the curvature of tissue transport tube (302). Of course, such a configuration is entirely optional and in some examples retractable cover (750) may have a flat configuration.

In an exemplary use, traveler (720) is generally maintained within recess (744) with retractable cover (750) in a closed duration until use of magnetic tissue manipulation assembly (700) is desired. Once use of magnetic tissue manipulation assembly (700) is desired, retractable cover (750) may be pulled out of cover opening (746) to expose traveler (720) to the interior of tissue transport tube (302). Once traveler (720) is exposed, manipulator (702) may be moved into close proximity with trap (740). Placing manipulator (702) into close proximity with trap (740) causes the magnetic field of manipulator (702) to act on traveler (720). When the magnetic field of manipulator (702) is oriented sufficiently, traveler (720) will be pulled out of recess (744) of trap (740) and into the interior of tissue transport tube (302) for manipulation by manipulator (702) as described above.

In some circumstances, it may be desirable to transport tissue samples in an individual container. For instance, tissue samples generally exhibit a pliable and flexible characteristic rather than being completely solid. Thus, as tissue samples are transported through either cutter (150) within needle (110) or tissue transport tube (302), such tissue samples may change shape. Certain shape changes may make tissue samples more susceptible to creating blockages during transport. For instance, if a tissue sample compresses, the tissue sample's diameter may expand and cause the tissue sample to stick to the interior of tissue transport tube (302). Thus, in some examples it may be desirable to transport tissue samples in an individual container to maintain tissue samples in a consistent shape and thereby prevent blockages.

FIGS. 9 and 10 show an exemplary container (800) that may be used with tissue transport tube (302). Container (800) includes a generally cylindrical outer body (802) and a plurality of sliders (810). Outer body (802) defines a cylindrical shape with a diameter smaller than the inner diameter of tissue transport tube (302) but larger than any tissue sample that may be captured by biopsy device (10). This configuration permits outer body (802) to contain a single tissue sample while sliding freely though tissue transport tube (302). In some examples, outer body (802) comprises a material substantially similar to tissue transport tube (302) such that outer body (802) is generally flexible in correspondence to the flexibility of tissue transport tube (302). This configuration generally permits tissue transport tube (302) to retain flexibility even when container (800) is disposed within tissue transport tube (302). Alternatively, in other examples outer body (802) comprises a material that is generally stiff relative to transport tube (302).

Outer body (802) further defines a loading opening (804). Loading opening (804) is generally size to receive a tissue sample therein. Yet, loading opening (804) is sized to be small enough so that the majority of the surface area of a collected tissue sample is contained within outer body (802). Loading opening (804) is disposed between two closed ends (806) defined by outer body (802) to maintain the axial position of a collected tissue sample within container (800). Although outer body (802) is described herein as being configured for a single tissue sample, it should be understood that in other examples outer body (802) may be configured to receive a plurality of tissue samples. In such examples, outer body (802) may define one or more compartments to store tissue samples discretely. Alternatively, multiple tissue samples may be stored in bulk in single compartment. Of course, various alternative configurations for outer body (802) will be apparent to those of ordinary skill in the art in view of the teachings herein.

The exterior of outer body (802) further includes a plurality of vent openings (809). Vent openings (809) are generally configured to vent the interior of outer body (802) during insertion of a tissue sample into outer body (802). For instance, in some examples the end of outer body (802) opposite to vent openings (809) is generally open to permit axial loading of tissue samples. During axial loading, vent openings (809) provide a pressure release as the tissue sample is inserted into outer body (802). Once the tissue sample is disposed within outer body (802), the tissue sample will seal vent openings (809) to thereby aid transport of container (800) through tissue transport tube (302).

Sliders (810) are disposed on a side of outer body (802) opposite of the side where loading opening (804) is defined. Sliders (810) are generally configured to promote free movement of container (800) within tissue transport tube (802). In the present example, each slider (810) defines a round wheel (812) attached to outer body (802) via an axle (814). Thus, it should be understood that each wheel (812) is generally rotatable to provide enhanced movement of container (800) within tissue transport tube (302). Although sliders (810) of the present example are shown as including wheels (812), it should be understood that in other examples numerous alternative devices to promote movement of outer body (802) may be used. For instance, in some examples, wheels (812) may be replaced with ball bearing rollers, cylindrical rollers, low friction sliders, and/or etc. In still other examples, sliders (810) may be omitted entirely. In such examples, outer body (802) may include a low friction coating to promote slidability of outer body (802) through tissue transport tube (302).

An exemplary use of container (800) is shown in FIG. 10. Initially, container (800) may be loaded by inserting a tissue sample into container (800) through opening in outer body (802). Although not shown, it should be understood that in some examples container (800) is loaded via an automatic loading mechanism. In such examples, the loading mechanism may be incorporated into biopsy device (10) or may be a separate component from biopsy device (10). Alternatively, in other examples container (800) may be loaded manually and then deposited within tissue transport tube (302) for transport to tissue handler (810). Regardless of how tissue samples are loaded into container (800), container (800) is subsequently transported through tissue transport tube (302) once a tissue sample is loaded therein. Once container (800) reaches tissue handler (310), the transported tissue sample may be unloaded and deposited within sample tray (350) of tissue handler (310).

FIG. 11 depicts an alternative transport mechanism (900) that may be used in lieu of container (800) described above. Transport mechanism (900) is generally configured to mechanically transport tissue samples through tissue transport tube (302) in addition or in lieu of transport provided by vacuum induced within tissue transport tube (302). Transport mechanism (900) includes a rotatable auger (902) disposed axially within tissue transport tube (302). Rotatable auger (902) includes a central shaft (904) and helical fins (906) oriented around central shaft (904). Although central shaft (904) and helical fins (906) are shown as comprising a single integral part in the present example, it should be understood that in other examples central shaft (904) and helical fins (906) may be discrete components. Central shaft (904) and helical fins (906) comprise a generally flexible material. Flexibility of central shaft (904) and helical fins (906) generally permits tissue transport tube (302) to retain at least some flexibility even with auger (902) disposed within tissue transport tube (302). In some examples, the flexibility of central shaft (904) and helical fins (906) are approximately equivalent to tissue transport tube (302) such that no loss in flexibility of tissue transport tube (302) is encountered due to the presence of auger (902). In other examples, central shaft (904) and helical fins (906) are less flexible relative to tissue transport tube (302) such that tissue transport tube (302) increases in stiffness when auger (902) is present within tissue transport tube (302).

Central shaft (904) and helical fins (906) are generally configured to accommodate tissue samples within the space defined between helical fins (906). In particular, central shaft (904) defines an outer diameter that is generally small enough relative to the inner diameter of tissue transport tube (302) to accommodate a tissue sample between central shaft (904) and the inner diameter of tissue transport tube (302). Likewise, helical fins (906) are separated by an axial distance that is sufficient to receive the length of a severed tissue sample between each helical fin (906). Although not shown, it should be understood that in some examples tissue transport tube (302) may be resized to accommodate auger (902). For instance, in examples without auger (902), tissue transport tube (302) is generally sized with an inner diameter approximately equivalent to the diameter of tissue samples that are collected via needle (110). Thus, in examples without auger (902), the entire inner diameter of tissue transport tube (302) is generally occupied by any tissue sample being transported. Accordingly, in examples where auger (902) is included, tissue transport tube (302) may be resized to accommodate the additional space occupied by auger (902).

In an exemplary use, auger (902) is generally rotated to transport tissue samples through tissue transport tube (302) in a proximal or distal direction depending on the direction of rotation. In particular, central shaft (904) is rotated to drive rotation of helical fins (906). Due to the helical structure of helical fins (906), each revolution of each helical fin (906) will exert an axial force on a tissue sample received between helical fins (906). This axial force drives the tissue sample received between helical fins (906) proximally or distally depending on the direction of rotation of central shaft (904). Although not shown, it should be understood that in the present example central shaft (904) is coupled to a rotation mechanism that provides selective rotation to central shaft (904). A variety of rotation mechanisms may be used. For instance, in some examples central shaft (904) is coupled to an electric or pneumatic motor via a drive shaft or a plurality of shafts and a plurality of gears. Alternatively, in some examples central shaft (904) is coupled to a manual rotation mechanism to permit manual rotation of central shaft (904). In all examples, the rotation mechanism may be located in any desirable location. By way of example only, suitable rotation mechanism positions may include within biopsy device (10), adjacent to biopsy device (10), within tissue handler (310), adjacent to tissue handler (310), or intermediately along the axial length of tissue transport tube (302).

FIG. 12 depicts another alternative transport mechanism (1000) that may be used in lieu of container (800) described above. Transport mechanism (1000) is generally configured to mechanically transport tissue samples through tissue transport tube (302) in addition or in lieu of transport provided by vacuum induced within tissue transport tube (302). Transport mechanism (1000) includes a conveyer assembly (1002) tissue transport tube (302). Conveyer assembly (1002) includes a transport belt (1004) and a plurality of rollers (1008). Transport belt (1004) is generally configured to ride over rollers (1006) to transport tissue samples through tissue transport tube (302). Rollers (1008) are aligned in an axial side-to-side pattern to permit belt (1004) to define a flat transport surface (1006).

In the present example, rollers (1008) are coupled to each other by a flexible coupling (not shown). Thus, it should be understood that conveyor (1002) of the present example may exhibit at least some flexibility. In addition, in some examples, rollers (1008) may also be flexible to add to the flexibility of conveyor (1002). Because of this flexibility, flexibility of tissue transport tube (302) equipped with conveyor (1002) is generally comparable to versions of tissue transport tube (302) without conveyor (1002). By contrast, in some examples conveyor (1002) may be generally rigid. In such examples, tissue transport tube (302) may be correspondingly rigid.

Transport surface (1006) includes a width defined by the width of belt (1004) and rollers (1008). This width is generally sized to support a tissue sample on transport surface (1006). Accordingly, although a specific width is shown in FIG. 12, it should be understood that various alternative widths may be used. In the present example, the width of transport surface (1006) is generally wider than the inner diameter of tissue transport tube (302) described in the context of other embodiments herein. Accordingly, in the present example, tissue transport tube (302) is modified to provide an increased width to accommodate the width of transport surface (1006). It should be understood that modification of tissue transport tube (302) may generally correspond to the width of transport surface (1006) such that increased or decreased width of transport surface (1006) will result in a corresponding increase or decrease in the width of tissue transport tube (302).

In an exemplary use, one or more rollers (1008) rotate to move belt (1004) along rollers (1008) proximally or distally depending on the direction of rotation of any rotating rollers (1008). Tissue samples collected by needle (110) are deposited on transport surface (1006) and are transported through tissue transport tube (302) as belt (1004) is moved along rollers (1008). Although not shown, it should be understood that conveyor (1002) of the present example includes a rotation mechanism that provides selective rotation of one or more rollers (1008). A variety of rotation mechanisms may be used. For instance, in some examples at least one roller (1008) is coupled to an electric or pneumatic motor via a drive shaft or a plurality of shafts and a plurality of gears. Alternatively, in some examples at least one roller (1008) is coupled to a manual rotation mechanism to permit manual rotation of the at least one roller (1008). In all examples, the rotation mechanism may be located in any desirable location. By way of example only, suitable rotation mechanism positions may include within biopsy device (10), adjacent to biopsy device (10), within tissue handler (310), adjacent to tissue handler (310), or intermediately along the axial length of tissue transport tube (302).

In some circumstances, it may be desirable to supplement tissue transport provided by vacuum through tissue transport tube (302) by providing additional positive fluid pressure on an end of a transported tissue sample opposite of an end subjected to vacuum. As described above, vacuum based tissue transport mechanisms generally rely on a pressure differential between sides of a tissue sample being transported through tissue transport tube (302). For instance, when vacuum is applied to one side of a transported tissue sample and atmospheric air is applied to another side of the transported tissue sample, a net force on the tissue sample results and the tissue sample is propelled towards the vacuum. Without this pressure differential, the transported tissue sample cannot be propelled because no net force is generated on the transported tissue sample. In some circumstances, a pressure differential may exist, but the pressure differential may not generate a net force sufficient to transport a tissue sample. To increase this net force, vacuum pressure may be increased. In addition, or in alterative to increasing vacuum pressure, positive pressure may also be applied to the opposite side of the transported tissue. Thus, it may be desirable to provide various methods and devices to supply positive pressure to tissue transport tube (302).

In other circumstances, vacuum on one side of a transported tissue sample and atmospheric air on another side of the transported tissue sample may be sufficient to transport the tissue sample initially. However, as the tissue sample is transported, additional volume generated through movement of the tissue sample on the atmospheric side on the transported tissue sample may create negative pressure due to insufficient ventilation. This may result in movement of the tissue sample being impeded or prevented entirely. Thus, in some circumstances it may also be desirable to provide various methods and devices to supply supplemental ventilation to tissue transport tube (302). Various illustrative examples of methods and devices to provide supplemental positive pressure and/or ventilation to tissue transport tube (302) are described below. Although particular methods and devices are described below, it should be understood that various alternative methods and devices will be apparent to those of ordinary skill in the art in view of the teachings herein.

Figure 13:
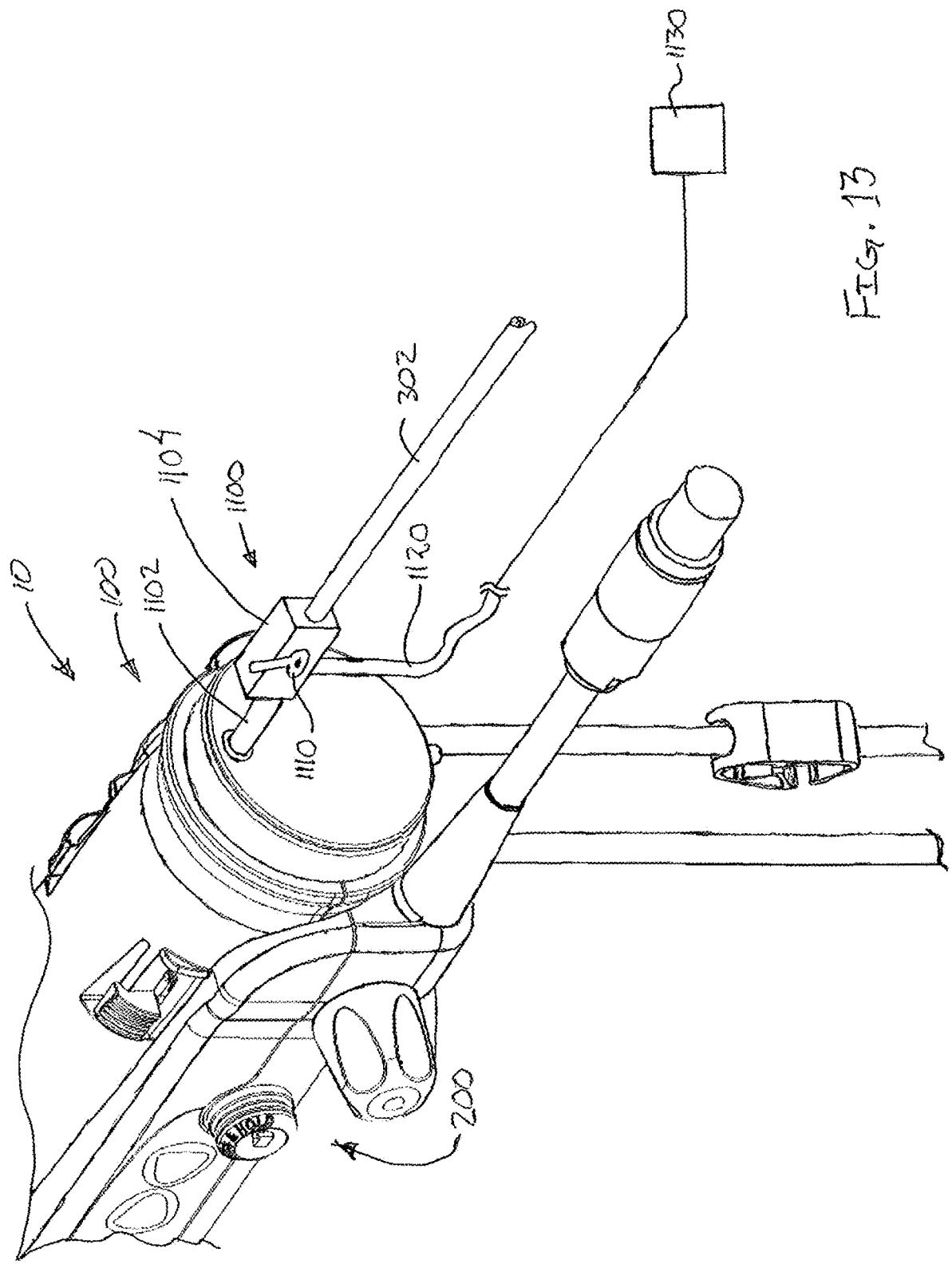
FIG. 13 depicts a perspective view of a transport valve incorporated into the biopsy system of FIG. 1.

FIG. 13 shows biopsy device (10) equipped with an exemplary supplemental transport valve (1100). Transport valve (1100) is generally configured to selectively supply tissue transport tube (302) with supplemental fluid to promote transport of tissue samples through tissue transport tube (302). Transport valve (1100) is coupled to biopsy device (10) via intermediate tube (1102). Although not shown, it should be understood that intermediate tube (1102) extends distally from transport valve (1100) into biopsy device (10) to place intermediate tube (1102) into communication with cutter (150). Thus, it should be understood that tissue samples may be transported through intermediate tube (1102) and into transport valve (1100) prior to being transported through tissue transport tube (302).

Transport valve (1100) includes a valve body (1104), a selector (1110), and a supplemental fluid tube (1120). Valve body (1104) houses various valve components to change the fluid state of transport valve (1100) between a tissue collection state and a tissue transport state, as will be described in greater detail below. Although not shown, it should be understood that the valve components within valve body (1104) are only configured to permit the positive flow of fluid through supplemental fluid tube (1120) and into tissue transport tube (302); and through intermediate tube (1102) and into tissue transport tube (302). Thus, it should be understood that the valve components within valve body (1104) prevent the positive flow of fluid through supplemental fluid tube (1120) and into intermediate fluid tube (1102). This configuration prevents positive fluid from being communicated into the cutter (150) and into a patient.

Selector (1110) is disposed on a side of valve body (1104). Selector (1110) is generally configured to permit manual actuation of transport valve (1100) between the tissue collection state and the tissue transport state. Although the present example uses manual actuation to change the fluid state of transport valve (1100), it should be understood that in other examples selector (1110) may be replaced with an electronic or pneumatically based actuator. In such examples, actuation of transport valve (1100) may be controlled remotely by vacuum control module (400) based on pre-programed control algorithms.

Supplemental fluid tube (1120) extends from valve body (1104) to a supplemental fluid source (1130). When transport valve (1100) is transitioned to the tissue transport state via selector (1110), supplemental fluid tube (1120) is in communication with tissue transport tube (302) such that fluid may flow from supplemental fluid source (1130) and into tissue transport tube (302). By contrast, when transport valve (1100) is transitioned to the tissue collection state via selector (1110), supplemental fluid tube (1120) is closed and is in communication with neither tissue transport tube (302) nor intermediate tube (1102).

Supplemental fluid source (1130) of the present example comprises a pressure pump or air compressor. Thus, it should be understood that supplemental fluid tube (1120) is configured to communicate pressurized fluid into tissue transport tube (302) when transport valve (1100) is in the transport state. Supplemental fluid source (1130) is configured to communicate a variety of fluids to tissue transport tube (302) via supplemental fluid tube (1120). For instance, in the present example supplemental fluid source (1130) is configured to communicate air and/or saline. In other examples, any other suitable fluid may be communicated using supplemental fluid source (1130) in addition or in alternative to air and/or saline. By way of example only, suitable fluids that may be communicated by supplemental fluid source (1130) may include anticoagulants, lubricants, tissue stabilizers, and/or etc. Regardless of the fluids communicated via supplemental fluid source (1130), it should be understood that the particular fluid communicated may be delivered under a variety of pressures. For instance, in the present example the communicated fluid is at a pressure at least comparable to the positive pressure inverse of the vacuum delivered to tissues transport tube (302) (e.g., −40 PSI vacuum and 40 psi pressure). In other examples, the communicated fluid is at a pressure below the positive pressure inverse of the vacuum delivered to tissue transport tube (302). In yet other examples, the fluid is entirely unpressurized and supplemental fluid source (1130) simply serves to provide supplemental venting to tissue transport tube (302). In still other examples, the fluid from supplemental fluid source (1130) is modulated in pressure as a function of time. For instance, supplemental fluid source (1130) may be configured to oscillate or pulse the pressure of fluid delivered to tissue transport tube (302). Such oscillations or pulses may involve alternating between low and high pressure and/or between negative and positive pressure. In some instances, pressure differentiation as a function of time may be used to clear blocked tissue samples from tissue transport tube (302).

In the present example, supplemental fluid source (1130) is connected directly to supplemental fluid tube (1120). However, it should be understood that in other examples supplemental fluid tube (1120) is coupled to supplemental fluid source (1130) by a standard luer fitting or other coupling assembly. In such examples, the luer fitting may be desirable to permit an operator to selectively attach a plurality of different supplemental fluid sources (1130) to supplemental fluid tube (1120). For instance, if supplemental fluid source (1130) comprises a preloaded syringe, an operator may use luer fitting to successively swap a plurality of preloaded syringes. This may permit an operator to very pressure amounts, mediums, and/or volumes as needed.

Although supplemental fluid source (1130) is shown separately from biopsy device (10) and other components of biopsy system (2), it should be understood that in some examples supplemental fluid source (1130) may be readily incorporated into any component of biopsy system (2). For instance, in some examples supplemental fluid source (1130) is incorporated into vacuum control module (400). In yet other examples, supplemental fluid source (1130) is incorporated into biopsy device (10). Still in other examples, supplemental fluid source (1130) is incorporated into valve body (1104) of supplemental transport valve (1100). Still in other examples, supplemental fluid source (1130) is simply a standalone component. When supplemental fluid source (1130) is configured as a separate component, supplemental fluid source (1130) may take on a variety of forms. For instance, in some examples supplemental fluid source (1130) is preloaded pneumatic syringe. In other examples, supplemental fluid source (1130) is a motor actuated vacuum pump. In yet other examples, supplemental fluid source (1130) is merely a pressure regulator that connects to preexisting procedure room compressed air lines. Of course, various other suitable configurations for supplemental fluid source (1130) will be apparent to those of ordinary skill in the art in view of the teachings herein.

In an exemplary use, transport valve (1100) is initially set to the tissue collection state for acquisition of a tissue sample via needle (110). When in the tissue collection state, vacuum flows through tissue transport tube (302) from vacuum control module (400), into intermediate tube (1120), and into cutter (150) disposed within needle (110). Once a tissue sample is severed by cutter (150) within needle (110), the severed tissue sample is transported through cutter (150) and into tissue transport tube (302) via intermediate tube (1102).

Once the severed tissue sample has past transport valve (1100), an operator may manually actuate selector (1110) to transition transport valve (1100) into the transport state. Alternatively, in examples where selector (1110) is replaced with an electrical or pneumatic actuator, such an actuator may be remotely triggered to transition transport valve (1100) automatically. Where transport valve (1100) is transitioned automatically, such automatic transitioning may occur a predetermined time after cutter (150) is moved through a cutting stroke. Alternatively, in some examples transport valve (1100) may be equipped with a tissue sensor or other switch to indicate passage of a tissue sample into tissue transport tube (302). Such a tissue sensor may be used by vacuum control module (400) to identify when to transition transport valve (1100) to the transport state.

Once transport valve (1100) is transitioned to the transport state, supplemental fluid tube (1120) may communicate fluid from supplemental fluid source (1130) and into tissue transport tube (302) via supplemental fluid tube (1120). Thus, when in the transportation state, transport valve (1100) generally provides back pressure to the severed tissue sample to provide additional force to propel the severed tissue sample though tissue transport tube (302). In addition, or in the alternative, transport valve (1100) may provide lubrication, pulsed pressure, supplemental ventilation, and/or other fluid configurations to further support transportation through tissue transport tube (302).

Once the severed tissue sample is transported to tissue handler (310) through tissue transport tube (302), transport valve (1100) may be transitioned back to the tissue collection state using the procedure described above. The process may then be repeated again as necessary until all desired tissue samples are collected into tissue handler (310).

Figure 14:
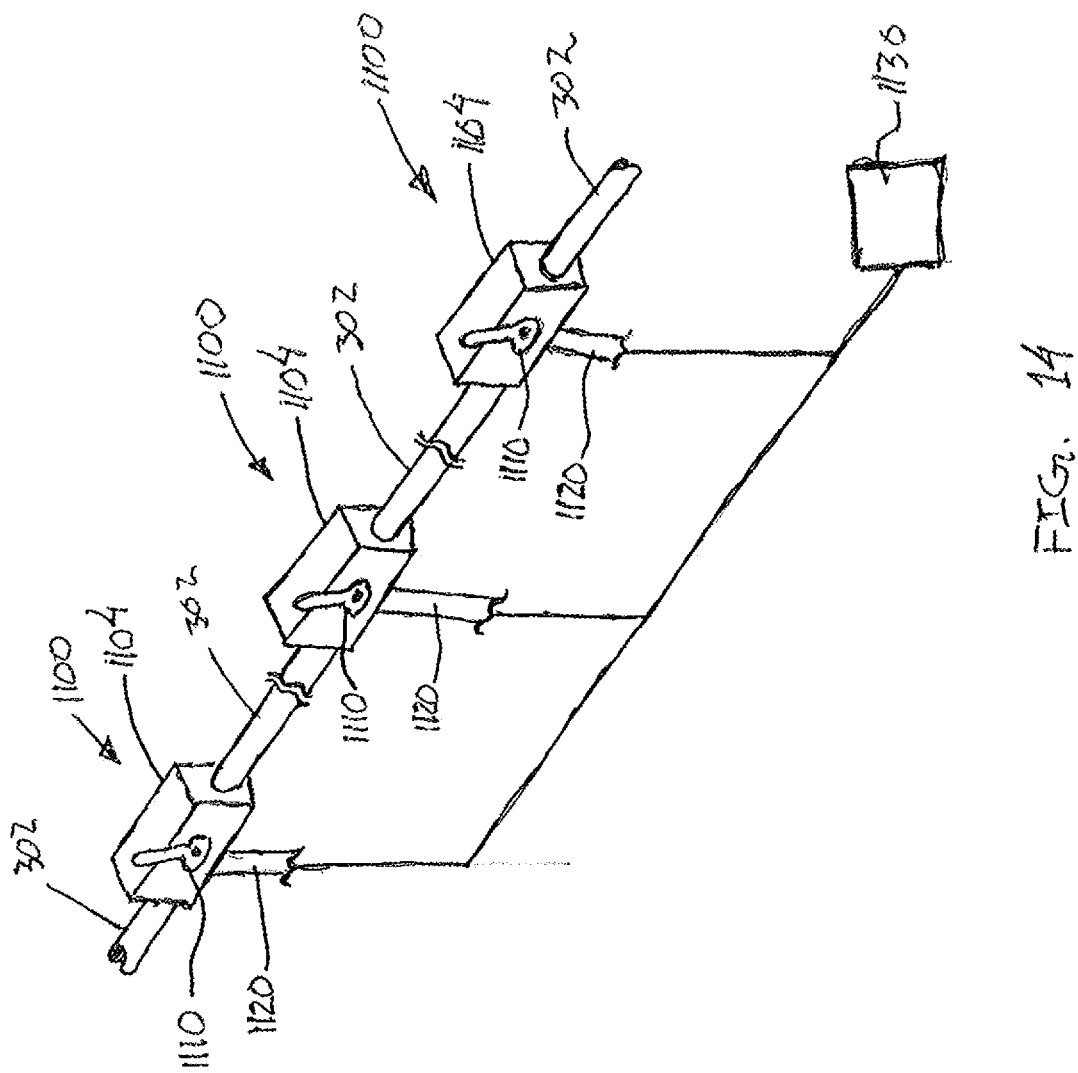
FIG. 14 depicts a perspective view of an alternative configuration of the transport valve of FIG. 13, with a plurality of transport valves in a series configuration.

FIG. 14 shows an alternative configuration for transport valve (1100) described above. In particular, in the present example a plurality of transport valves (1100) are incorporated into tissue transport tube (302). Each transport valve (1100) is substantially the same as described above. For instance, each transport valve (1100) includes, valve body (1104), selector (1110), and supplemental fluid tube (1120). In this configuration, transport valves (1100) divide tissue transport tube (302) into a plurality of discrete transport segments. In some circumstances, this configuration may be desirable to improve tissue sample transport by providing a more direct path for back pressure on a transported tissue sample.

Although the present example shows each transport valve (1100) as being coupled to a single supplemental fluid source (1130) via supplemental fluid tube (1120), it should be understood that in some examples each transport valve (1100) may be coupled to a discrete supplemental fluid source (1130). This configuration may permit each transport valve (1100) may supply a different fluid medium to tissue transport tube (302). This configuration may permit the specific fluid supplied to tissue transport tube (302) to be varied along the length of tissue transport tube (302).

In an exemplary use the plurality transport valve (1100) configuration is used substantially the same as the single transport valve (1100) configuration described above. For instance, all transport valves (1100) are initially transitioned to the tissue collection state. This permits vacuum to flow entirely through tissue transport tube (302) to initially transport a severed tissue sample through cutter (150) and into tissue transport tube (302).

Once a severed tissue sample is within tissue transport tube (302), each transport valve (1100) is sequentially transitioned to the transport state as the severed tissue sample passes a particular transport valve (1100). As a severed tissue sample is transported through transport tube (302), transport valves (1100) continue to be sequentially transitioned to the transport state until the severed tissue sample has passed through the final transport valve (1100) and is deposited within tissue handler (310).

Figure 15:
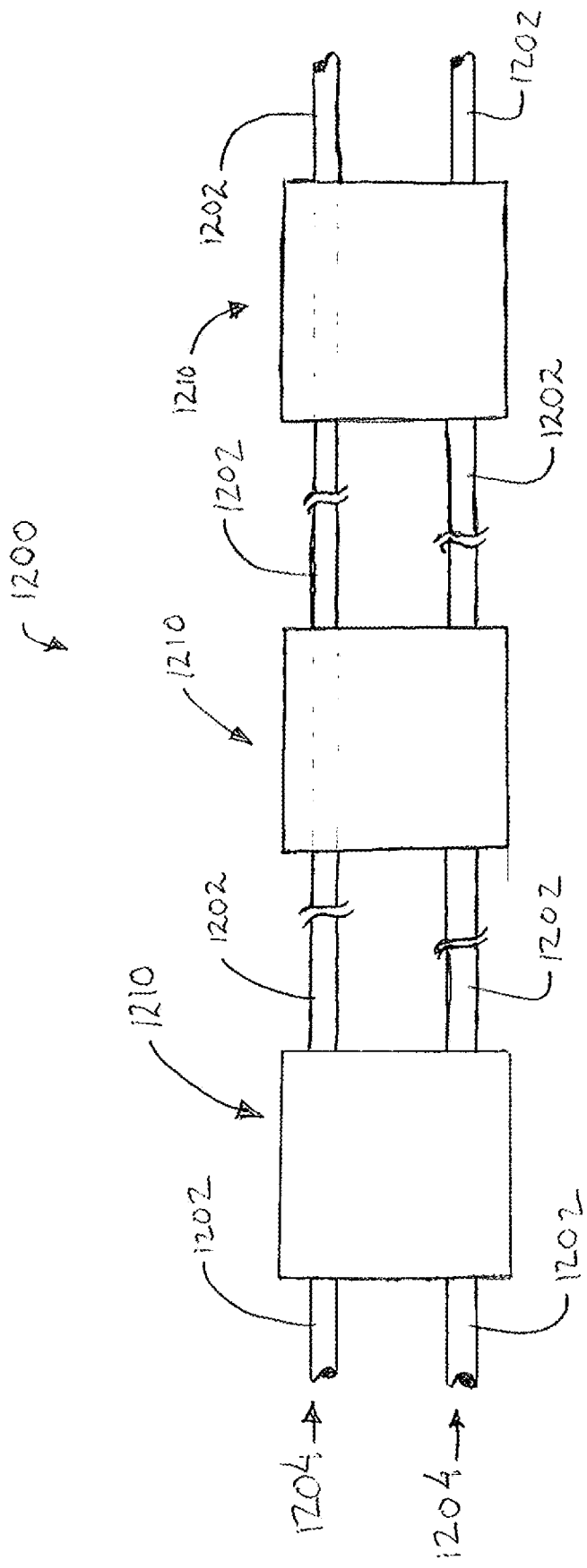
FIG. 15 depicts a front elevational view of a multi-tube tissue transport assembly that may be readily incorporated into the biopsy system of FIG. 1.

FIG. 15 shows an exemplary multi-tube tissue transport assembly (1200) that may be used in biopsy system (2) described above in lieu of tissue transport tube (302). Tissue transport assembly (1200) combines elements of tissue transport tube (302) and transport valve (1100) described above to improve the transport of tissue samples from biopsy device (10) to tissue handler (310). Tissue transport assembly (1200) includes a plurality of transport tubes (1202) extending between a plurality of redirector elements (1210). Each transport tube (1202) is substantially similar to tissue transport tube (302) described above. For instance, each transport tube (1202) comprises a flexible and hollow structure. In addition, each transport tube (1202) is sized to receive a tissue sample severed by the cutter (150). Transport tubes (1202) are arranged to form two parallel transport paths (1204). As will be described in greater detail below, each transport path (1204) is generally configured to permit passage of a severed tissue sample through a linear path. However, as will also be described in greater detail below, each redirector element (1210) is configured to permit an operator to selectively switch a given tissue sample from one transport path (1204) to another transport path (1204). Accordingly, it should be understood that tissue transport assembly (1200) is configured to enhance transport of tissue samples by permitting an operator to switch between tissue paths (1204). Such tissue path (1204) switching may be desirable to avoid blockages in any one transport tube (1202) without having to clear the blockage.

Figure 16:
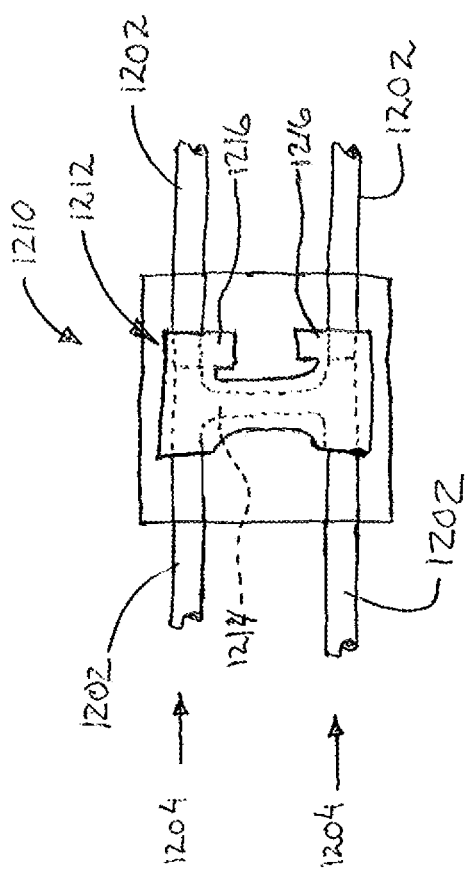
FIG. 16 depicts a front elevational view of a redirector element of the multi-tube tissue transport assembly of FIG. 15.

FIG. 16 shows a single redirector element (1210) in greater detail. Although only a single redirector element (1210) is shown, it should be understood that all redirector elements (1210) are substantially similar to the one shown in FIG. 16. As can be seen, redirector element (1210) includes a tube coupler (1212) and a pair of gates (1216). Tube coupler (1212) extends perpendicularly between two transport tubes (1202) extending in parallel through redirector element (1210). Within tube coupler (1212) a coupler lumen (1214) is defined by tube coupler (1212). Coupler lumen (1214) is generally sized to receive severed tissue samples. It should be understood that in this configuration, tube coupler (1212) is configured to permit tissue samples and/or fluid to transfer between transport paths (1204) defined by the parallel transport tubes (1202) via coupler lumen (1214).

Each gate (1216) is positioned to block each respective transport path (1204) defined by transport tubes (1202). As will be understood, each gate (1216) is generally configured to selectively open and close a corresponding transport tube (1202) to provide selective transfer of tissue samples and/or fluid between two parallel transport paths (1204). Thus, each gate (1216) is configured to transition between an open configuration and a closed configuration. When gate (1216) is in the closed configuration, coupler lumen (1214) is in communication between transport paths (1214) defined by transport tubes (1202), while one transport tube (1202) is blocked. Thus, the closed configuration of gate (1216) corresponds to redirector element (1210) being configured to transport tissue samples and/or fluid between transport paths (1204). Similarly, when gate (1216) is in the open configuration, the transport tube (1202) associated with a desired transport path (1204) is in open communication. In some examples, coupler lumen (1214) is also blocked such that communication between transport paths (1214) defined by transport tubes (1202) is generally eliminated. Thus, the open configuration of gate (1216) corresponds to redirector element (1210) being configured to maintain tissue samples and/or fluid on a specific transport path (1204).

Although not shown, it should be understood that gates (1216) may take on a variety of forms. For instance, in some examples each gate (1216) comprises a variety of mechanical valves. By way of example only, suitable valves of each gate (1216) may include a butterfly valve, a gate valve, a ball valve, a swing valve, a diaphragm valve, or etc. Alternatively, each gate (1216) may include a variety of mechanical or pneumatic gate mechanisms. By way of example only, suitable gate mechanisms may include retractable door mechanism, flexible diaphragm mechanisms, or etc. Regardless of the particular configuration of each gate (1216), it should be understood that gate (1216) may be actuated in a variety of ways. For instance, in some examples each gate (1216) is manually actuated by a lever, push button, thumbwheel, or other mechanical activation mechanism. In other examples, each gate (1216) is actuated by a motor or pneumatically mechanism. In examples where each gate (1216) is activated by a motor or pneumatically driven mechanism, it should be understood that such mechanisms may be used to activate each gate (1216) remotely. For instance, in such examples vacuum control module (400) may permit an operator to remotely actuate each gate (1216) as a part of a control algorithm that uses one or more redirector elements (1210) along with other functional features (e.g., vacuum pulsing, sequential pressure/vacuum switching, etc.) to aid in the transport of tissue samples from biopsy device (10) to tissue handler (310). Of course, numerous alternative configurations for redirector element (1210) will be apparent to those of ordinary skill in the art in view of the teachings herein.

In an exemplary use of multi-tube tissue transport assembly (1200), tissue samples are transported from biopsy device (10) to tissue handler (310) as similarly described above with respect to tissue transport tube (302). For instance, under some circumstances, tissue samples may travel from biopsy device (10) to tissue handler (310) entirely within a single transport path (1204). During these circumstances, gate (1216) within each redirector element (1210) is in the open configuration such that no tissue samples are transported between transport paths (1204).

However, under some circumstances, one or more tissue samples may become lodged within one or more transport tubes (1202), thereby blocking a portion of a single transport path (1204). In such circumstances, it may be desirable to bypass portions of the blocked transport path (1204). Accordingly, in some uses an operator may desire to transport tissue samples between transport paths (1204). To transport tissue samples between transport paths (1204) and thereby effectively bypass portions of a blocked sample path (1204), an operator may actuate a selected gate (1216) ahead of the lodged tissue sample to the closed configuration. With gate (1216) in the closed configuration, the corresponding transport tube (1202) is blocked and coupler lumen (1214) is transitioned into communication between parallel transport tubes (1202). This permits tissue samples to pass between two parallel transport paths (1204), thereby bypassing the lodged tissue sample.

Once a lodged tissue sample has been effectively bypassed using one or more redirector elements (1210), tissue samples may continue through the non-blocked transport path (1204) until reaching tissue handler (310). Alternatively, one transported tissue samples have been transported proximally of the blockage, another redirector element (1210) may be used to return transported tissue samples back to the original transport path (1204). Returning tissue transport to the original transport path (1204) using redirector element (1210) may proceed as similarly described above.

FIGS. 17 and 18 show an alternative transport valve (1300) that is substantially similar to transport valve (1100) described above. As discussed above, transport valve (1100) is generally configured to supply supplemental back pressure to tissue transport tube (302) to thereby promote transportation of tissue samples through tissue transport tube (302). Transport valve (1300) of the present example is similarly configured to supply supplemental back pressure to tissue transport tube (302). However, unlike transport valve (1100), transport valve (1300) of the present example is integrated into at least a portion of biopsy device (10) such as probe (100) and/or holster (200).

As can be seen, transport valve (1300) includes an actuator (1302), a sample lumen (1306), a pressure lumen (1308), and a pressure source (1310). Actuator (1302) comprises a lever arm that is configured to pivot within a portion of biopsy device (10) (e.g., probe (100)). As will be understood, actuator (1302) is generally configured to pivot and thereby transition transport valve (1300) between an open and a closed position. Pivoting of actuator (1302) may be provided by a variety of mechanisms. For instance, in some examples, actuator (1302) is manually pivoted by a lever mechanism, rotation shaft, and/or etc. In other examples, actuator (1302) is pivoted by an electric or pneumatic motor. In examples where a motor is used to pivot actuator (1302), the motor can be controlled remotely via vacuum control module (400). In still other examples, actuator (1302) is configured as a three-way stopcock that is manually, electronically, or pneumatically actuated. Of course, in other examples actuator (1302) is controlled by any other suitable mechanism as will be apparent to those of ordinary skill in the art in view of the teachings herein.

Sample lumen (1306) and pressure lumen (1308) are both defined by a portion of biopsy device (10) (e.g., probe (100) and/or holster (200)) and/or transport valve (1300). Sample lumen (1306) extends between cutter (150) and tissue transport tube (302). Thus, it should be understood that sample lumen (1306) is configured to transport tissue samples from cutter (150) to tissue transport tube (302). Pressure lumen (1308) extends from pressure source (1310) to sample lumen (1306). As will be understood, pressure lumen (1308) is generally configured to communicate pressurized fluid from pressure source (1310) to sample lumen (1306) and into tissue transport tube (302). This configuration permits pressure source (1310) to supply tissue transport tube (302) with supplemental back pressure to assist with transporting tissue samples through tissue transport tube (302).

Pressure source (1310) of the present example comprises an air compressor that can be selectively activated to supply pressurized air to tissue transport tube (302) via pressure lumen (1308). In the present example, pressure source (1310) is shown as being integrated into a portion of biopsy device (10) such holster (200). However, it should be understood that in other examples pressure source (1310) can be readily incorporated into other portions of biopsy device (10) such as probe (100). Alternatively, in still other examples pressure source (1310) can be entirely separate from biopsy device (10) as a standalone part or as a portion of control module (400). Although not shown, it should be understood that pressure source (1310) may include a valve or other component to selectively control delivery of pressurized fluid to pressure lumen (1308). In other examples, a valve or other component is in communication with pressure lumen (1308) at some point between pressure source (1310) and sample lumen (1306). In still other examples, pressure source (1310) is configured to provide selective delivery of pressure by merely being activated and deactivated.

Although pressure source (1310) is described herein as being an air compressor, it should be understood that pressure source (1310) can alternatively comprise a variety of other devices. Additionally, pressure source (1310) may be configured to provide a variety of alternative pressurized fluid mediums in addition or in alternative to air. For instance, in some examples, pressure source (1310) is merely a pressurized fluid reservoir that is configured to provide a finite quantity of pressurized fluid medium. In other examples, pressure source (1310) is configured as a fluid port for the coupling of an external fluid source or vent. In all such examples, the pressurized fluid medium used in pressure source (1310) may be compressed air, compressed inert gas, pressurized saline, and/or etc. Of course, various alternative configurations of pressure source (1310) will be apparent to those of ordinary skill in the art in view of the teachings herein.

Pressure source (1310) is coupled to a controller (1312) or processor. Controller (1312) is generally configured to activate and deactivate pressure source (1310). In addition, or in the alternative, controller (1312) is also in communication with actuator (1302) to transition transport valve (1300) between the open and closed state. Although controller (1312) is depicts in isolation in the present example, it should be understood that controller (1312) may be integrated into a variety of components of biopsy system (2). For instance, in some examples controller (1312) is integrated into vacuum control module (400). In other examples, controller (1312) is integrated into various components of biopsy device (10) such as probe (100) or holster (200). In still other examples, controller (1312) is a discrete unit as shown.

In the present example, controller (1312) is generally configured to selectively activate and deactivate pressure source (1310) to thereby supply fluid to sample lumen (1306) via pressure lumen (1308) at a predetermined level of pressure. However, it should be understood that in some examples, pressure source (1310) can be configured to provide fluid to sample lumen (1306) at a plurality of pressure levels. For instance, in some examples pressure source (1310) can be configured to supply a range of different pressure levels, including negative pressures (e.g., −50 to +50 psi). In such examples, controller (1312) can be configured to modulate the pressure supplied by pressure source (1310) as a function of time. As will be described in greater detail below, this functionality can be used in certain post recovery procedures to aid in dislodging a tissue sample from tissue transport tube (302).

In an exemplary use, transport valve (1300) is initially in a collection configuration shown in FIG. 17. In the collection configuration, actuator (1302) is in an initial position such that at least a portion of actuator (1302) is positioned to permit communication of cutter (150) with tissue transport tube (302) via sample lumen (1306). At this stage, actuator (1302) is also positioned such that at least a portion of actuator (1302) is positioned to block pressure lumen (1308). Thus, actuator (1302) is pivoted to be positioned in a parallel position relative to an axis defined by sample lumen (1306). Accordingly, it should be understood that when transport valve (1300) is in the collection configuration, tissue samples may be transported through sample lumen (1306) and into tissue transport tube (302). To prevent the flow of pressure into cutter (150), it should be understood that pressure source (1310) is not activated at this stage or otherwise prevented from communicating pressure to pressure lumen (1308).

While transport valve (1300) is in the collection configuration, a tissue sample may be severed by cutter (150). The severed tissue sample is then transported through sample lumen (1306) by vacuum communicated through tissue sample tube (302) from vacuum control module (400). Transport of the severed tissue sample through sample lumen (1306) continues in this way until the severed tissue sample reaches tissue transport tube (302).

Once the severed tissue sample arrives at tissue transport tube (302), an operator may desire to provide back pressure on the severed tissue sample to assist with transport of the severed tissue sample through tissue transport tube (302). To provide back pressure on the severed tissue sample, an operator may transition transport valve (1300) from the collection configuration to a transport configuration. FIG. 18 shows transport valve (1300) in the transport configuration. To transition transport valve (1300) to the transport configuration, actuator (1302) is pivoted in a counter clockwise direction to a blocking position. This pivoting action of actuator (1302) repositions actuator (1302) such that actuator (1302) is fully obstructing and sealing sample lumen (1306). With sample lumen (1306) sealed, pressurized fluid is prevented from flowing into cutter (150) via pressure lumen (1308).

With transport valve (1300) transitioned to the transport configuration shown in FIG. 18, pressure source (1310) can now apply pressure to pressure lumen (1308). Pressure source (1310) may be then activated by controller (1312) or otherwise placed into communication with pressure lumen (1308). This causes the pressurized fluid medium described above to flow through pressure lumen (1308) and into tissue transport tube (302). With pressurized fluid applied to the distal end of tissue transport tube (302), a back pressure is applied to the severed tissue sample. This back pressure then assists with transport of the severed tissue sample by increasing the pressure differential between the distal end of the severed tissue sample and the proximal end of the severed tissue sample. Once the severed tissue sample is successfully transported from biopsy device (10) to tissue handler (310), the process described above may be repeated as necessary to acquire additional tissue samples.

The transitioning of transport valve (1300) from the collection configuration to the transport configuration can be triggered in a variety of ways. For instance, in some examples transport valve (1300) can be operated manually. In such examples, an operator can visually identify when it is appropriate to transition transport valve (1300). In other examples, transport valve (1300) is controlled by vacuum control module (400) and/or controller (1312). In such examples, transitioning of transport valve (1300) can be triggered automatically based on certain timing algorithms that can utilize the position of cutter (150) to recognize when a tissue sample is severed, and transport begins. Alternatively, transport valve (1300) can include one or more sensors associated with sample lumen (1306) to recognize when a tissue sample is transported into sample lumen (1306). Based on information from such sensors, transport valve (1300) can be transitioned automatically at the moment the collected tissue sample has been transported proximally past actuator (1302).

In another exemplary alternative use, transport valve (1300) may be operated in a manner similarly described above but in a post recovery procedure. The post recovery procedure may be desirable when a tissue sample becomes lodged within tissue transport tube (302). In particular, in some instances merely providing pressure to the distal end of tissue transport tube (302) via pressure source (1310) may be sufficient to successfully force a blocked tissue sample through tissue transport tube (302). However, in other instances, merely providing pressure via pressure source (1310) may be insufficient to successfully force a blocked tissue sample through tissue transport tube (302). In the later instance, it may therefore be desirable to activate the post recovery procedure. As will be described in greater detail below, the post recovery procedure generally involves applying alternating opposing pressures to a blocked tissue sample to successfully force the blocked tissue sample through tissue transport tube (302).

The presence of a blockage within tissue transport tube (302), is generally identified using vacuum control module. In particular, during the transport of sample through tissue transport tube (302), vacuum control module (400) monitors the output of a vacuum sensor (not shown) for any potential issues in transport. In some examples, this vacuum sensor may be located in vacuum control module (400) or tissue handler (310). If the vacuum output detected by the sensor changes at a rate higher than a threshold level, that may indicate that the sample is slowing down in tissue transport tube (302). If so, vacuum control module (400) may initiate the post recovery procedure automatically. As will be described in greater detail below, this procedure generally involves a cycle of pulsing the vacuum level in tissue transport tube (302) to try and allow the sample to speed up or allow the sample to relax/stretch.

In other examples, another vacuum sensor (not shown) may be disposed within probe (100) to monitor vacuum and/or pressure levels within tissue transport tube (302) from the distal end of tissue transport tube (302). This vacuum sensor associated with probe (100) may be in addition or lieu of the vacuum sensor associated with vacuum control module (400) described above. In this example, the vacuum sensor is coupled with vacuum control module (400) to permit vacuum control module (400) to likewise monitor pressure levels to determine if a transported tissue sample is slowing down or stopping within tissue transport tube (302). By way of example only, this condition may be detected by identifying a pressure change beyond a threshold level. If the transported sample stops completely, the vacuum sensor will generally register a reading of 0 (e.g., atmospheric pressure) or a reading equivalent to the pressure supplied by pressure source (1310) depending on whether pressure source (1310) is active. Thus, in the case of an atmospheric reading, the space within tissue transport tube (302) will be at atmospheric pressure due to any venting occurring between cutter (150) and needle (110). Likewise, in the case of a reading equivalent to the pressure supplied by pressure source (1310), the space within tissue transport tube (302) will be at an equivalent pressure due to said space reaching equilibrium with pressure source (1310). In examples where a sensor is disposed at both ends of tissue transport tube (302) (e.g., vacuum control module (400) and probe (100)), both sensors can be monitored simultaneously by vacuum control module (400) to generally improve the accuracy of detecting a slowing or stopped tissue sample.

Once the slowing or stopping of the sample is detected by monitoring the output of the vacuum sensors, a post recovery procedure is activated immediately, preferably before the sample has had a chance to stop. In some uses an operator may activate the post recovery procedure by selecting a mode of operation corresponding to the post recovery procedure using vacuum control module (400) or a user input feature incorporated into biopsy device (10). Once activated, a control logic within vacuum control module (400) or biopsy device (10) is generally configured to provide a series of signals that control pressure supplied to tissue transport tube (302) via pressure source (1310) (pressure) and/or vacuum control module (400) (vacuum). This series of signals generally results in providing pulsed pressure and/or pulsed vacuum to tissue transport tube (302) in a predetermined sequence. After communicating this pulsed pressure and/or pulsed vacuum to tissue transport tube (302), the blocked tissue sample may become unblocked and the biopsy procedure may proceed as usual. Alternatively, if the blocked tissue sample remains blocked, the post recovery procedure may be repeated as many times as desired to successfully unblock the tissue sample from tissue transport tube (302).

Pressure source (1310) and/or vacuum control module (400) may each be configured to provide a plurality of different pressure and/or vacuum sequences. For instance, in the present example pressure and vacuum is supplied to tissue transport tube (302) in a predetermined pulse sequence. In this pulse sequence, pressure source (1310) is activated to provide pressure to the distal end of tissue transport tube (302) for one second followed by no pressure for 1 second. This sequence is repeated for at least one minute and as long as several minutes. Vacuum control module (400) is likewise activated during this time to provide vacuum to the proximal end of tissue transport tube (302) in a similar sequence of one second on (at the same time when positive pressure source (1310) is on) followed by one second off (at the same time when positive pressure source (1310) is off) for a total period of one or more minutes. Alternatively, the vacuum from vacuum control module (400) is constantly on while the positive pressure source (1310) pulses according to the above sequence. At the conclusion of this pulsing sequence, an extended continuous combination of pressure and vacuum is supplied to tissue transport tube (302). After this, only vacuum is supplied to tissue transport tube (302) to prevent the tissue sample from moving at an uncontrolled rate through tissue transport tube (302). In another example of a pulse sequence, the pulsing is at a rate of at least 5 cycles per second for at least one second (i.e., total of at least 5 cycles). Each on/off switching is counted as one cycle. Depending on the detected condition (e.g., slowing down, stopping, moving slowly, etc.), vacuum control module (400) can be programmed to vary the pulsing rate. For example, the pulsing rate can be at least 10 cycles per second for 1 second, i.e., on for 0.5 second and off for 0.5 second. Regardless of the particular cycle, it should be understood that during the entirety of the cycle, transport valve (1300) is transitioned to the transport state described above to prevent pressure from being communicated into the patient from pressure source (1310).

It should be understood that the particular sequence of pressure and/or vacuum described above may be varied in a number of ways. For instance, in some uses pressure and vacuum is alternated such that a pressure pulse immediately followed by a vacuum pulse. In addition, or in the alternative, the particular pulse time may be adjusted to be more or less than 1 second. Similarly, the recovery period of 10 seconds may be adjusted as desired. Although a consistent pulse pattern is described herein, it should be understood that in other uses, the pulse patter may be varied as a function of time. For instance, as the number of pulses increases, the particular temporal length of each pulse may be increased or decreased. In still other uses, pressure source (1310) and/or vacuum control module (400) may each be configured to provide both pressure and vacuum. Thus, pressure and vacuum may be alternatingly suppled to the distal end of tissue transport tube (302), the proximal end of tissue transport tube (302), or both ends of tissue transport tube (302). Of course, various alternative pulse sequences may be used as will be apparent to those of ordinary skill in the art in view of the teachings herein.

Figure 19:
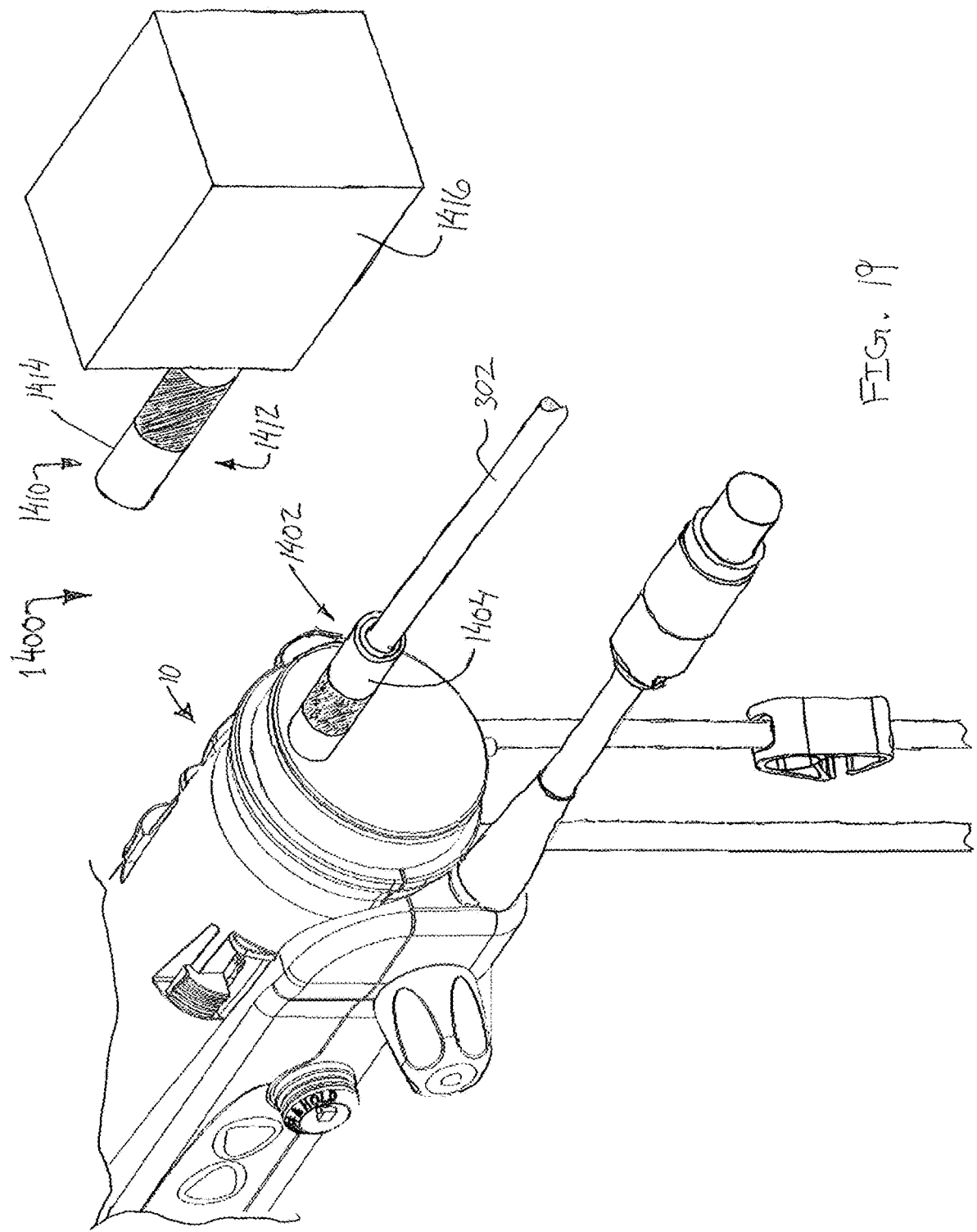
FIG. 19 depicts a perspective view of a quick release pressure assembly that may be readily incorporated into the biopsy system of FIG. 1.

FIG. 19 shows a quick release pressure assembly (1400). Quick release pressure assembly (1400) is generally configured to apply supplemental back pressure to tissue transport tube (302) to assist with transport of tissue samples through tissue transport tube (302). Quick release pressure assembly (1400) comprises a quick release coupling (1402) extending from biopsy device (10) and a pressure source assembly (1410). Quick release coupling (1402) is a ball-bearing based quick release coupler. Generally, quick release coupling (1402) includes an outer sheath (1404) and an inner female receiver (1406). Outer sheath (1404) is translatable relative to inner female receiver (1406) to release a male coupler (1408) that is secured to the distal end of tissue transport tube (302). Similarly, outer sheath (1404) is also translatable relative to inner female receiver (1406) to receive male coupler (1408) and thereby lock male coupler (1408) within inner female receiver (1406) upon release of outer sheath (1404).

Figure 20:
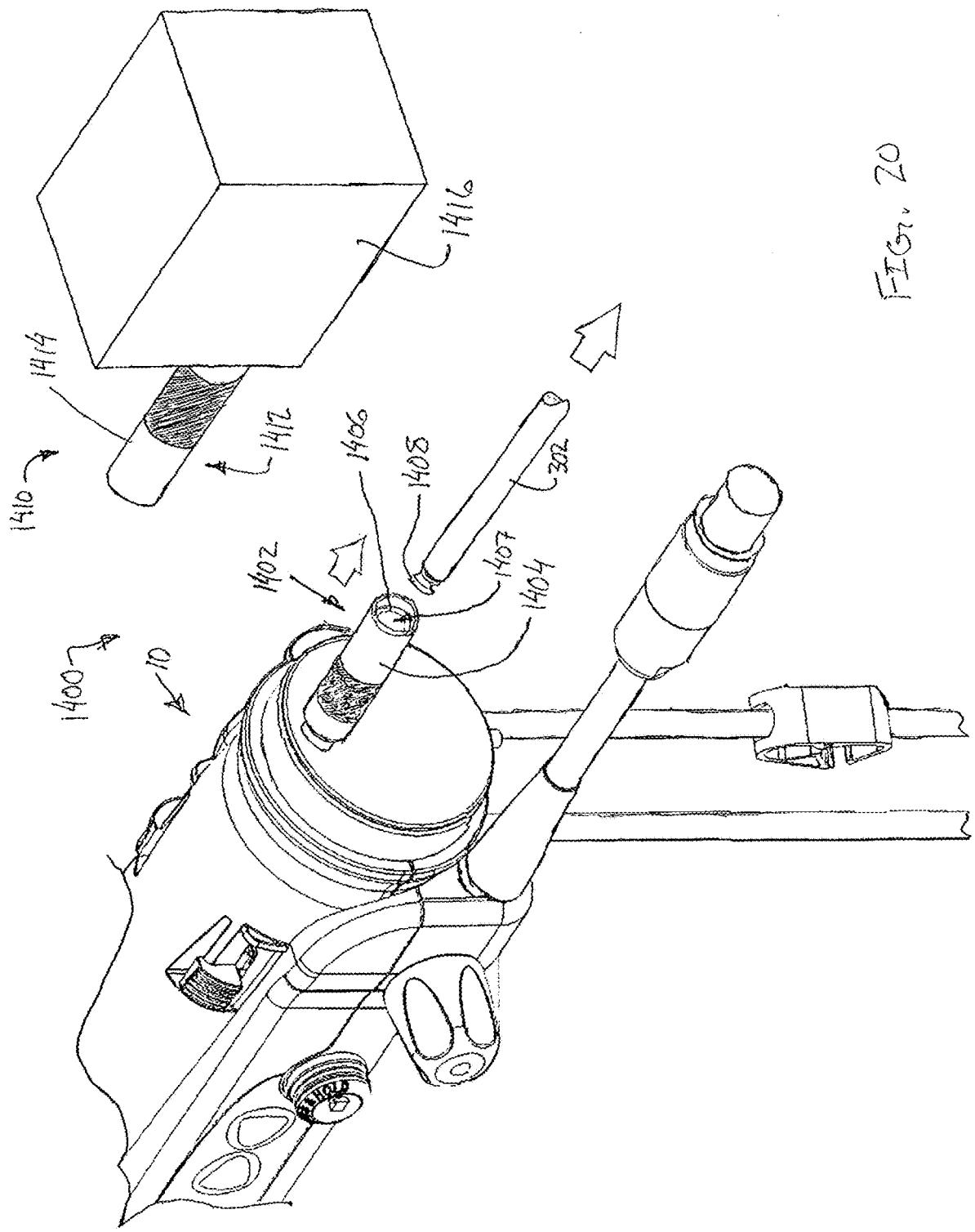
FIG. 20 depicts another perspective view of the quick release pressure assembly of FIG. 19, with the tissue transport tube of the biopsy system of FIG. 1 decoupled from the quick release pressure assembly.

As can best be seen in FIG. 20, inner female receiver (1406) defines a lumen (1407) extending through quick release coupling (1402) and into communication with cutter (150). Thus, it should be understood that quick release coupling (1402) is generally configured to transport tissue samples severed by cutter (150) to tissue transport tube (302) via lumen (1407). Although not shown, it should be understood that in some examples inner female receiver (1406) includes a check valve or other mechanism to close lumen (1407) when tissue transport tube (302) is decoupled from quick release coupling (1402). In examples where inner female receiver (1406) includes a check valve, such a check valve is usable to prevent excess fluid from leaking out of biopsy device (10) via quick release coupling (1402). Of course, this check valve is merely optional and may be omitted in some examples.

Pressure source assembly (1410) is generally configured to provide a pressurized fluid medium to the distal end of tissue transport tube (302). Pressure source assembly (1410) includes a quick release coupling (1412) and a pressure source (1416). Quick release coupling (1412) is substantially the same as quick release coupling (1402) described above. For instance, as with quick release coupling (1402), quick release coupling (1412) is a ball-bearing based quick release coupler that includes an outer sheath (1414) and an inner female receiver (not shown). Outer sheath (1414) is translatable relative to the inner female receiver to receive, lock, and release male coupler (1408). As will be described in greater detail below, quick release coupling (1412) is generally configured to receive tissue transport tube (302) to apply a pressurized fluid medium to the distal end of tissue transport tube (302) from pressure source (1416).

Pressure source (1416) is generally configured to supply a pressurized fluid medium to the distal end of tissue transport tube (302) via quick release coupling (1402). In the present example, pressure source (1416) can communicate any suitable pressurized fluid medium such as pressurized air, saline, or some combination thereof. Alternatively, in some examples pressure source (1416) is merely configured to provide an atmospheric vent to the distal end of tissue transport tube (302). Although not shown, it should be understood that pressure source (1416) may include a variety of structures. For instance, in some examples pressure source (1416) is a motorized air compressor. In other examples, pressure source (1416) is a syringe or other piston driven pressure generator. In still other examples, pressure source (1416) is merely a pressurized fluid reservoir that includes a discrete amount of pressurized fluid. Of course, other suitable alternative structures for pressure source (1416) will be apparent to those of ordinary skill in the art in view of the teachings herein.

In the present example, pressure source assembly (1410) is shown as a discrete component within biopsy system (2). Accordingly, pressure source assembly (1410) is separate and independently movable relative to biopsy device (10) and vacuum control module (400). However, it should be understood that in other examples pressure source assembly (1410) is integrated into one or more components of biopsy system (2). For instance, in some examples pressure source assembly (1410) is integrated into vacuum control module (400). In such examples, pressure source (1416) may be incorporated with other components of vacuum control module (400). In other examples, pressure source assembly (1410) is integrated with biopsy device (10) as similarly described above with respect to transport valve (1300). Of course, other suitable configurations integrating pressure source assembly (1410) with biopsy system (2) will be apparent to those of ordinary skill in the art in view of the teachings herein.

Figure 21:
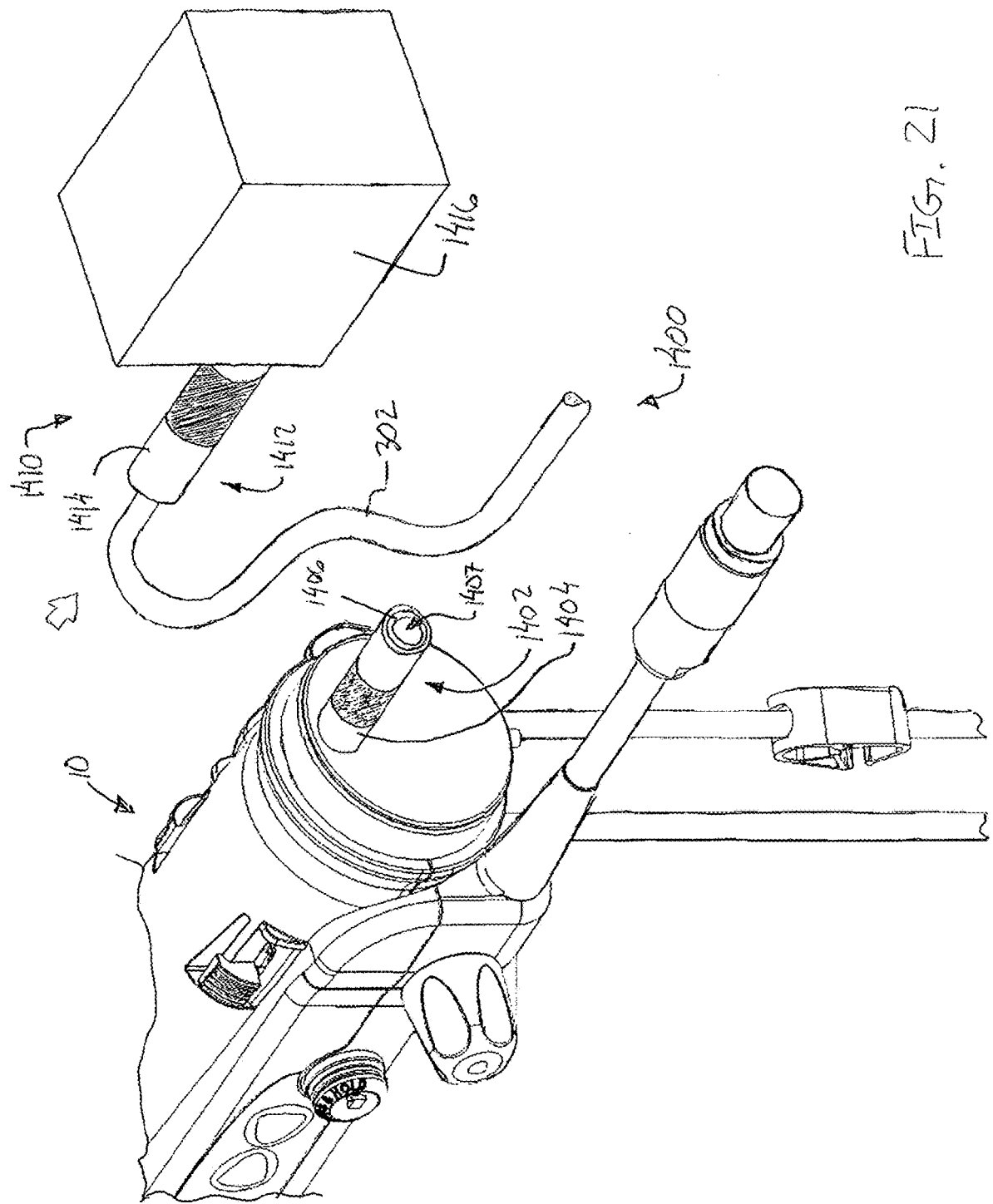
FIG. 21 depicts still another perspective view of the quick release pressure assembly of FIG. 19, with the tissue transport tube of the biopsy system of FIG. 1 coupled to a pressure source.

FIGS. 19-21 show an exemplary use of quick release pressure assembly (1400) in a biopsy procedure. As can be seen in FIG. 19, tissue transport tube (302) is initially coupled to quick release coupling (1402). In this configuration, tissue transport tube (302) is configured to receive one or more severed tissue samples from cutter (150) via quick release coupling (1402).

Once a desired number of tissue samples are received by tissue transport tube (302), an operator may desire to provide supplemental pressure to the distal end of tissue transport tube (302) to assist with transport of the severed tissue samples through tissue transport tube (302). To provide such supplemental pressure, an operator first translates outer sheath (1404) of quick release coupling (1402) to release male coupler (1408) from quick release coupling (1402) as shown in FIG. 20.

Once male coupler (1408) is released from quick release coupling (1402), the distal end of tissue transport tube (302) can be repositioned relative to biopsy device (10). With tissue transport tube (302) configured for repositioning, an operator may manually move the distal end of tissue transport tube (302) towards pressure source assembly (1410). Once tissue transport tube (302) positioned adjacent to pressure source assembly (1410), an operator may connect male coupler (1408) to quick release coupling (1412) of pressure source assembly (1410). To connect male coupler (1408), outer sheath (1414) of quick release coupling (1412) is translated and male connector is inserted into the inner female receiver of quick release coupling (1412). Outer sheath (1414) is then released and male coupler (1408) secures tissue transport tube (302) to quick release coupling (1412).

Once tissue transport tube (302) is secured to quick release coupling (1412), pressure source (1416) may be activated to provide pressurized fluid medium to the distal end of tissue transport tube (302). This pressurized fluid medium will then assist transport of tissue samples through tissue transport tube (302) by increasing the pressure differential between the distal and proximal ends of the transported tissue samples. Pressure source (1416) may supply pressurized fluid medium until one or more tissue samples are transported through tissue transport tube (302) to tissue handler (310). Pressure source (1416) may then be deactivated and tissue transport tube (302) may be reattached to biopsy device (10) by following the procedure described above in reverse order. The procedure described above may then be repeated as many times as desired to acquire any suitable number of additional tissue samples.

In some instances, it may be desirable to incorporate certain features into tissue transport tube (302) to improve the flow of fluid and/or tissue samples through tissue transport tube (302). For instance, in some examples altering the flow of fluid and/or tissue samples through tissue transport tube (302) may improve transport of tissue samples through tissue transport tube (302). This may reduce the propensity for tissue samples to create blockages within tissue transport tube (302). In addition, this may lead to better quality tissue samples due to preservation of the structural integrity of tissue samples traveling through tissue transport tube (302). Various illustrative examples of features to provide improved fluid flow within tissue transport tube (302) are described below. Although particular features are described below, it should be understood that various alternative features will be apparent to those of ordinary skill in the art in view of the teachings herein.

Figure 22:
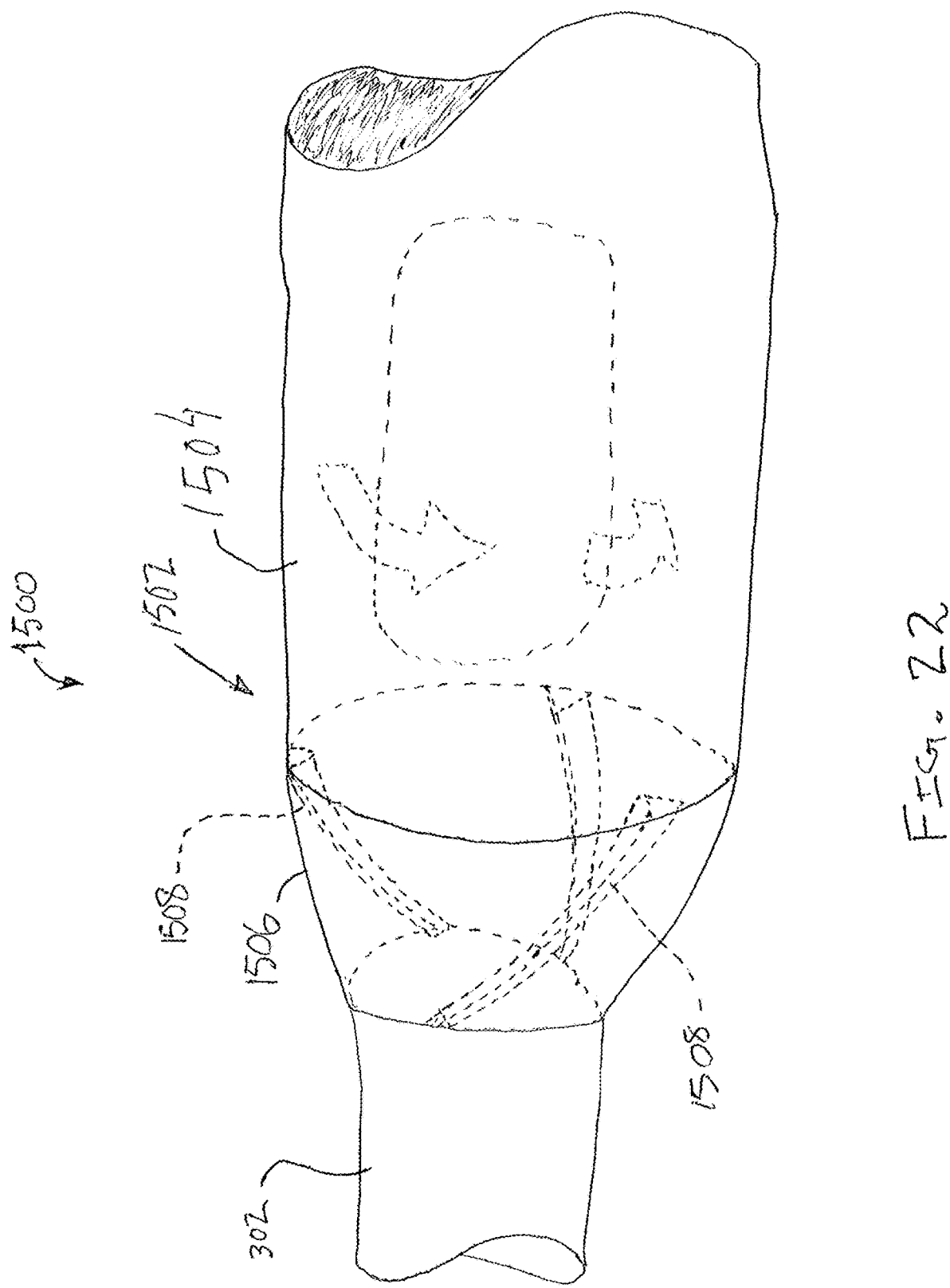
FIG. 22 depicts a perspective view of a fluid control insert that may be readily incorporated into the tissue transport tube of the biopsy system of FIG. 1.

FIG. 22 depicts a fluid control insert (1500) that may be incorporated into tissue transport tube (302) described above. As will be described in greater detail below, fluid control insert (1500) is generally configured to direct fluid and/or tissue samples flowing through tissue transport tube (302) into a predetermined flow pattern. In the present example, the predetermined flow pattern provided by fluid control insert (1500) is generally that of a vortex. However, it should be understood that the predetermined flow patter provided by fluid control insert (1500) may include other flow patterns such as laminar, annular, dispersed, and/or etc. In addition, or in the alternative, fluid control insert (1500) may be configured to generally reduce turbulence within fluid and/or tissue samples flowing through tissue transport tube (302).

Fluid control insert (1500) includes a tubular body (1502) defining a receiving portion (1504) and a neck portion (1506). Receiving portion (1504) generally defines an inner diameter that is greater than the inner diameter defined by tissue transport tube (302). This configuration of receiving portion (1504) is to permit necking down of the inner diameter of fluid control insert (1500) via neck portion (1506), as will be described in greater detail below. Accordingly, it should be understood that receiving portion (1504) is generally configured to receive a tissue sample with additional space between the tissue sample and the inner diameter of fluid control insert (1500) for fluid that may be present as the tissue sample is being transported though tissue transport tube (302).

Neck portion (1506) is disposed proximally of receiving portion (1504). Neck portion (1506) is generally configured to induce the fluid flow pattern of a vortex in fluid and/or tissue samples during flow through neck portion (1506). The shape of neck portion (1506) is generally frustoconical. This frustoconical shape is configured to induce the vortex based fluid flow pattern by forcing any fluid flowing through neck portion (1506) into a generally helical movement pattern. By inducing this form of fluid flow, transport of tissue samples through tissue transport tube (302) may be improved by concentrating movement of tissue samples along an axial path.

The interior of neck portion (1506) includes a plurality of fluid directors (1508) extending along the axial length of the interior of neck portion (1506). Although fluid directors (1508) are shown as elongate triangular protrusions protruding from the inner diameter of neck portion (1506), it should be understood that in other examples fluid directors (1508) may be defined as channels within the inner diameter of neck portion (1506). In addition, it should be understood that fluid directors (1508) may take on a variety of shapes beyond triangular such as rounded, square, or etc. Regardless of the particular configuration of fluid directors (1508), fluid directors (1508) generally define a helical pattern within neck portion (1506). The helical pattern defined by fluid directors (1508) is configured to induce a helical movement pattern of fluid and/or tissue samples following through neck portion (1506), thereby further inducing the vortex flow pattern described above.

Although the present example includes fluid directors (1508) disposed within neck portion (1506), it should be understood that in some examples fluid directors (1508) may be omitted entirely. For instance, in some examples the frustoconical shape of neck portion (1506) may be sufficient to provide the desirable vortex based flow pattern without fluid directors (1508). It should also be understood that in some examples fluid directors (1508) may not be limited to being disposed only within neck portion (1506). For instance, in some examples fluid directors (1508) may extend into receiving portion (1504) and/or tissue transport tube (302). Of course, various alternative configurations for fluid directors (1508) will be apparent to those of ordinary skill in the art in view of the teachings herein.

In the present example, fluid control insert (1500) is positioned on the distal end of tissue transport tube (302) such that the desired fluid flow pattern is induced in fluid and/or tissue samples flowing through tissue transport tube (302) prior to entry into tissue sample tube (302). In other examples, fluid control insert (1500) is positioned in an intermediate position along the length of tissue transport tube (302) between biopsy device (10) and tissue handler (310). In still other examples, multiple fluid control inserts (1500) are used in connection with tissue transport tube (302) at various positions along the length of tissue transport tube (302). Of course, various alternative ways in which fluid control insert (1500) may be incorporated into tissue transport tube (302) will be apparent to those of ordinary skill in the art in view of the teachings herein.

In some instances, it may be desirable increase the presence of atmospheric air in tissue transport tube (302) to assist with transport of tissue samples though tissue transport tube (302). For instance, as described above, tissue samples are transported through tissue transport tube (302) due to a pressure differential between the proximal and distal ends of a transported tissue sample. In the present example, vacuum is applied to the proximal end of the transported tissue sample to induce a negative pressure condition at the proximal end of the transported tissue sample. Meanwhile, the distal end of the transported tissue sample is subjected to atmospheric air thereby providing a pressure differential between the proximal and distal ends of the transported tissue sample. Generally, at least some atmospheric air is supplied by space defined between the cutter (150) and needle (110) itself. In some examples, needle (110) may be configured with an oval shaped cross-section and cutter (150) may be configured with a circular cross-section to provide additional space for communication of atmospheric air to the distal end of cutter (150) disposed within needle (110). However, in other examples, cutter (150) and needle (110) may have corresponding shapes, thereby limiting the amount of space for communication of atmospheric air to the distal end of the cutter (150). In such examples, the amount of atmospheric air communicated through the space between cutter (150) and needle (110) may be insufficient as the transported tissue sample is transported through tissue transport tube (302). Accordingly, in some examples methods and devices to increase the amount of atmospheric air delivered to tissue transport tube (302) may be desirable. Various illustrative examples of methods and devices to provide increased atmospheric air to tissue transport tube (302) are described below. Although particular devices and methods are described below, it should be understood that various alternative devices and methods will be apparent to those of ordinary skill in the art in view of the teachings herein.

Figure 23:
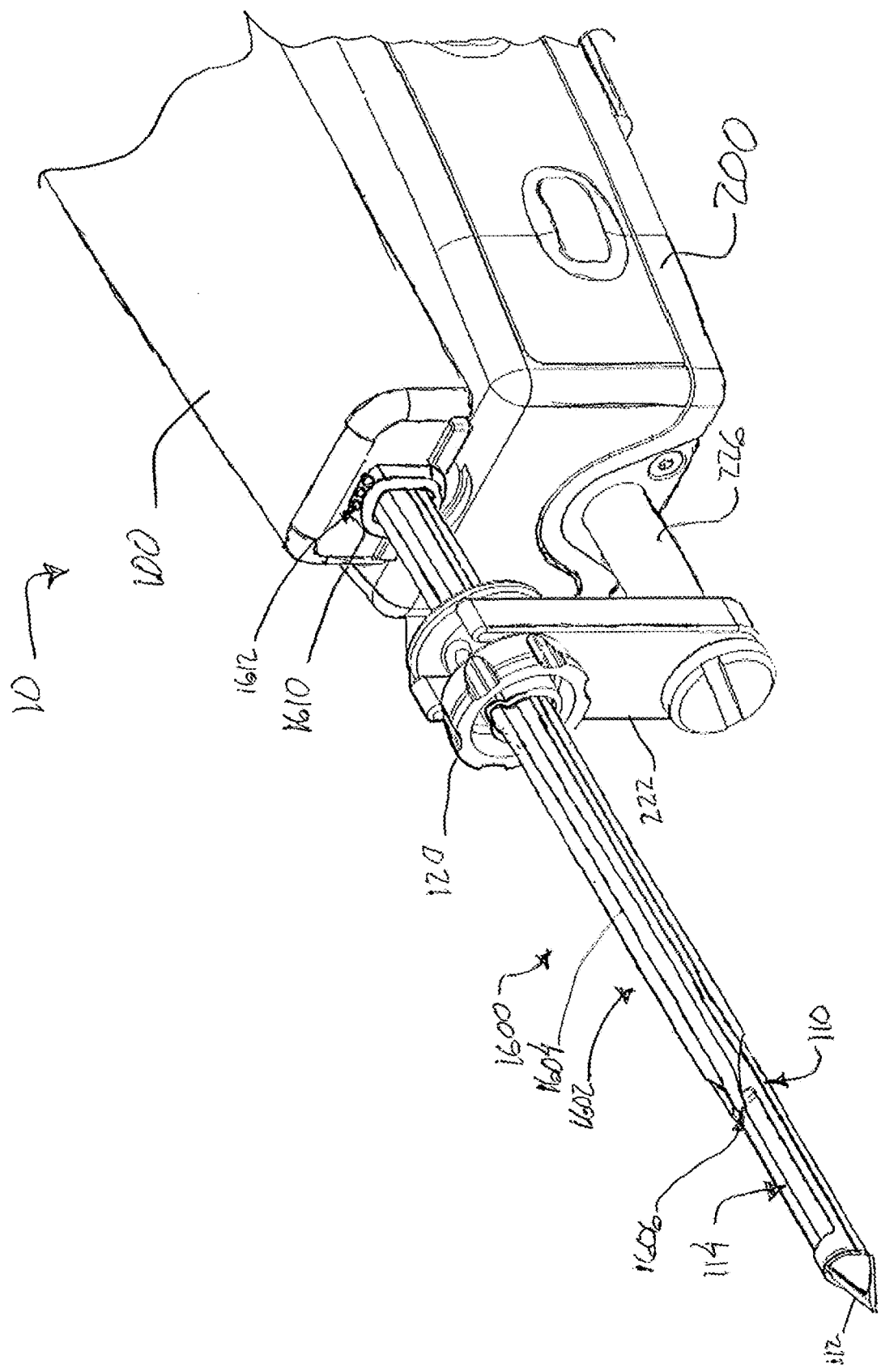
FIG. 23 depicts a perspective view of an introducer incorporated into the biopsy device of the biopsy system of FIG. 1.
Figure 24:
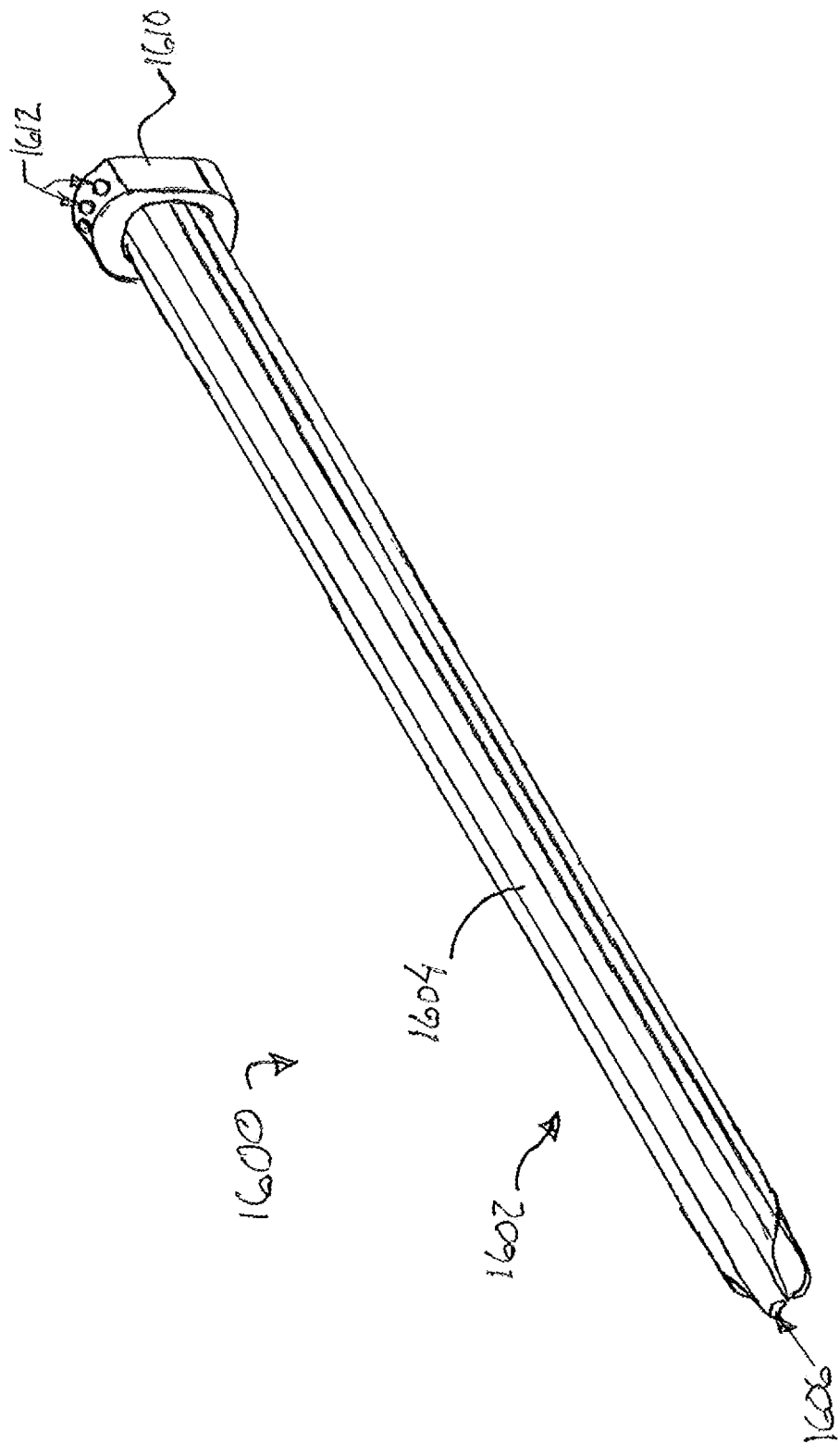
FIG. 24 depicts a perspective view of the introducer of FIG. 23.

FIG. 23 shows biopsy device (10) equipped with an exemplary introducer (1600) for providing additional atmospheric air to cutter (150). As will be described in greater detail below, introducer (1600) is generally configured to provide atmospheric air to cutter (150) disposed within needle (110) from a source external to a patient. Introducer (1600) includes an elongate cannula (1602), and a hub (1610). Cannula (1602) is best seen in FIG. 24. As can be seen, cannula (1602) is generally shaped to correspond to the shape of needle (110). The longitudinal length of cannula (1602) is generally sized to extend from probe (100) to lateral aperture (114). Cannula (1602) further comprises a vent feature (1604) on an upper portion of cannula (1602). Vent feature (1604) extends along the entire length of cannula (1602) and defines a vent lumen (1606) therein. As will be described in greater detail below, vent feature (1604) is generally configured to communicate atmospheric air from hub (1610) to cutter (150) via lateral aperture (114).

Hub (1610) is generally configured to secure to or otherwise abut probe (100). Hub (1610) defines one or more vent ports (1612) extending through hub (1610). Vent ports (1612) are configured to communicate atmospheric air from the exterior of hub (1610) to vent lumen (1606) within cannula (1602). Thus, it should be understood that atmospheric air may flow through vent ports (1612) in hub (1610) and into vent lumen (1606) defined by vent feature (1604) of cannula (1602).

In an exemplary use, introducer (1600) is generally disposed co-axially with needle (110) as shown in FIG. 23. In this position, vent lumen (1606) is positioned to communicate with lateral aperture (114) of needle (110). During tissue sample collection via needle (110), introducer (1600) operates in a passive manner. For instance, as a tissue sample is transported through cutter (150) disposed within needle (110), and then within tissue transport tube (302), the transported tissue sample will generate an increasing amount of volume distally of the transported tissue sample. This increasing volume will draw atmospheric air into cutter (150) disposed within needle (110). Some of this atmospheric air may be communicated through the space between cutter (150) disposed within needle (110) and needle (110) itself. In addition, some of this atmospheric air may also be drawn from introducer (1600) via vent lumen (1606). As atmospheric air is drawn from vent lumen (1606), the atmospheric air will first enter introducer (1600) through the one or more vent ports (1612) in hub (1610). The atmospheric air will then travel through vent lumen (1606) of vent feature (1604) and enter lateral aperture (114) of needle (110). Once atmospheric air enters lateral aperture (114), the atmospheric air will be drawn into cutter (150) disposed within needle (110) and later into tissue transport tube (302).

Figure 25:
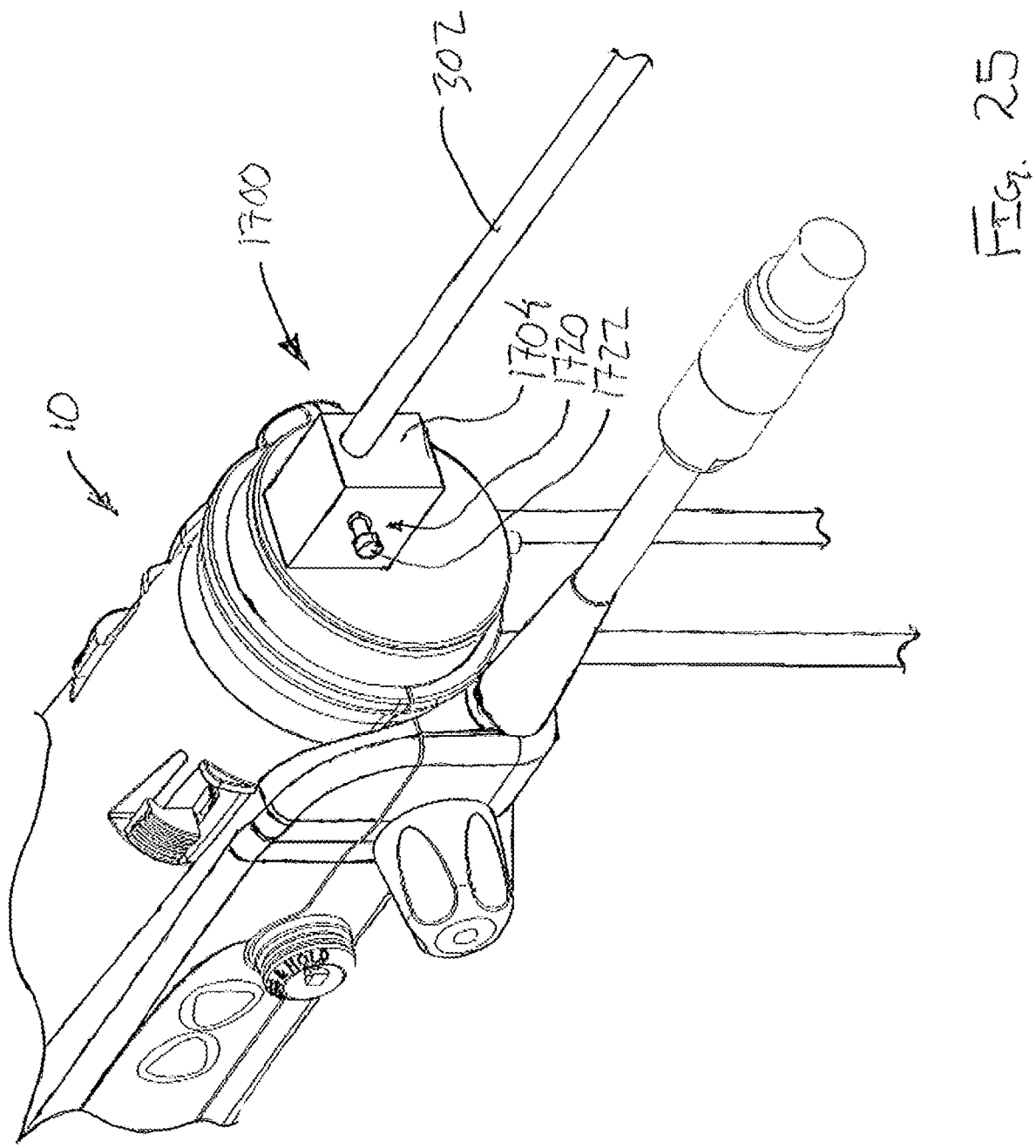
FIG. 25 depicts a perspective view of a vent valve incorporated into the biopsy device of the biopsy system of FIG. 1.

FIG. 25 shows biopsy device (10) equipped with an exemplary supplemental vent valve (1700). Vent valve (1700) is generally configured to selectively supply tissue transport tube (302) with supplemental atmospheric ventilation to promote transport of tissue samples through tissue transport tube (302). Vent valve (1700) is coupled directly to biopsy device (10), although in some examples an intermediate tube may be used such that vent valve (1700) is separate from biopsy device (10). Although not shown, it should be understood that a tube or other structure extends distally from vent valve (1700) into biopsy device (10) to place vent valve (1700) into communication with cutter (150) disposed within needle (110). Thus, it should be understood that tissue samples may be transported through thorough biopsy device (10) and into vent valve (1700) prior to being transported through tissue transport tube (302).

Vent valve (1700) includes a valve body (1704) and a supplemental vent (1720). Valve body (1704) houses various valve components to change the fluid state of vent valve (1700) between a tissue collection state and a tissue transport state, as will be described in greater detail below. Although not shown, it should be understood that the valve components within valve body (1704) are only configured to permit the positive flow of fluid through vent valve (1700) and into tissue transport tube (302). Thus, it should be understood that the valve components within valve body (1704) prevent the positive flow of fluid through vent valve (1700) and into biopsy device (10). This configuration prevents positive fluid from being communicated into cutter (150) and into a patient.

Although not shown, it should be understood that in some examples vent valve (1700) may include a selector or other component disposed on a side of valve body (1704). Such a selector can be generally configured to permit manual actuation of vent valve (1700) between the tissue collection state and the tissue transport state. Although some examples can use manual actuation to change the fluid state of vent valve (1700), it should be understood that in other examples an electronic or pneumatically based actuator can be used. In such examples, actuation of vent valve (1700) may be controlled remotely by vacuum control module (400) based on pre-programed control algorithms.

Supplemental vent (1720) extends from valve body (1704) to and includes an air filter (1722) on an outer end thereof. When vent valve (1700) is transitioned to the tissue transport state via the selector or other manual or automatic means, supplemental vent (1120) is in communication with atmospheric air such that atmospheric air may flow through air filter (1722) and into tissue transport tube (302). By contrast, when vent valve (1700) is transitioned to the tissue collection state via the selector or other manual or automatic means, supplemental vent (1120) is closed and is not in communication with tissue transport tube (302).

In an exemplary use, vent valve (1700) is initially set to the tissue collection state for acquisition of a tissue sample via needle (110). When in the tissue collection state, vacuum flows through tissue transport tube (302) from vacuum control module (400), through vent valve (1700), and into cutter (150) disposed within needle (110). Once a tissue sample is severed by cutter (150) within needle (110), the severed tissue sample is transported through cutter (150) and into tissue transport tube (302) via vent valve (1700).

Once the severed tissue sample is disposed proximally of vent valve (1700), an operator may manually actuate the selector or other manual or automatic actuator to transition vent valve (1700) into the transport state. Alternatively, in examples where the selector is replaced with an electrical or pneumatic actuator, such an actuator may be remotely triggered to transition vent valve (1700) automatically. Where vent valve (1700) is transitioned automatically, such automatic transitioning may occur a predetermined time after cutter (150) is moved through a cutting stroke. Alternatively, in some examples vent valve (1700) may be equipped with a tissue sensor or other switch to indicate passage of a tissue sample into tissue transport tube (302). Such a tissue sensor may be used by vacuum control module (400) to identify when to transition vent valve (1700) to the transport state.

Once vent valve (1700) is transitioned to the transport state, supplemental vent (1120) may communicate atmospheric air from air filter (1722) thorough vent valve (1120) and into tissue transport tube (302). Thus, when in the transportation state, vent valve (1700) generally provides atmospheric air distally relative to the severed tissue sample to enhance the pressure differential propelling the severed tissue sample though tissue transport tube (302).

Once the severed tissue sample is transported to tissue handler (310) through tissue transport tube (302), vent valve (1700) may be transitioned back to the tissue collection state using the procedure described above. The process may then be repeated again as necessary until all desired tissue samples are collected into tissue handler (310).

Figure 26:
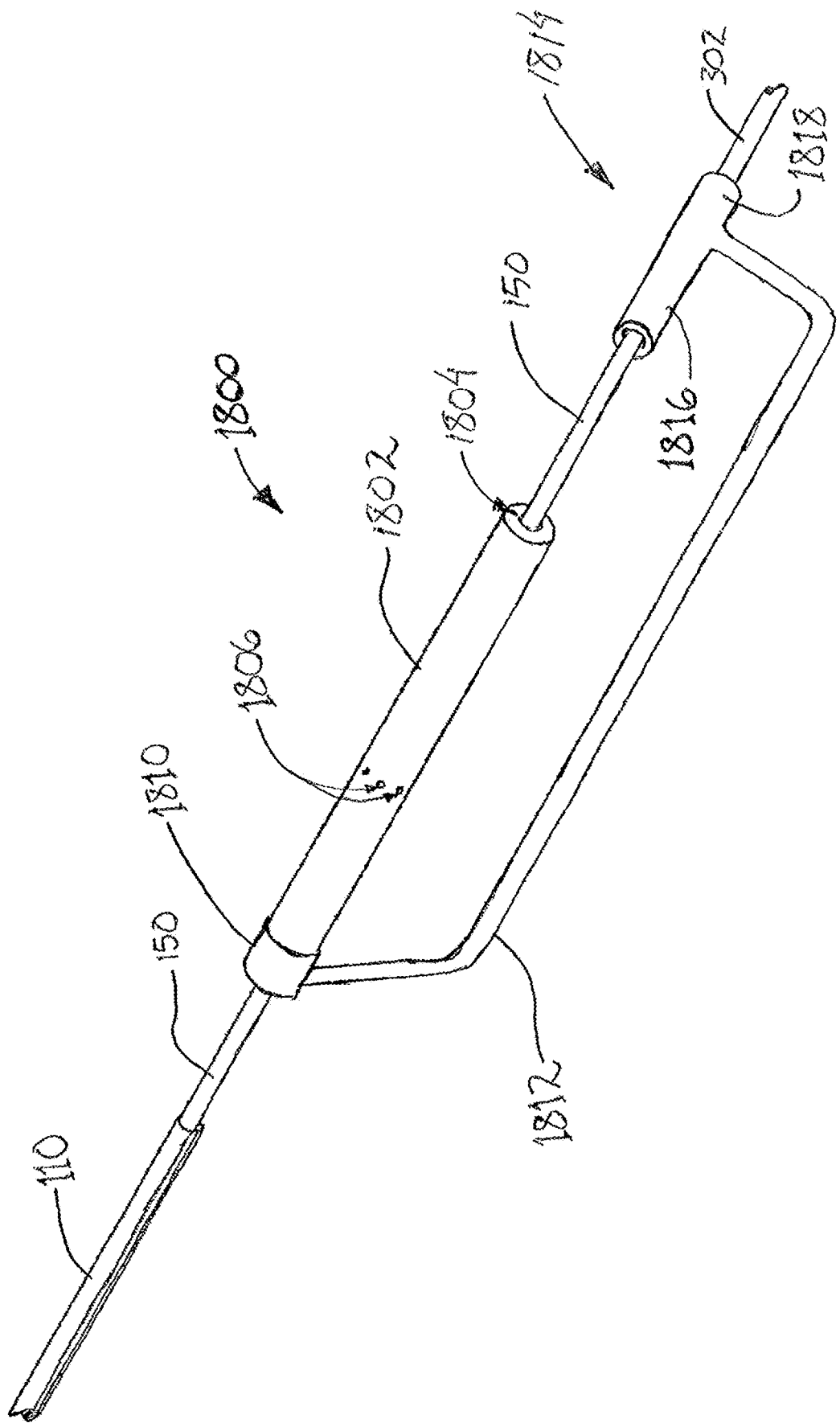
FIG. 26 depicts a perspective view of a vent assembly that may be readily incorporated into the biopsy device of the biopsy system of FIG. 1.

FIGS. 26 and 27 show an exemplary vent assembly (1800) that may be readily incorporated into biopsy device (10). As will be described in greater detail below, vent assembly (1800) is generally configured to provide selective atmospheric vent to tissue transport tube (302) based in part on the axial position of cutter (150). As can be seen, vent assembly (1800) includes a valve body (1802), a vent manifold (1810), a shuttle valve slider (1820), a distal pusher (1830) and a proximal pusher (1832). Valve body (1802) comprises a hollow generally cylindrical tube. The proximal end of valve body (1802) includes a cutter opening (1804). Cutter opening (1804) is sized to receive cutter (150) such that cutter (150) may translate though cutter opening (1804). Although not shown, it should be understood that cutter opening (1804) includes one or more seals to fluidly seal the interface between cutter (150) and cutter opening (1804).

Valve body (1802) includes a plurality of vent openings (1806) disposed in a circular pattern around the circumference of valve body (1802). Vent openings (1806) are generally configured to communicate atmospheric air into the hollow interior of valve body (1802). Vent openings (1806) are generally positioned near the center of valve body (1802). However, as will be understood, numerous alternative positons for vent openings (1806) may be used in other examples.

Vent Manifold (1810) is disposed on the distal end of valve body (1802). Although not shown, it should be understood that the distal end of vent body (1810) is generally open such that the hollow interior of valve body (1810) is generally in fluid communication with vent manifold (1810). A vent tube (1812) extends downwardly and proximally from vent manifold (1810). As will be understood, vent tube (1812) is generally configured to communicate atmospheric air from vent manifold (1810) to tissue transport tube (302).

Vent tube (1812) further extends proximally past valve body (1802) and terminates in a T-junction (1814). T-junction (1814) defines a cutter portion (1816) and a coupling portion (1818). Cutter portion (1816) is configured to receive cutter (150) and to permit at least some translation of cutter (150) within T-junction (1814). To accommodate translation of cutter (150) without separating from cutter (150), cutter portion (1816) is generally elongate relative to coupling portion (1818). Coupling portion (1818) is configured to couple to tissue transport tube (302).

T-junction (1814) defines a generally hollow interior that is in communication with vent tube (1812). As will be described in greater detail below, this generally permits atmospheric air to travel through T-junction (1814) and into tissue transport tube (302). Thus, when atmospheric air is supplied to tissue transport tube (302), the atmospheric air enters the hollow interior of valve body (1802) via vent openings (1806), enters vent tube (1812) via vent manifold (1810) and finally enters tissue transport tube (302) via T-junction (1814).

Shuttle valve slider (1820) is best seen in FIG. 27. As can be seen, shuttle valve slider (1820) comprises a generally cylindrical body (1822). Body (1822) is positioned coaxially with cutter (150). In addition, body (1822) is generally configured to freely side relative to cutter (150) to permit at least some translation of cutter (150) relative to body (1822). Body (1822) defines a plurality of notches (1824) on opposite ends of body (1822). Notches (1824) are configured to provide fluid communication to the interior of shuttle valve slider (1820) even as pushers (1830, 1832) contact shuttle valve slider (1820). Thus, it should be understood that shuttle valve slider (1820) is generally configured to permit fluid flow through a space defined between cutter (150) and the interior of body (1822).

Body (1822) further includes O-rings (1826) disposed on adjacent to the proximal and distal ends of body (1822). O-rings (1826) are configured to seal against the interior of valve body (1802) while permitting shuttle valve slider (1820) to translate within valve body (1802). Thus, it should be understood that the outer diameter of body (1822) is generally sized to be approximately equivalent to the inner diameter of valve body (1802) with some clearance for O-rings (1826).

Distal pusher (1830) is disposed coaxially about cutter (150) distally of shuttle valve slider (1820). Similarly, proximal pusher (1832) is disposed coaxially about cutter (150) proximally of shuttle valve slider (1820). Both pushers (1830, 1832) are fixedly secured to cutter (150) such that translation of cutter (150) results in corresponding motion of pushers (1830, 1832). As will be described in greater detail below, pushers (1830, 1832) are generally configured to push shuttle valve slider (1820) in response to motion of cutter (150) to change the valve state of vent assembly (1800).

In an exemplary use, shuttle valve slider (1820) is used to shift vent assembly (1800) between a sealed state and a vent state. In the sealed state, shuttle valve slider (1820) is positioned such that vent openings (1806) of valve body (1802) are positioned between O-rings (1826) of shuttle valve slider (1820). O-rings (1826) thus prevent atmospheric air from entering the hollow interior of valve body (1802) when shuttle valve slider (1820) is in the sealed state.

In the vent state, shuttle valve slider (1820) is positioned proximally or distally relative to vent openings (1806) of valve body (1802). For instance, when shuttle valve slider (1820) is positioned proximally of vent openings (1806), atmospheric air travels into the hollow interior of valve body (1802) via vent openings (1806) and then into vent manifold (1810), where the atmospheric air can travel into tissue transport tube (302) via vent tube (1812) and T-junction (1814). Similarly, when shuttle valve slider (1820) is positioned distally of vent openings (1806), atmospheric air travels into the hollow interior of valve body (1802) via vent openings (1806). However, once inside, the atmospheric air next travels through shuttle valve slider (1820) between body (1822) and cutter (150). Once through shuttle valve slider (1820), the atmospheric air then travels into tissue transport tube (302) via vent tube (1812) and T-junction (1814). Thus it should be understood that when vent assembly (1800) is in the vent state, atmospheric air can travel from vent openings (1804) and into tissue transport tube (302) via vent manifold (1810), vent tube (1812), and T-junction (1814).

To transition between the sealed state and the vent state, shuttle valve slider (1820) is pushed by either distal pusher (1830) or proximal pusher (1832). Because both pushers (1830, 1832) are fixedly secured to cutter (150), translation of cutter (150) generally results in translation of shuttle valve slider (1820). For instance, proximal translation of cutter (150) generally results in distal pusher (1830) pushing shuttle valve slider (1820) proximally. Likewise, distal translation of cutter (150) generally results in proximal pusher (1832) pushing shuttle valve slider (1820) distally. However, because pushers (1830, 1832) are spaced on cutter (150) a greater axial distance than the length of shuttle valve slider (1820), there is some lost motion where translation of cutter (150) results in no translation of shuttle valve slider (1820). This results in vent assembly (1800) remaining in a constant state (e.g., sealed state) even while cutter (150) is translating.

In the present example, the configuration of pushers (1830, 1832) and shuttle valve slider (1820) relative to cutter (150) is configured to provide various states at certain stages during the biopsy procedure. For instance, when a tissue sample is severed via cutter (150) it may be desirable for vent assembly (1800) to be in a sealed state so that vacuum may be used to transport the severed tissue sample through cutter (150) and into tissue transport tube (302). However, once the severed tissue sample is transported to tissue transport tube (302), it may be desirable to provide atmospheric air to the distal end of tissue transport tube (302) to assist transport of the severed tissue sample through tissue transport tube (302). Accordingly, when cutter (150) is translated distally to sever a tissue sample, proximal pusher (1832) correspondingly pushes shuttle valve slider (1820) distally to transition vent assembly (1800) into the sealed state. Once the sample is severed, vent assembly (1800) remains in the sealed state during an initial phase of transport, where the severed tissue sample is transported though cutter (150).

After the initial phase of transport, cutter (150) begins to move proximally. This proximal movement causes distal pusher (1830) to push shuttle valve slider (1820) proximally to place vent assembly (1800) into the vent state. This permits atmospheric air to travel through vent openings (1806), into vent tube (1812) and T-junction (1814), and into tissue transport tube (302). After the severed tissue sample is transported to tissue handler (310) through tissue transport tube (302), cutter (150) may be advanced again and the process described above may be repeated to collect a desired number of tissue samples.

Figure 29:
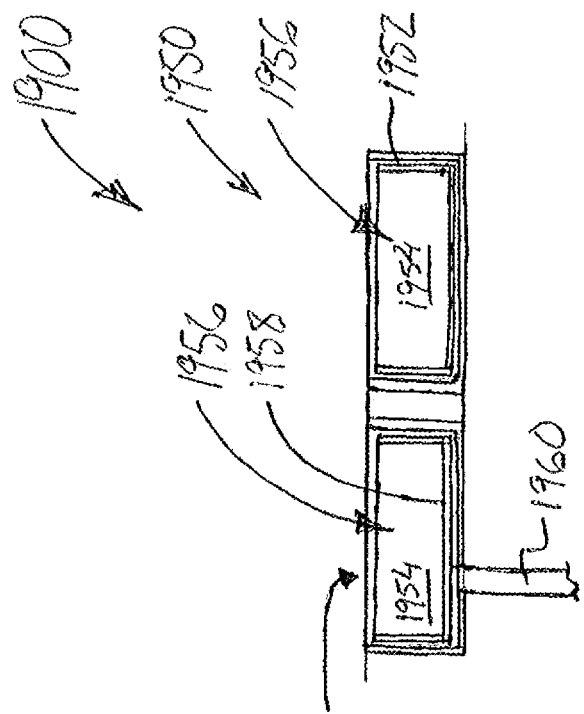
FIG. 29 depicts a side cross-sectional view of the tissue sample holder of FIG. 28.
Figure 28:
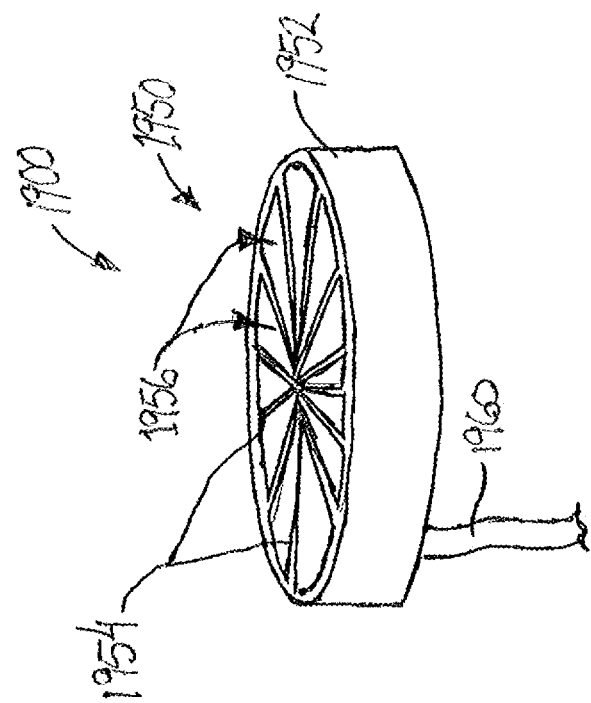
FIG. 28 depicts a perspective view of an alternative tissue sample holder that may be readily incorporated into the biopsy system of FIG. 1.

FIGS. 28 and 29 show an exemplary alternative tissue sample holder (1900) that may be readily incorporated into tissue handler (310) in lieu of tissue sample holder (340) described above. Tissue sample holder (1900) is substantially the same as tissue sample holder (340) described above, unless otherwise noted herein. In particular, like with tissue sample holder (340), tissue sample holder (1900) of the present example is generally in communication with tissue transport tube (302) to receive a plurality of tissue samples in a predetermined configuration. Although not shown it should be understood that like with tissue sample holder (340), tissue sample holder (1900) of the present example comprises a tissue directing top (not shown), and outer container (not shown).

Tissue sample holder (1900) further comprises a rotatable sample tray (1950) disposed within the top and the outer container. Sample tray (1950) of the present example is substantially the same as sample tray (350) described above. For instance, sample tray (1950) generally includes an outer cylindrical body (1952) and a rotation shaft (not shown). Cylindrical body (1952) includes a plurality of sidewalls (1954). Sidewalls (1954) define a plurality of pie-shaped tissue sample chambers (1956). Each sample chamber (1956) is configured to receive one or more tissue samples. Each sample chamber (1956) is open to the top of sample tray (1950) such that tissue samples are received within the top of sample tray (1950). Sample tray (1950) also includes a floor (1958) in the bottom of cylindrical body (1952). Thus, tissue samples received within each sample chamber (1956) may be deposited on floor (1958). To promote the flow of vacuum through sample tray (1950), the floor may include a plurality of openings or perforations. In addition, the plurality of openings or perforations may also promote the drainage of excess fluids while maintaining tissue samples within sample chambers (1956).

Unlike sample tray (350) described above, sample tray (1950) of the present example includes a localized vacuum source (1960). Vacuum source (1960) is generally configured to provide localized vacuum relative to a selected sample chamber (1956) to encourage communication of tissues samples into the selected sample chamber (1956). As best seen in FIG. 29, vacuum source (1960) is positioned directly beneath a selected sample chamber (1956). Although not shown, it should be understood that this position generally corresponds to vacuum source (1960) being directly beneath a redirection elbow (not shown) similar to redirection elbow (344) described above with respect to tissue directing top (342). Thus, vacuum source (1960) is configured to pull tissue samples directly from the redirection elbow and into the selected chamber (1956). In the present example, vacuum source (1960) communicates through floor (1958). Thus, it should be understood that floor (1958) is generally configured to communicate fluids therethrough while preventing the passage of tissue samples. In some examples floor (1958) includes a plurality of perforations to permit fluid communication from sample chamber (1956) to vacuum source (1960). In other examples floor (1958) includes a plurality of openings to permit fluid communication from sample chamber (1956) to vacuum source (1960). Of course, in other examples any other suitable fluid communication structure within floor (1958)

may be used as will be apparent to those of ordinary skill in the art in view of the teachings herein.

Although not shown, it should be understood that sample tray (1950) and/or other components of tissue sample holder (1900) may include one or more seals to fluidly isolate the selected sample chamber (1956) in communication with vacuum source (1960) from the other sample chambers (1956). Such fluid isolation may be desirable to promote the flow of vacuum through the selected sample chamber (1956) at the exclusion of other sample chambers (1956). As will be understood, this feature may enhance transport of one or more tissue samples to the selected sample chamber (1956).

In an exemplary use, it should be understood that vacuum source (1960) generally remains stationary relative to sample tray (1950). Accordingly, once a selected sample chamber (1956) is filled with one or more tissue samples, sample tray (1950) may rotate. Because vacuum source (1960) remains stationary, rotation of sample tray (1950) results in vacuum source (1960) being placed in communication with another selected sample chamber (1956). Once positioned in communication with another selected sample chamber (1956), vacuum source (1960) may pull another one or more tissue samples in the next selected sample chamber (1956). This process may be repeated to collect as many samples as desired by an operator.

Figure 31:
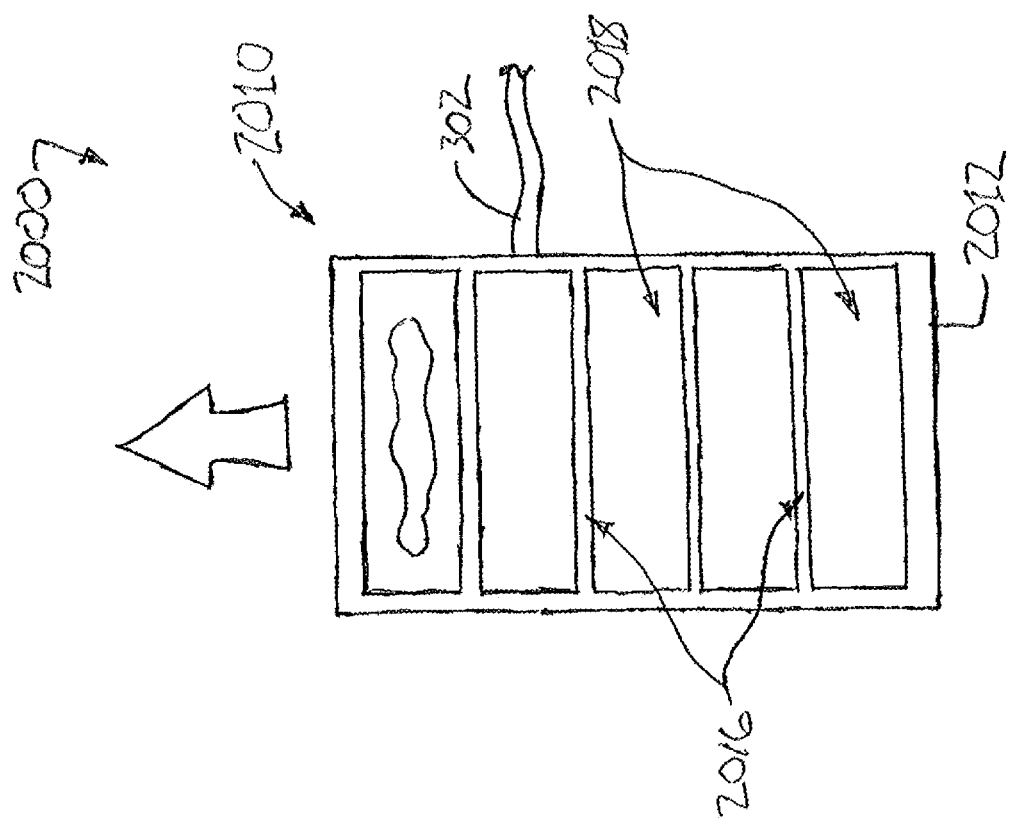
FIG. 31 depicts a top plan view of the tissue sample holder of FIG. 30.
Figure 30:
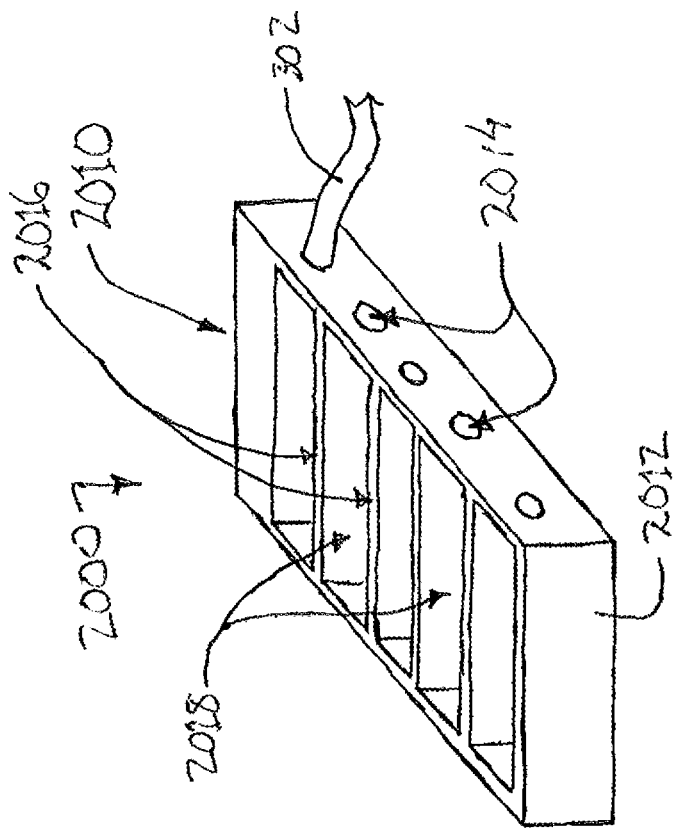
FIG. 30 depicts a perspective view of another alternative tissue sample holder that may be readily incorporated into the biopsy system of FIG. 1.

FIGS. 30 and 31 show another exemplary alternative tissue sample holder (2000) that may be readily incorporated into tissue handler (310) in lieu of tissue sample holder (340) described above. Unlike tissue sample holder (340) described above, tissue sample holder (2000) is configured for side loading of tissue samples. Tissue sample holder (2000) comprises a rectangular tissue sample cassette (2010). Although not shown, it should be understood that in some examples cassette (2010) is generally enclosed within a cassette housing or other structure configured to seal cassette (2010) relative to the exterior of cassette (2010). Such a cassette housing may be generally configured to direct vacuum into cassette (2010) to provide transport of tissue samples through tissue transport tube (302) and into cassette (2010).

Cassette (2010) includes a rectangular outer body (2012) and a plurality of sidewalls (2016) defining a plurality of sample collection chambers (2018) within cassette (2010). On the exterior of cassette (2010), outer body (2012) defines a plurality of tissue communication bores (2014) that correspond to each sample collection chamber (2018). As will be understood, each tissue communication bore (2014) is generally in fluid communication with a corresponding sample collection chamber (2018). This permits tissue transport tube (302) to selectively couple to each tissue communication bore (2014) to thereby communicate tissue samples into a corresponding sample collection chamber (2018).

Although not shown, it should be understood that in some example outer body (2012) may include a track or other coupling feature to support tissue transport tube (302) and thereby permit tissue transport tube (302) to selectively couple to each tissue communication bore (2014). In other examples, tissue transport tube (302) is coupled to a structure configured to receive cassette (2010). In such examples, tissue transport tube (302) may remain stationary with the structure, while cassette (2010) moves relative to the structure to successively index tissue transport tube (302) with each tissue communication bore (2014). Of course, any other suitable configuration to promote selective coupling between each tissue communication bore (2014) and tissue transport tube (302) may be used as will be apparent to those of ordinary skill in the art in view of the teachings herein.

In an exemplary use, tissue transport tube (302) is initially indexed with a selected tissue communication bore (2014) and is thereby in fluid communication with a corresponding selected sample collection chamber (2018). At this stage, the entirety of cassette (2010) may be under vacuum pressure to communicate one or more tissue samples through tissue transport tube (302) and into the selected sample collection chamber (2018). Alternatively, in other examples, cassette (2010) or other structures surrounding cassette (2010) may be configured to apply localized vacuum to only the selected sample collection chamber (2018).

Regardless of how vacuum is applied to the selected sample collection chamber (2018), one or more tissue samples are next communicated through tissue transport tube (302) and into the selected sample collection chamber (2018) via the selected tissue communication bore (2014). Once tissue samples are received within the selected sample collection chamber (2018), an operator may optionally engage in preliminary analysis of the one or more tissue samples collected within the selected sample collection chamber (2018). Suitable forms of preliminary analysis may include, for example, x-ray analysis, bioimpedance analysis, visual analysis via CCD or direct visual inspection, and/or etc.

Once a desired number of tissue samples are collected and/or analyzed within the selected sample collection chamber (2018), cassette (2010) is adjusted to receive one or more tissue samples within another selected sample collection chamber (2018). To adjust cassette (2010) to receive one or more tissue samples within another selected sample collection chamber (2018), cassette (2010) is moved longitudinally as shown in FIG. 31. As described above, tissue transport tube (302) is generally stationary relative to cassette (2010). Accordingly, longitudinal movement of cassette (2010) results in tissue transport tube (302) being placed in communication with another selected tissue communication bore (2014) and corresponding selected sample collection chamber (2018). Although FIG. 31 shows the selected sample collection chamber (2018) being the next adjacent sample collection chamber (2018), it should be understood that any one sample collection chamber (2018) may be used.

After cassette (2010) is adjusted as described above, vacuum is again applied to the selected sample collection chamber (2018) as described above. This pulls one or more tissue samples thorough tissue transport tube (302) and into the selected sample collection chamber (2018) via the selected tissue communication bore (2014). Once a desired number of tissue samples are acquired within the selected sample collection chamber (2018), preliminary analysis may then be optionally performed. Once performed, the process described above may be repeated again to communicate one or more tissue samples in to the other remaining tissue collection chambers (2018) until a desired total number of tissue samples have been collected.

Figure 31A:
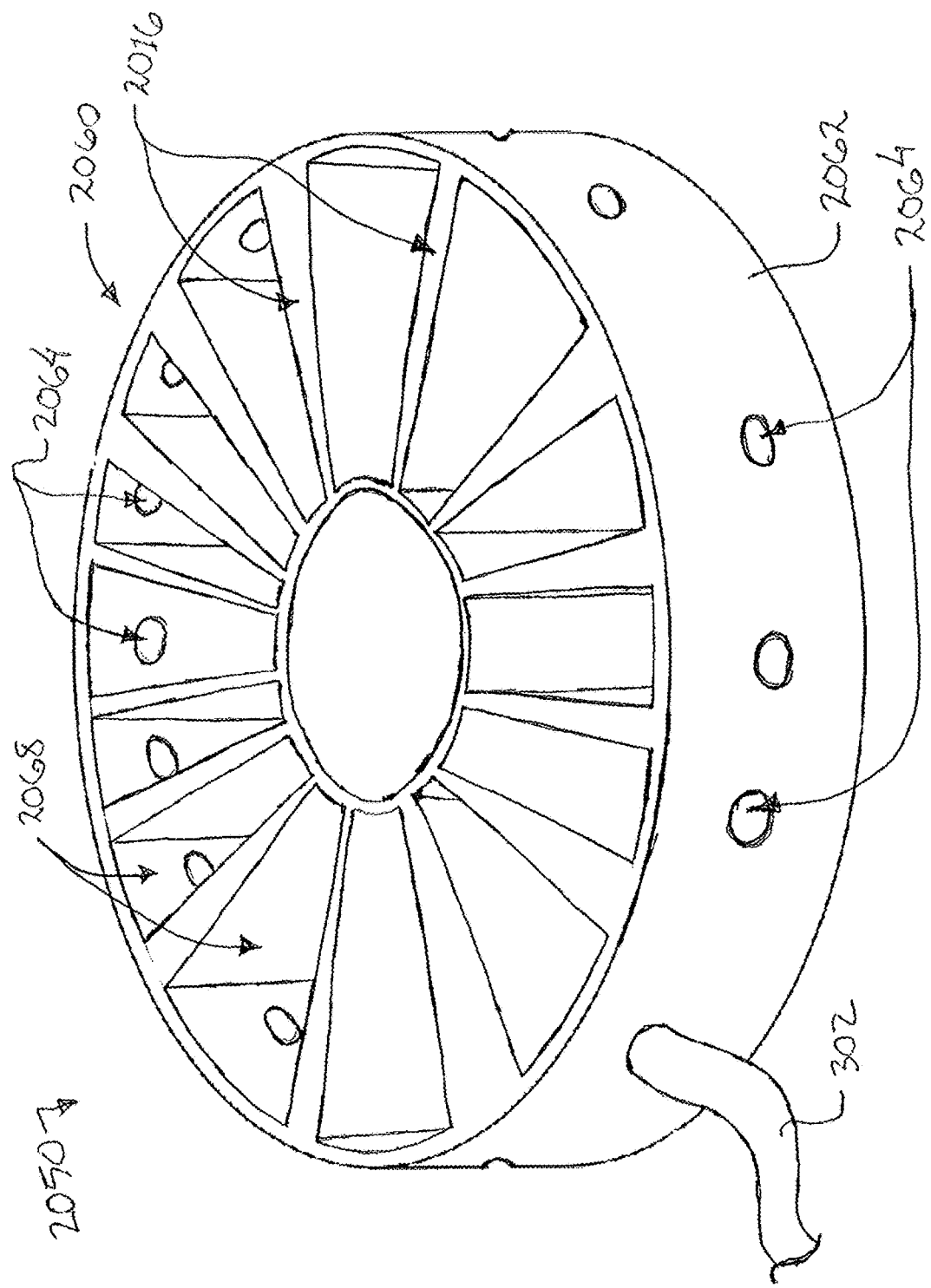
FIG. 31A depicts a perspective view of still another alternative tissue sample holder that may be readily incorporated into the biopsy system of FIG. 1.

FIG. 31A shows another exemplary alternative tissue sample holder (2050) that may be readily incorporated into tissue handler (310) in lieu of tissue sample holder (340) described above. Tissue sample holder (2050) is similar to tissue sample holder (2000) described above, except tissue sample holder (2050) includes sample collection chambers (2068) oriented in a circular array rather than in a linear array. However, as with tissue sample holder (2000) described above, tissue sample holder (2050) is configured for side loading of tissue samples. Tissue sample holder (2050) comprises a circular tissue sample cassette (2060). Although not shown, it should be understood that in some examples cassette (2060) is generally enclosed within a cassette housing or other structure configured to seal cassette (2060) relative to the exterior of cassette (2060). Such a cassette housing may be generally configured to direct vacuum into cassette (2060) to provide transport of tissue samples through tissue transport tube (302) and into cassette (2060).

Cassette (2060) includes a cylindrical outer body (2062) and a plurality of sidewalls (2066) defining a plurality of sample collection chambers (2068) within cassette (2060). On the exterior of cassette (2060), outer body (2062) defines a plurality of tissue communication bores (2064) that correspond to each sample collection chamber (2068). As will be understood, each tissue communication bore (2064) is generally in fluid communication with a corresponding sample collection chamber (2068). This permits tissue transport tube (302) to selectively couple to each tissue communication bore (2064) to thereby communicate tissue samples into a corresponding sample collection chamber (2068). Although each tissue communication bore (2064) is shown in a particular location relative to outer body (2062), it should be understood that any suitable position may be used. For instance, in some examples each tissue communication bore (2064) is positioned near the floor of outer body (2062). In such examples, this positioning of tissue communication bore (2064) may be desirable to promote the stability of a tissue sample as it is received within sample collection chamber (2068), thereby keeping the tissue sample intact.

Although not shown, it should be understood that in some examples outer body (2062) may include a track or other coupling feature to support tissue transport tube (302) and thereby permit tissue transport tube (302) to selectively couple to each tissue communication bore (2064). In other examples, tissue transport tube (302) is coupled to a structure configured to receive cassette (2060). In such examples, tissue transport tube (302) may remain stationary with the structure, while cassette (2060) moves relative to the structure to successively index tissue transport tube (302) with each tissue communication bore (2064). Of course, any other suitable configuration to promote selective coupling between each tissue communication bore (2064) and tissue transport tube (302) may be used as will be apparent to those of ordinary skill in the art in view of the teachings herein.

In an exemplary use, tissue transport tube (302) is initially indexed with a selected tissue communication bore (2064) and is thereby in fluid communication with a corresponding selected sample collection chamber (2068). At this stage, the entirety of cassette (2060) may be under vacuum pressure to communicate one or more tissue samples through tissue transport tube (302) and into the selected sample collection chamber (2068). Alternatively, in other examples, cassette (2060) or other structures surrounding cassette (2060) may be configured to apply localized vacuum to only the selected sample collection chamber (2068).

Regardless of how vacuum is applied to the selected sample collection chamber (2068), one or more tissue samples are next communicated through tissue transport tube (302) and into the selected sample collection chamber (2068) via the selected tissue communication bore (2064). This permits tissue samples to be received within sample collection chamber (2068) in a lateral direction rather than axially via redirection elbow (344) in tissue sample handling assembly (300) described above. Thus, it should be understood that tissue sample holder (2050) of the present configuration permits structures similar to redirection elbow (344) to be omitted.

Once tissue samples are received within the selected sample collection chamber (2068), an operator may optionally engage in preliminary analysis of the one or more tissue samples collected within the selected sample collection chamber (2068). Suitable forms of preliminary analysis may include, for example, x-ray analysis, bioimpedance analysis, visual analysis via CCD or direct visual inspection, and/or etc.

Once a desired number of tissue samples are collected and/or analyzed within the selected sample collection chamber (2068), cassette (2060) is adjusted to receive one or more tissue samples within another selected sample collection chamber (2068). To adjust cassette (2060) to receive one or more tissue samples within another selected sample collection chamber (2068), cassette (2060) is rotated in a clockwise or counterclockwise direction. As described above, tissue transport tube (302) is generally stationary relative to cassette (2060). Accordingly, rotational movement of cassette (2060) results in tissue transport tube (302) being placed in communication with another selected tissue communication bore (2064) and corresponding selected sample collection chamber (2068).

Figure 33:
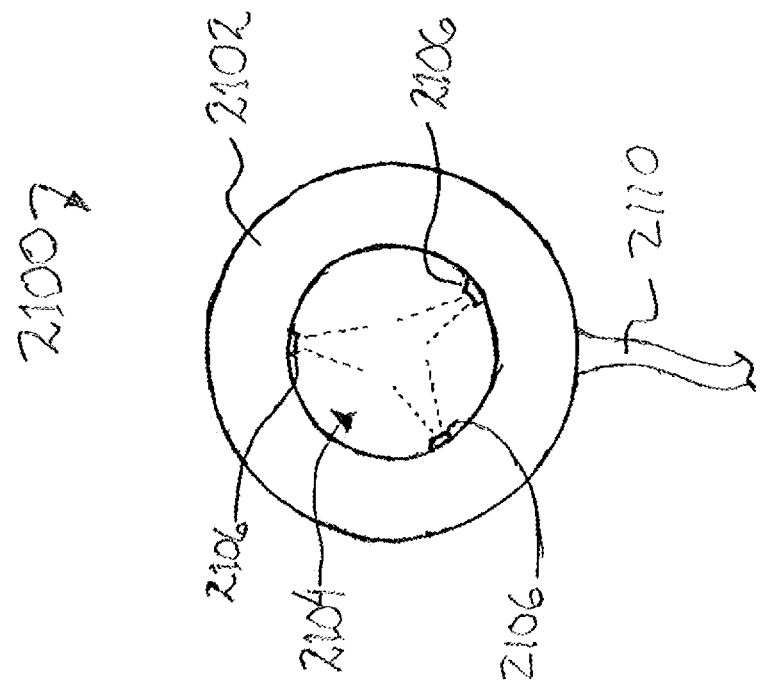
FIG. 33 depicts a side elevational view of the fluid applicator of FIG. 32.
Figure 32:
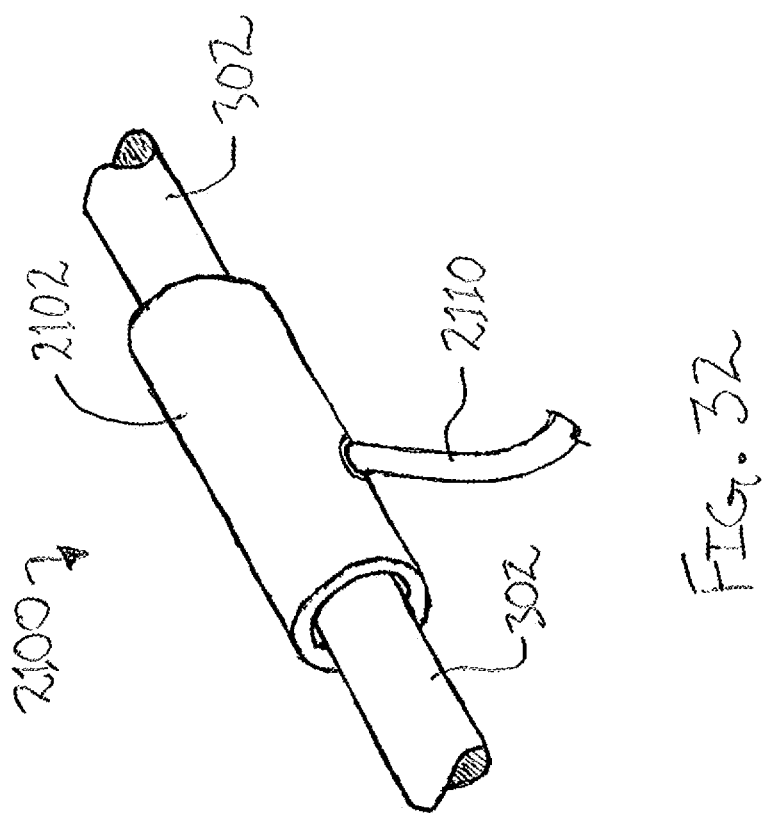
FIG. 32 depicts a perspective view of a fluid applicator that may be readily incorporated into the tissue transport tube of the biopsy system of FIG. 1.

After cassette (2060) is adjusted as described above, vacuum is again applied to the selected sample collection chamber (2068) as described above. This pulls one or more tissue samples thorough tissue transport tube (302) and into the selected sample collection chamber (2068) via the selected tissue communication bore (2064). Once a desired number of tissue samples are acquired within the selected sample collection chamber (2068), preliminary analysis may then be optionally performed. Once performed, the process described above may be repeated again to communicate one or more tissue samples in to the other remaining tissue collection chambers (2068) until a desired total number of tissue samples have been collected FIGS. 32 and 33 show an exemplary fluid applicator (2100) for use with tissue transport tube (302) described above. Fluid applicator (2100) is generally configured to apply fluids to tissue samples as they pass through tissue transport tube (302). As can be seen in FIG. 32, fluid applicator (2100) comprises an applicator body (2102) coupled to a fluid tube (2110). Applicator body (2102) comprises a generally cylindrical shape defining a hollow interior (2104) extending through fluid applicator (2100). The proximal and distal ends of applicator body (2102) are generally configured to receive tissue transport tube (302). In the present example, tissue transport tube (302) is generally severed at applicator body (2102) to form two ends that couple to each corresponding end of applicator body (2102). In other examples, tissue transport tube (302) remains a single part. However, to permit applicator body (2102) to interact with the interior of tissue transport tube (302), it should be understood that in such examples tissue transport tube (302) may include perforations or openings to permit access.

Hollow interior (2104) of applicator body (2102) is best seen in FIG. 33. As can be seen, applicator body (2102) includes a plurality of nozzles (2106) directed into hollow interior (2104) of applicator body (2102). Although nozzles (2106) in the present example are shown as at least partially projecting into hollow interior (2104), it should be understood that in some examples nozzles (2106) are configured to be flush with applicator body (2102) to provide a consistent surface to thereby promote the flow of tissue samples therethrough. Each nozzle (2106) is generally configured to spray fluid into hollow interior (2104) of applicator body (2102). As will be described in greater detail below, fluid is generally communicated to each nozzle (2106) from fluid tube (2110) thorough applicator body (2102) and out each nozzle (2106).

Fluid tube (2110) is coupled to applicator body (2102) for the communication of fluids through applicator body (2102) and out of each nozzle (2106). Although not shown, it should be understood that fluid tube (2110) is in communication with a fluid source. As with other fluid sources described herein, this fluid source may be incorporated into vacuum control module (400), biopsy device (10), another component of biopsy system (2), or may be a standalone component. Fluid source of the present example is generally configured to communicate an anti-coagulant fluid to fluid tube (2110). In other examples, other fluids may be used in addition, or in alternative to anti-coagulant fluid. By way of example only, suitable fluids may include saline solution, lubricants, dies, and/or etc.

In an exemplary use, fluid applicator (2100) is disposed in-line of tissue transport tube (302) at some position between biopsy device (10) and tissue handler (310). Regardless of the particular positioning of fluid applicator (2100) relative to tissue transport tube (302), fluid applicator (2100) will generally apply any one or more of the fluids described above to tissue samples passing through tissue transport tube (302). In particular, as tissue samples enter applicator body (2102), the fluid source associated with fluid tube (2110) will supply the fluid to fluid tube (2110). The fluid when then travel through fluid tube (2110), into applicator body (2102) and out of nozzles (2106), thereby coating each tissue sample as it passes through hollow interior (2104) of fluid applicator (2100).

In some exemplary uses, fluid is applied as described above to fluid applicator (2100) on a constant basis such that at any given moment during the biopsy procedure, fluid will flow through nozzles (2106). In an alternative use, fluid flow is coordinated with the flow of tissue samples through tissue transport tube (302). For instance, in some uses, the fluid source is activated to supply fluid to nozzles (2106) only when tissue samples are being transported through tissue transport tube (302). In other uses, activation of the fluid source is timed to supply fluid to nozzles (2106) as a transported tissue sample arrives at fluid applicator (2100). In such a use, fluid applicator (2100) and or tissue transport tube (302) may include sensors or other devices to provide a signal when to activate the fluid source.

Figure 35:
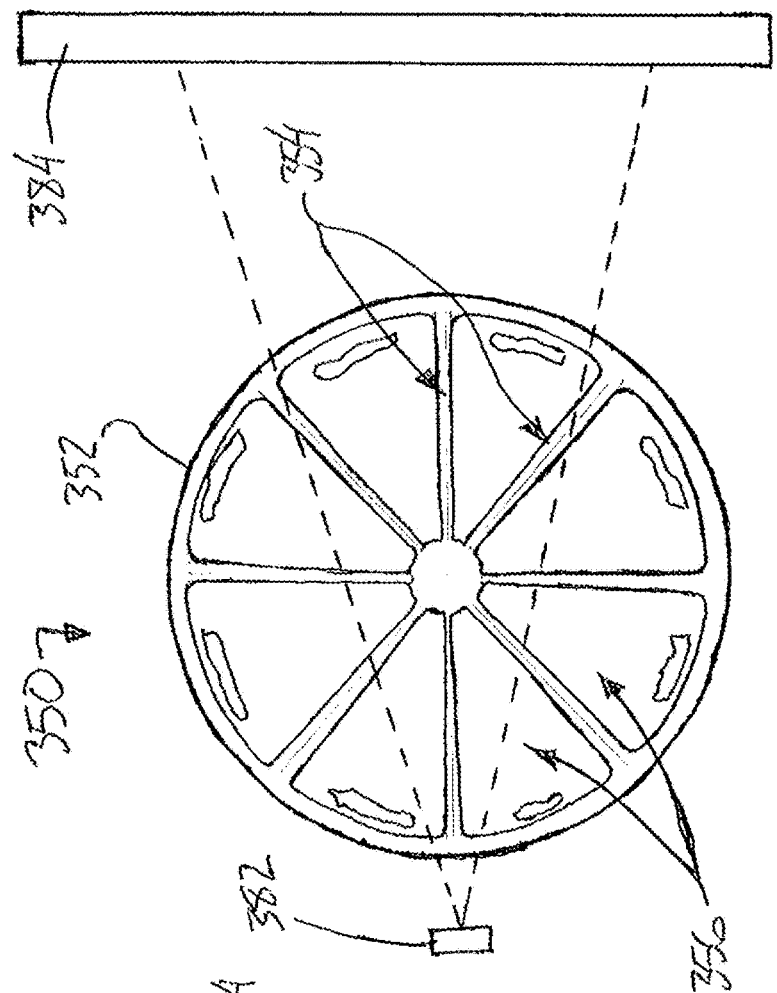
FIG. 35 depicts another top plan view of the alternative use for the tissue sample holder depicted in FIG. 34.
Figure 34:
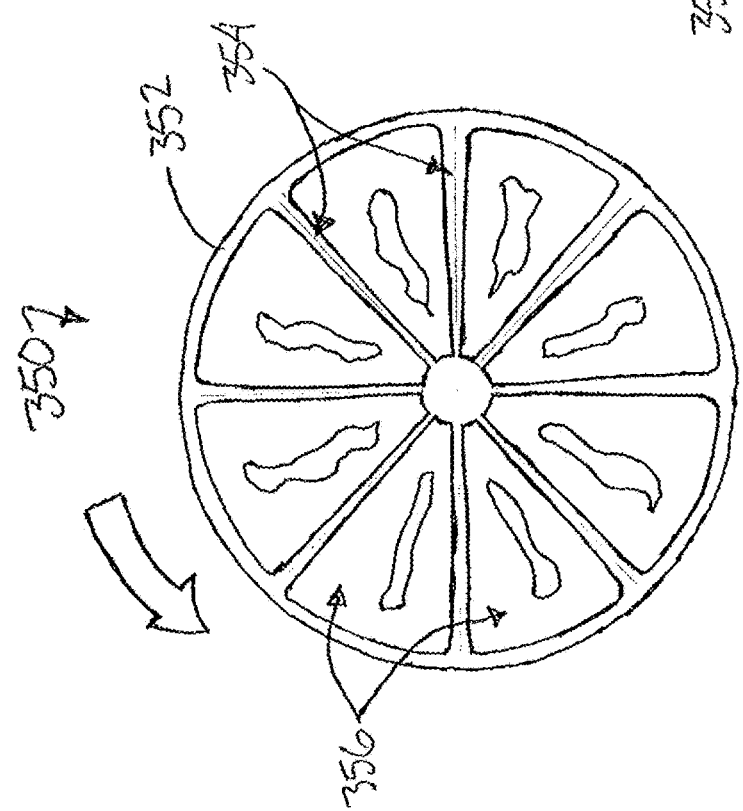
FIG. 34 depicts a top plan view of an alternative use for the tissue sample holder of the biopsy system of FIG. 1.

FIGS. 34 and 35 show an exemplary alternative use for tissue sample tray (350) described above. As seen in FIG. 34, a plurality of tissue samples is collected within tissue sample tray (350) with a single tissue sample deposited within each sample chamber (356). At this stage, tissue samples are collected in substantially the same way as described above. For instance, a single tissue sample is transported through tissue transport tube (302) and into a sample chamber (356) indexed with redirection elbow (344) of tissue directing top (342). Each sample chamber (356) is then subsequently filled by sequentially rotating sample tray (350) to place each sample chamber (356) into alignment with redirection elbow (344).

Once each sample chamber (356) of sample tray (350) is filled with a tissue sample, the alternative use of sample tray (350) begins. In the alternative use, sample tray (350) is rotated via rotation shaft (370) at a substantially high speed to effectively centrifuge the tissue samples disposed within sample tray (350). This high rate of rotation forces each tissue sample onto the wall of cylindrical body (352) and into a desirable spaced-out position. Such a positioning may be desirable to promote x-ray based analysis of each tissue sample. For instance, when initially received within sample tray (350), each tissue sample may not be in an ideal position for x-ray imaging because tissue samples may become balled-up or otherwise disorganized during entry into sample tray (350). Thus, the rapid rotation of sample tray (350) may be desirable to provide a spaced-out position for x-ray imaging.

Once sample tray (350) has been rotated at a substantially high speed, rotation may cease and imaging may occur as shown in FIG. 35. It should be understood that since each tissue sample is repositioned within sample tray (350), it may be desirable to reposition x-ray source (382) and x-ray detector (384) into the position shown in FIG. 35. In this position, x-ray radiation is shot laterally across sample tray (350) instead of downwardly onto sample tray (350). In this configuration, the field of view of x-ray source (382) and x-ray detector (384) may be insufficient to image all samples with a single shot. Thus, to image all samples, sample tray (350) may be rotated in response to x-ray imaging. In the present configuration, two samples are imaged at a time such that on x-ray image is taken to image two samples and then sample tray (350) is rotated to image the next two samples. Of course, this is only one exemplary sequence for imaging. In other examples, source (382) and x-ray detector (384) may be configured to image any suitable number of samples at a time, thereby providing different imaging/rotation schemes.

FIG. 36 shows an exemplary alternative tissue transport tube (2200) that may be readily incorporated into tissue handling assembly (300) in lieu of tissue transport tube (302) described above. Like with tissue transport tube (302), tissue transport tube (2200) comprises an elongate tube extending between biopsy device (10) and tissue handler (310). However, unlike tissue transport tube (302), tissue transport tube (2200) of the present example includes one or more electrical leads (2204) extending longitudinally through a wall (2202) of tissue transport tube (2200). In the present example, tissue transport tube (2200) includes two electrical leads (2204) positioned on opposite sides of wall (2202). However, it should be understood that in other examples any other suitable number of electrical leads (2204) are used with any suitable spacing.

Electrical leads (2204) are generally configured to change at least one physical property in response to movement of tissue transport tube (2200). In some examples, this change in at least one physical property may be used to detect kinking in tissue transport tube (2200). For instance, in one example electrical leads (2204) are configured to change resistance in response to bending of tissue transport tube (2200). In particular, when tissue transport tube (2200) of the present example is bent, one electrical lead (2204) may compress and another electrical lead (2204) may stretch due to the positioning of electrical leads (2204). This compression and stretching may result in increased resistance of the compressed electrical lead (2204) and decreased resistance of the stretched electrical lead (2204). Although not shown, it should be understood that each electrical lead (2204) is connected to various electrical instruments to detect these changes in resistance. Once the detected resistances for electrical leads (2204) reach certain threshold values, electrical instruments are configured to communicate a signal either directly to an operator or to vacuum control module (400). Such a signal may be indicative of an error condition such as kinking of tissue transport tube (2200).

Although electrical leads (2204) are described herein as changing in electrical resistance to detect kinking of tissue transport tube (2200), it should be understood that in other examples electrical leads (2204) may change other physical properties. For instance, in some examples measurements to detect kinking may be based on capacitance or other similar physical properties. To detect changes in physical properties of electrical leads (2204), some examples may include a time domain reflectometer circuit incorporated into biopsy device (10) or vacuum control module (400). Such circuit may be configured to supply small electrical pulses though electrical leads (2204) and then measure small differences in time required for the electrical pulses to reflect from one end of each electrical lead (2204) to the other.

In other examples, electrical leads (2204) may not be used for detection of kinking at all. Instead, at least a portion of each electrical leas (2204) is in communication with the interior of tissue transport tube (2200). When in communication with the interior of tissue transport tube (2200), electrical leads (2204) are used to take impedance measurements of any tissue samples passing through tissue transport tube (2200). Such impedance measurements may be used for a variety of purposes. For instance, in some examples impedance measurements are used to merely detect the presence of a tissue sample at predetermined positions along the axial length of tissue transport tube (2200). In other examples, impedance measurements are used to identify certain physical properties of tissue samples passing through tissue transport tube (2200) such as the identification of pathological substances.

Figure 38:
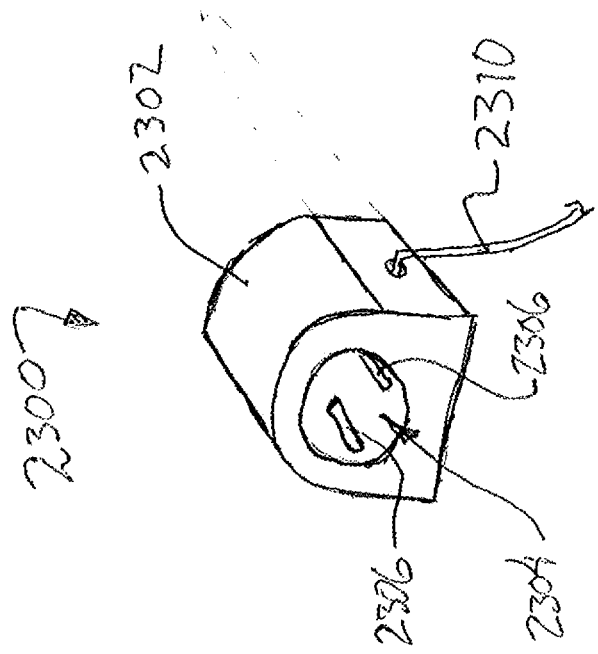
FIG. 38 depicts another perspective view of the tissue sensor of FIG. 37.
Figure 37:
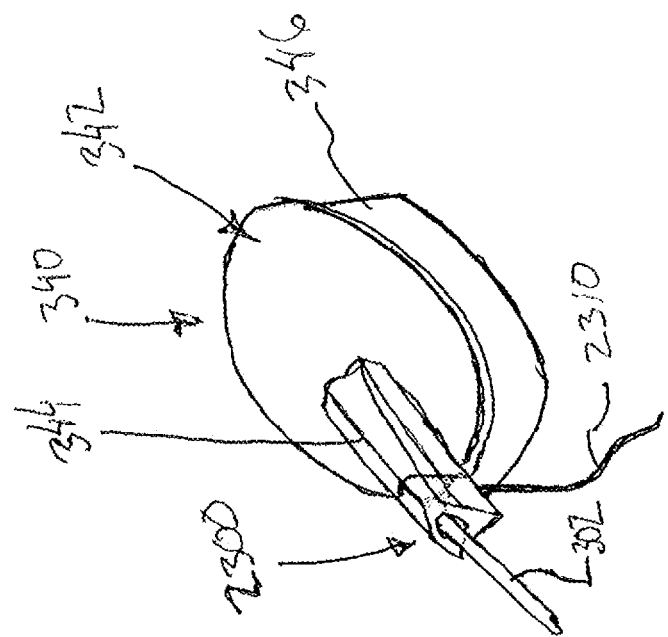
FIG. 37 depicts a perspective view of a tissue sensor incorporated into the tissue handling assembly of FIG. 2.

FIGS. 37 and 38 depict an exemplary tissue sensor (2300) that may be readily incorporated into tissue handling assembly (300). As shown in FIG. 37, tissue sensor (2300) of the present example is positioned between tissue transport tube (302) and tissue directing top (342) of tissue handling assembly (300). However, it should be understood that in other examples tissue sensor (2300) may be positioned in a variety of alternative positions such as between biopsy device (10) and tissue transport tube (302), and/or at some position along the axial length of tissue transport tube (302). As will be understood, tissue sensor (2300) is generally configured to sense the presence of tissue samples as they are transported though tissue handling assembly (300). Thus, in the present example tissue sensor (2300) is generally configured to provide an indication of when tissue samples are transferred from tissue transport tube (302) and into tissue sample holder (304) through tissue directing top (342).

As best seen in FIG. 38, tissue sensor (2300) includes an outer body (2302), and a sensor wire (2310) extending from outer body (2302). Outer body (2302) defines an opening (2304) extending entirely though tissue sensor (2300). Opening (2304) is generally configured to communicate tissue samples through tissue sensor (2300) to other portions of tissue handling assembly (300).

The interior of outer body (2302) includes one or more sensors (2306). Sensors (2306) are generally configured to sense the presences of one or more tissue samples. Although the present example is shown as including two sensors (2306), it should be understood that in other examples any suitable number of sensors (2306) may be used. Sensors (2306) of the present example comprise electrical sensors. In this configuration, sensors (2306) are used to measure impedance to detect the presence of tissue samples. In some instances, impedance measurements may also be used to detect other physical properties of tissue samples such as the presence of pathogenic substances. In other examples, sensors (2306) can comprise many alternative types of sensors such as laser sensors, light sensors, Doppler sensors, mechanical switches, and/or etc.

In an exemplary use, sensors (2306) detect the presence of tissue samples or other information as tissue samples pass through tissue sensor (2300). This results in an electrical signal being communicated through sensor wire (2310). Sensor wire (2310) may be coupled with vacuum control module (400) or other intermediate circuitry to process electrical signals communicated through sensor wire (2310). One the electrical signals are processed; various control algorithm adjustments may be initiated based on the detected tissue samples. For instance, once the presence of one or more tissue samples is detected, vacuum control module (400) may terminate a tissue transport operation and indicate to an operator that a tissue sample has been collected.

Figure 39:
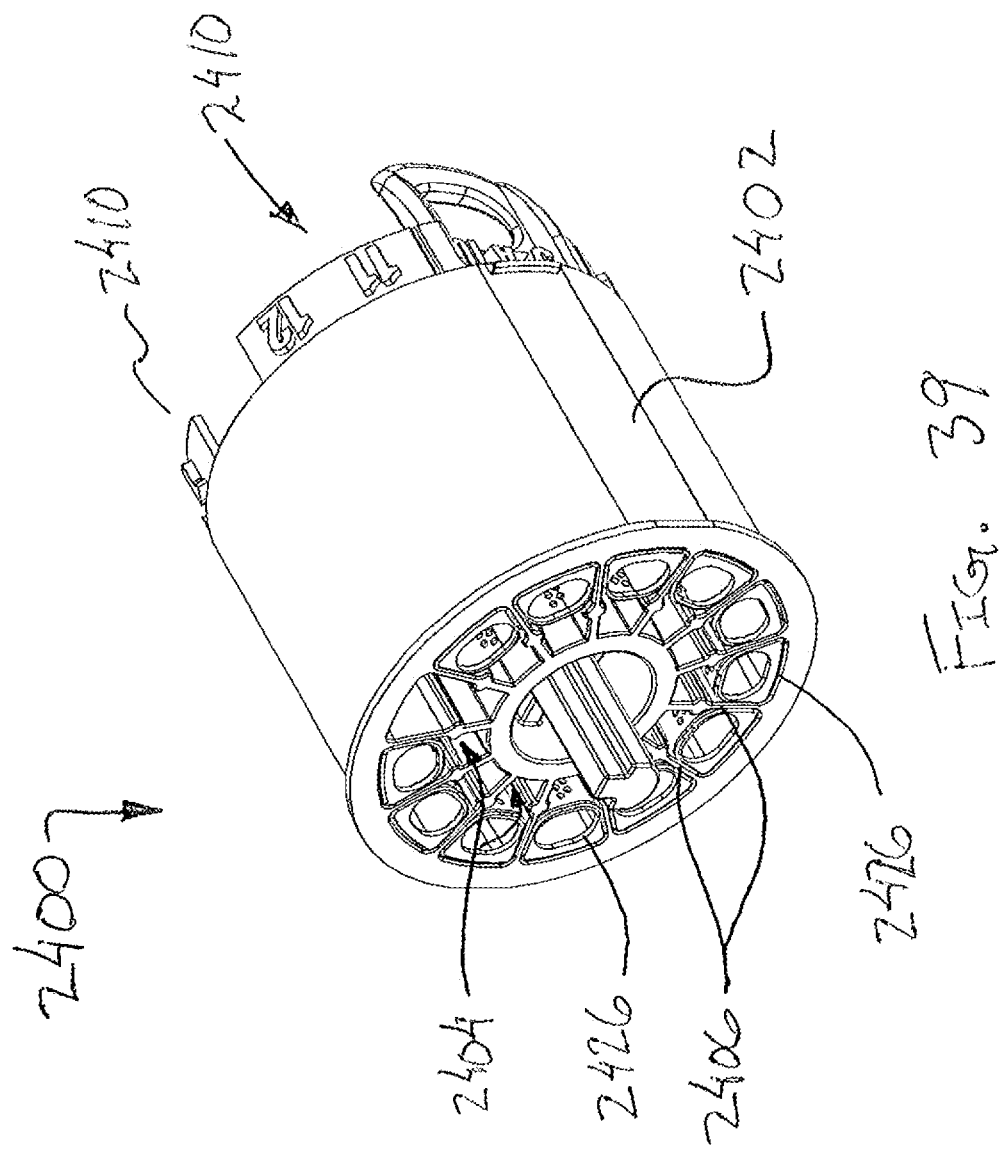
FIG. 39 depicts a perspective view of yet another tissue sample holder that may be readily incorporated into the biopsy system of FIG. 1.

FIG. 39 shows an exemplary alternative tissue sample holder (2400) that may be readily incorporated into tissue handling assembly (300) in lieu of tissue sample holder (340). Tissue sample holder (2400) is generally configure to store tissue sample in a circular arrangement about an axis. Accordingly, it should be understood that tissue sample holder (2400) is generally rotatable to align a portion of tissue sample holder (2400) with tissue transport tube (302) for the collection of tissue samples within a plurality of predetermined locations within tissue sample holder (2400). Tissue sample holder (2400) generally comprises a manifold (2402) and one or more trays (2410). Manifold (2402) defines a plurality of chambers (2404) by a plurality of radially extending sidewalls (2406). As will be described in greater detail below, each chamber (2404) is generally configured to receive at least a portion of tray (2410). In addition each chamber (2404) is generally configured to communicate axial vacuum to each tray (2410) to promote collection of tissues samples within each tray (2410). In some example manifold (2402) is configured in accordance with at least some of the teachings of US Pub. No. 2014/0039343, entitled "Biopsy System," published on Feb. 2, 2014, the disclosure of which is incorporated by reference herein.

Figure 40:
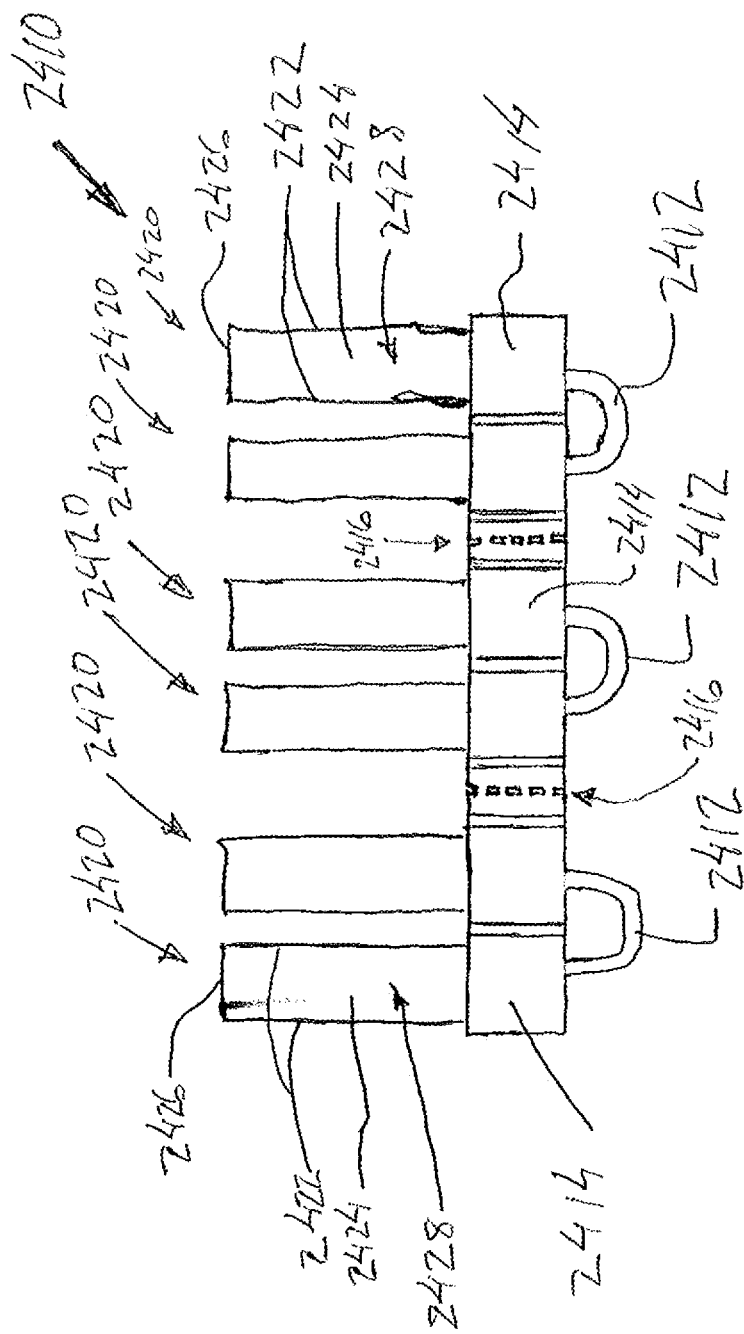
FIG. 40 depicts a top plan view of a tray that may be used with the tissue sample holder of FIG. 39.

FIG. 40 shows tray (2410) in greater detail. Each tray (2410) is generally configured to removably engage manifold (2402). Tray (2410) of the present example include one or more grips (2412), a one or more couplers (2414), and a plurality of strips (2420) extending distally from a single coupler (2414). Each strip (2420) defines a pair of sidewalls (2422), a floor (2424), and a distal end (2426). The combination of sidewalls (2422), floor (2424), and distal end (2426) together define a tissue sample chamber (2428). Tissue sample chamber (2428) is generally configured to receive a single tissue sample, although in other examples tissue sample chamber (2428) may be configured to receive multiple tissue samples.

In the present example, a pair of strips (2420) are joined by a single coupler (2414) such that three couplers (2414) join three pairs of strips (2420) for a total of six strips (2420). Each coupler (2414) is joined to an adjacent coupler (2414) by a perforated region (2416). Perforated region (2416) is generally perforated such that each coupler (2414) is configured to be selectively separated from the other coupler (2414). This permits an operator to selectively separate tray (2410) into different segments for separate storage of tissue samples or to use different tray (2410) configurations as may be desired. Although the present example is shown as having the configuration described above, it should be understood that any suitable strip (2420)/coupler (2414) configuration may be used in other examples. In addition, it should be understood that in some examples tray (2410) is configured in accordance with at least some of the teachings of US Pub. No. 2014/0039343, entitled "Biopsy System," published on Feb. 2, 2014, the disclosure of which is incorporated by reference herein.

Figure 41:
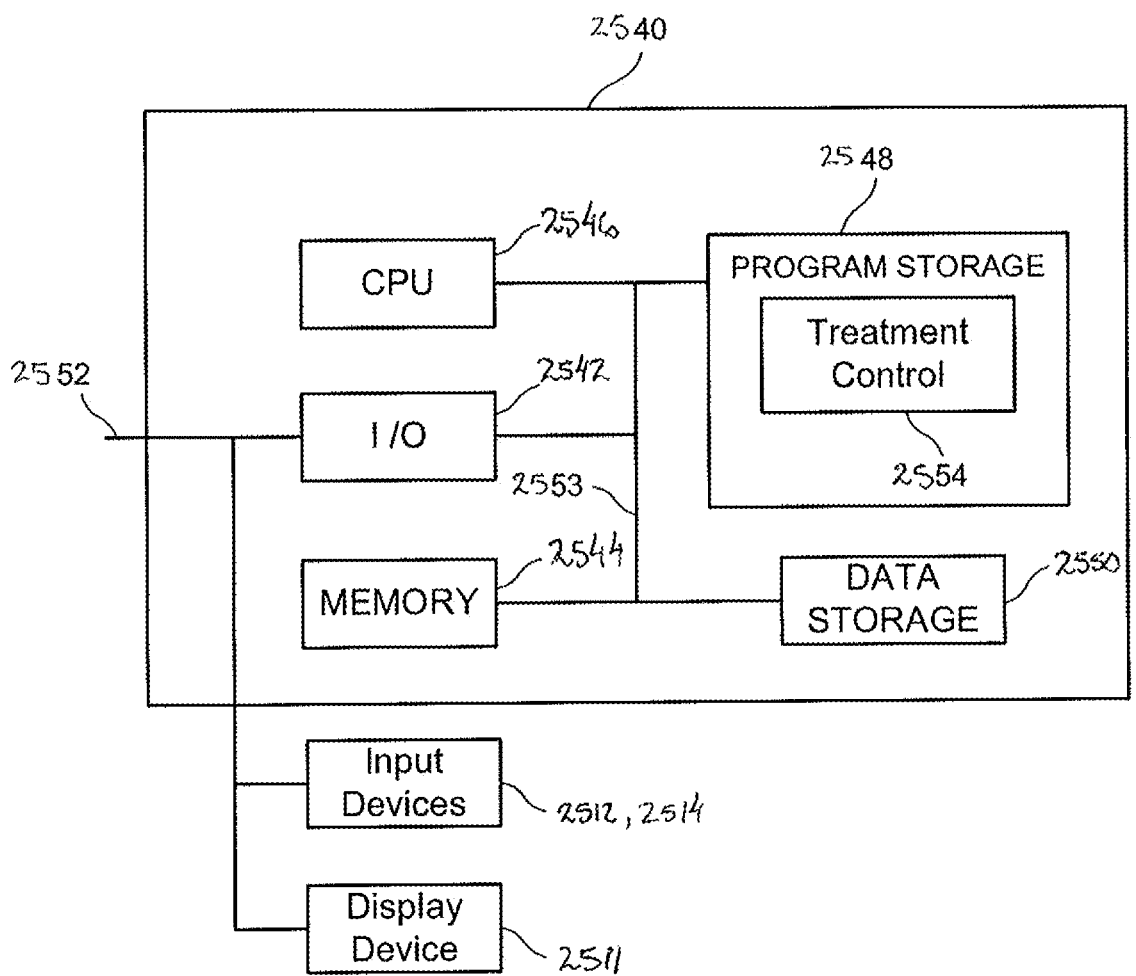
FIG. 41 depicts a schematic view of an exemplary treatment control computer that may be readily incorporated into the biopsy system of FIG. 1.

FIG. 41 shows an exemplary treatment control computer (2540) that may be readily incorporated into biopsy system (2) to control any of the electronic devices described herein. In some examples, treatment control computer (2540) is incorporated into biopsy system (2) as a discrete unit. Alternatively, in other examples treatment control computer (2540) is incorporated into biopsy device (10) and/or vacuum control module (400). The present example includes computer software (vacuum control module (400)), which assists a user to plan for, execute, and review the results of a medical treatment procedure, as will be discussed in more detail below. For example, vacuum control module (400) assists a user to plan for a medical treatment procedure by enabling a user to more accurately position probe (100) and to control various operational features of biopsy device (10) during a biopsy procedure.

For purposes of this application, the terms "code", "software", "program", "application", "software code", "software module", "module" and "software program" are used interchangeably to mean software instructions that are executable by a processor.

Treatment control computer (2540) of the present example manages planning of treatment for a patient. The computer (2540) is connected to a communication link (2552) through an I/O interface (2542) such as a USB (universal serial bus) interface, which receives information from and sends information over the communication link (2552) to a voltage generator (not shown). The computer (2540) includes memory storage (2544) such as RAM, processor (CPU) (2546), program storage (2548) such as ROM or EEPROM, and data storage (2550) such as a hard disk, all commonly connected to each other through a bus (2553). The program storage (2548) stores, among others, a treatment control module (2554) which includes a user interface module (2570) that interacts with an operator in planning for, executing and reviewing the result of a treatment. In the present example, user interface module (2570) includes one or more input devices (2512, 2514) and a display device (2511). Any of the software program modules in the program storage (2548) and data from the data storage (2550) can be transferred to the memory (2544) as needed and is executed by the CPU (2546).

In one example, the computer (2540) is built into the voltage generator. In another embodiment, the computer (2540) is a separate unit which is connected to the vacuum control module (400) through the communications link (2552). In another embodiment, the communication link (2552) is a USB link. In another embodiment, the computer (2540) can reside in both the control module (400) and the biopsy device (10) in communication with each other.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system, the biopsy system comprising:
 (a) a biopsy device, the biopsy device including:
  (i) a probe,
  (ii) a needle extending from the probe, and
  (iii) a cutter, the cutter being movable relative to the needle to sever one or more tissue samples, the cutter defining a cutter lumen extending from a distal end of the cutter to a proximal end of the cutter;
 (b) a tissue handler configured to receive the one or more tissue samples severed by the cutter;
 (c) a processor adapted to control the cutting and receipt of tissue in the tissue handler; and
 (d) a tissue transport tube in communication with the cutter and the tissue handler, the transport tube being configured to communicate the one or more tissue samples severed by the cutter to the tissue handler, the transport tube including one or more electrical leads extending axially though a wall of the transport tube, the one or more electrical leads being responsive to movement of the transport tube to detect bending of the transport tube.

2. The biopsy system of claim 1, the one or more electrical leads being configured to change in at least one physical property in response to movement of the transport tube.

3. The biopsy system of claim 2, the one or more electrical leads being configured to change in resistance in response to bending of the transport tube.

4. The biopsy system of claim 2, the one or more electrical leads being configured to change in capacitance in response to bending of the transport tube.

5. The biopsy system of claim 1, the one or more electrical leads including two electrical leads, each electrical lead being position on an opposite side of the wall of the transport tube.

6. The biopsy system of claim 1, the one or more electrical leads including a first electrical lead and a second electrical lead, the first electrical lead being position on an opposite side of the wall of the transport tube relative to the second electrical lead, the first electrical lead and the second electrical lead being configured to change in resistance in response to being of the transport tube, the change in resistance for the first electrical lead being different from the change in resistance for the second electrical lead for a given bend of the transport tube.

7. The biopsy system of claim 1, further comprising a domain reflector circuit, the processor being in communication with the domain reflector circuit and the one or more electrical leads, the processor being configured to:
apply a series of electrical pulses to the one or more electrical leads via the domain reflector circuit,
measure a difference in time for each electrical pulse of the series of electrical pulses to communicate from one end of each of the one or more electrical leads to another relative to a predetermined time, and
detect a magnitude of movement of the transport tube based on the difference in time.

8. The biopsy system of claim 1, the one or more electrical leads being entirely embedded within the wall of the transport tube.

9. The biopsy system of claim 1, a portion of at least one of the one or more electrical leads being exposed to an interior of the transport tube such that the portion of the at least one electrical lead is configured to engage the one or more tissue samples during transport through the transport tube.

10. The biopsy system of claim 1, each electrical lead of the one or more electrical leads extending axially through the transport tube from a distal end of the transport tube to a proximal end of the transport tube.

11. A biopsy system, the biopsy system comprising:
(a) a probe, the probe including:
(i) a body,
(ii) a needle extending from the body, and
(iii) a cutter, the cutter being movable relative to the needle to sever one or more tissue samples, the cutter defining a cutter lumen extending from a distal end of the cutter to a proximal end of the cutter;
(b) a tissue handler configured to receive the one or more tissue samples severed by the cutter; and
(c) a tissue transport tube in communication with the cutter and the tissue handler, the transport tube including a hollow cylindrical wall being configured to communicate the one or more tissue samples severed by the cutter from the cutter and to the tissue handler, the transport tube including a first electrical lead and a second electrical lead extending through the wall of the transport tube, the first electrical lead and the second electrical lead being positioned relative to each other cross-sectionally within the wall to deform in response movement of the transport tube.

12. The biopsy system of claim 11, the first electrical lead being positioned cross-sectionally within the wall on an opposite side of an interior defined by a wall relative to the second electrical lead.

13. The biopsy system of claim 11, the first electrical lead and the second electrical lead both being configured to stretch and compress in response movement of the transport tube.

14. The biopsy system of claim 11, the first electrical lead being configured to deform inversely relative to the second electrical lead.

15. The biopsy system of claim 11, a portion of the first electrical lead and the second electrical lead being exposed to an interior of the transport tube such that the portion of the first electrical lead and the second electrical lead is configured to engage the one or more tissue samples during transport through the transport tube, the first electrical lead and the second electrical lead being configured to detect the position of the one or more tissue samples within the transport tube.

16. A biopsy system, the biopsy system comprising:
(a) a biopsy device, the biopsy device including:
(i) a body,
(ii) a needle extending from the body, and
(iii) a cutter, the cutter being movable relative to the needle to sever one or more tissue samples, the cutter defining a cutter lumen extending from a distal end of the cutter to a proximal end of the cutter;
(b) a vacuum control module in communication with the biopsy device; and
(c) a transport tube including a wall, the wall defining a transport lumen in communication with the cutter and the vacuum control module, the transport tube being configured to communicate the one or more tissue samples severed by the cutter to a portion of the vacuum control module, the transport tube including a first electrical lead and a second electrical lead embedded within the wall extending the length of the transport tube, the first electrical lead and the second electrical lead being configured to deform in response to movement of the transport tube to detect bending of the transport tube.

17. The biopsy system of claim 16, the vacuum control module including a tissue handler, the transport tube being in communication with the tissue handler.

18. The biopsy system of claim 16, the vacuum control module further including a processor, the processor being in communication with the first electrical lead and the second electrical lead.

19. The biopsy system of claim 18, the processor being configured to:
apply a series of electrical pulses to the first electrical lead and the second electrical lead,
measure a difference in time for each electrical pulse of the series of electrical pulses to communicate from one end of the first electrical lead and the second electrical lead to another relative to a predetermined time, and
detect a magnitude of movement of the transport tube based on the difference in time.

20. The biopsy system of claim 16, the transport tube physically coupling the vacuum control module to the biopsy device.

* * * * *